(12) United States Patent
Leitch et al.

(10) Patent No.: US 9,944,572 B2
(45) Date of Patent: *Apr. 17, 2018

(54) TANDEM TRANSFER HYDROGENATION AND OLIGOMERIZATION FOR HYDROCARBON PRODUCTION

(71) Applicant: California Institute of Technology, Pasadena, CA (US)

(72) Inventors: David Leitch, Pasadena, CA (US); Jay A. Labinger, Claremont, CA (US); John E. Bercaw, Pasadena, CA (US); Yan Choi Lam, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/596,255

(22) Filed: May 16, 2017

(65) Prior Publication Data

US 2017/0320792 A1    Nov. 9, 2017

Related U.S. Application Data

(63) Continuation of application No. 14/157,744, filed on Jan. 17, 2014, now Pat. No. 9,676,680.

(60) Provisional application No. 61/753,768, filed on Jan. 17, 2013.

(51) Int. Cl.
| | |
|---|---|
| *C07C 2/74* | (2006.01) |
| *C07C 2/58* | (2006.01) |
| *C07C 11/02* | (2006.01) |
| *C07C 15/12* | (2006.01) |

(52) U.S. Cl.
CPC .......... *C07C 2/74* (2013.01); *C07C 2/58* (2013.01); *C07C 11/02* (2013.01); *C07C 15/12* (2013.01); *C07C 2531/24* (2013.01); *C07C 2531/28* (2013.01)

(58) Field of Classification Search
CPC .... C07C 2/74; C07C 2/58; C07C 2/54; C07C 2/60; C07C 2/76; C07C 2531/24; C07C 2531/36
USPC .............. 585/16; 502/117, 152, 169, 353
See application file for complete search history.

(56) References Cited

U.S. PATENT DOCUMENTS

| | | | | |
|---|---|---|---|---|
| 4,197,419 A | * | 4/1980 | Schrock | C07C 2/34 556/43 |
| 4,430,515 A | * | 2/1984 | Bobsein | C07C 2/22 502/224 |
| 4,764,635 A | | 8/1988 | Ramachandran et al. | |
| 2005/0272966 A1 | | 12/2005 | Bassett et al. | |
| 2007/0060781 A1 | * | 3/2007 | Goldman | B01J 23/28 585/708 |

(Continued)

OTHER PUBLICATIONS

Hebden et al., "Dihydrogen/Dihydride or Tetrahydride? An Experimental and Coputational Investigation of Pincer Iridium Polyhydrides," Inorg. Chem., vol. 49, pp. 1733-1742, 2010.

(Continued)

*Primary Examiner* — Philip Y Louie
*Assistant Examiner* — Aaron W Pierpont
(74) *Attorney, Agent, or Firm* — Gavrilovich, Dodd & Lindsey LLP

(57) ABSTRACT

A method for coupling an alkane with an alkene using a hydrogen transfer catalyst and an alkene dimerization catalyst to form one or more higher molecular weight hydrocarbons.

19 Claims, 42 Drawing Sheets

(56) References Cited

U.S. PATENT DOCUMENTS

2010/0028735 A1 2/2010 Bassett et al.
2011/0071331 A1 3/2011 Bassett et al.

OTHER PUBLICATIONS

Kim, Jong Ho, International Search Report and Written Opinion, PCT/US2014/011992, Korean Patent Office, dated May 15, 2014.
Leitch David C. et al., "Upgrading Light Hydrocarbons via Tandem Catalysis: A dual Homogeneous Ta/Ir System for Alkane/Alkene Coupling", J. Am. Chem. Soc., Jun. 25, 2013, vol. 135, pp. 10302-10305.
Moon, Kihwan, International Preliminary Examination Report on Patentability and Written Opinion, PCT/US2014/011992, The International Bureau of WIPO, dated Jul. 30, 2015.

* cited by examiner

TANDEM TRANSFER HYDROGENATION AND OLIGOMERIZATION FOR HYDROCARBON PRODUCTION

CROSS REFERENCE TO RELATED APPLICATIONS

This application is a continuation of U.S. patent application Ser. No. 14/157,744, filed Jan. 17, 2014, which application claims the benefit of U.S. Provisional Patent Application Ser. No. 61/753,768, filed on Jan. 17, 2013, which are incorporated herein by reference in their entirety.

FIELD OF THE INVENTION

The disclosure relates to hydrocarbon production by hydrogenation and oligomerizaton and, more particularly, to catalysis of alkanes and alkenes by a tandem transfer hydrogenation and oligomerization.

BACKGROUND

Light alkane gases (ethane, propane, butane) and low-boiling liquids (pentane, hexane, etc.) represent a considerable proportion of petroleum-derived hydrocarbons. These light alkanes are found in natural gas and petroleum reservoirs, and also generated as low-value byproducts of refinery processes such as catalytic cracking as well as in Fisher-Tropsch conversion of synthesis gas. The latter processes may also produce corresponding alkenes; streams containing substantial amounts of both alkane and alkene are commonly obtained. These light hydrocarbons have limited value as useful fuels, particularly in the transportation sector, which generally requires heavier hydrocarbons. As the cost of raw petrochemicals rises due to increased demand and an anticipated reduction in supply, and concern over carbon emissions leads to demands for increased energy efficiency, a method to convert these under-utilized light hydrocarbons into more valuable heavier products would greatly impact the production of chemical fuels.

SUMMARY

The disclosure provides methods and compositions to convert a mixture of hydrocarbons into a mixture of heavier hydrocarbons. In a simplified version, a mixture of an alkane and an alkene (which may or may not have the same carbon number) are coupled to give an overall increase of the average carbon number of the product components. This is accomplished through the action of two catalysts that act concurrently. In one embodiment, a first catalyst ("hydrogenation catalyst") is a transfer hydrogenation catalyst. For example, a hydrogenation catalyst suitable for transfer hydrogenation includes, but is not limited to, soluble organometallic species containing a metal from group 9; these same species immobilized on a solid support such as silica or alumina; and platinum group metals dispersed on a suitable support. In one embodiment, a suitable hydrogenation catalyst comprises formula I:

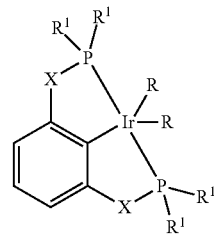

wherein, each R is independently H or a $(C_1\text{-}C_{30})$hydrocarbyl radical; each $R^1$ is independently a $(C_1\text{-}C_{30})$hydrocarbyl radical; and each X is independently an O or $CH_2$.

This hydrogenation catalyst serves to dehydrogenate the alkane reactants to alkenes, and to use the resulting $H_2$ to hydrogenate alkenes to alkanes. The alkenes may be sacrificial additives, or the products of the process itself. The second catalyst ("dimerization catalyst") affects alkene dimerization or oligomerization; dimers/oligomers can be a coupling of identical monomers ("homodimers/oligomers") or a coupling of similar, but not identical, monomers ("heterodimers/oligomers"). Exemplary dimerization catalysts include, but are not limited to, soluble organometallic species; supported versions of these same species; and zeolitic materials containing group 10 metal ions. In one embodiment, a suitable dimerization catalyst comprises Formula II:

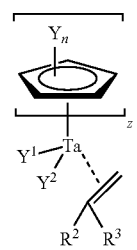

wherein, Z is either 1 or 2; n is an integer from 1 to 5; each Y is independently selected from D, H, optionally substituted $(C_1\text{-}C_6)$alkyl, silane, and $(C_1\text{-}C_4)$alkylsilane, $Y^1$ is a H, D, halo, =S, =O, $PMe_3$, =$C(H)(CMe_3)$; $Y^2$ is a H, D, halo, =S, =O, $PMe_3$, or absent; $R^2$ is a H, aryl, optionally substituted $(C_1\text{-}C_{15})$alkyl, or an optionally substituted $(C_1\text{-}C_{15})$hetero-alkyl, and $R^3$ is a H, aryl, optionally substituted $(C_1\text{-}C_{15})$alkyl, or an optionally substituted $(C_1\text{-}C_{15})$hetero-alkyl. In another embodiment, the dimerization catalyst comprises the Formula II(a):

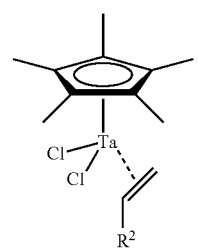

wherein, $R^2$ is an aryl, optionally substituted $(C_1\text{-}C_{15})$alkyl, or an optionally substituted $(C_1\text{-}C_{15})$hetero-alkyl. This catalyst converts the $C_n$ alkenes, present in the reactant mixture and/or formed by dehydrogenation catalysis, selectively into $C_{2n}$ or higher alkenes.

In a particular embodiment, the disclosure provides a method of coupling an alkane with an alkene so as to form one or more higher molecular weight hydrocarbons, comprising: coupling an alkane (e.g., a straight chain $(C_5\text{-}C_{10})$ alkane) with an alkene (e.g., a straight chain $(C_5\text{-}C_{10})$alkene) in the presence of catalysts comprising: (i) a hydrogen transfer catalyst and (ii) an alkene dimerization catalyst so as to generate one or more higher molecular weight hydrocarbons (e.g., alkanes or alkenes); wherein the hydrogen transfer catalyst is an iridium pincer complex catalyst and the alkene dimerization catalyst is tantalum catalyst, wherein the one or more higher molecular weight hydrocarbons comprise one or more carbon atoms from both the alkane and the alkene. In a further embodiment, both the hydrogen transfer catalyst and the dimerization catalyst are heterogeneous catalysts. In yet a further embodiment, the dimerization catalyst comprises a structure of Formula II:

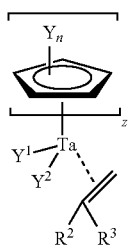

(II)

wherein, Z is either 1 or 2; n is an integer from 1 to 5; each Y is independently selected from D, H, optionally substituted $(C_1\text{-}C_6)$alkyl, silane, and $(C_1\text{-}C_4)$alkylsilane; $Y^1$ is a H, D, halo, =S, =O, $PMe_3$, =C(H) $(CMe_3)$; $Y^2$ is a H, D, halo, =S, =O, $PMe_3$, or absent; $R^2$ is a H, aryl, optionally substituted $(C_1\text{-}C_{15})$alkyl, or an optionally substituted $(C_1\text{-}C_{15})$hetero-alkyl; and $R^3$ is a H, aryl, optionally substituted $(C_1\text{-}C_{15})$alkyl, or an optionally substituted $(C_1\text{-}C_{15})$hetero-alkyl. In another embodiment, the dimerization catalyst comprises a structure of Formula II(a):

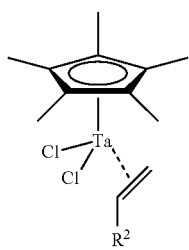

II(a)

wherein, $R^2$ is an aryl, optionally substituted $(C_1\text{-}C_{15})$alkyl, or an optionally substituted $(C_1\text{-}C_{15})$hetero-alkyl. In yet another embodiment, the hydrogen transfer catalyst comprises a structure of Formula I:

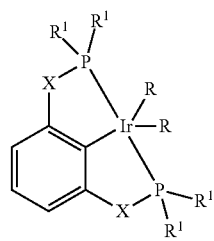

(I)

wherein, each R is independently H or a $(C_1\text{-}C_{30})$hydrocarbyl radical; each $R^1$ is independently a $(C_1\text{-}C_{30})$hydrocarbyl radical; and each X is independently an O or $CH_2$. In a further embodiment, the hydrogen transfer catalyst comprises a structure of Formula I(a):

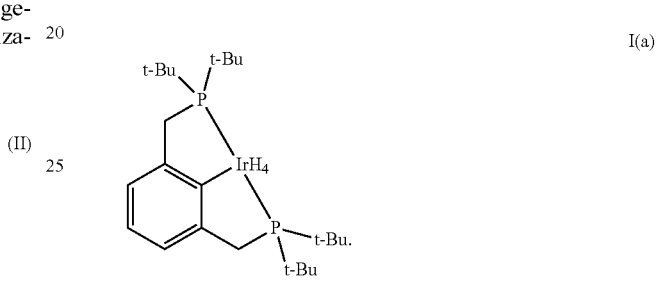

I(a)

In a particular embodiment, for the methods disclosed herein, the hydrogen transfer catalyst is immobilized on a solid support, wherein the reaction is carried out in a solvent, and wherein the method further comprises the step of separating the free hydrogen transfer catalyst from the solvent.

In a certain embodiment, for the methods disclosed herein, the hydrogen transfer catalyst is immobilized on a solid support, wherein the reaction is carried out in a solvent, and wherein the method further comprises the step of separating free hydrogen transfer catalyst from the solvent.

In a particular embodiment, the disclosure provides a method for coupling a first alkane with a second alkane to form one or more high molecular weight hydrocarbons, comprising: coupling a first alkane (e.g., a straight chain $(C_5\text{-}C_{10})$alkane) with a second alkane (e.g., a straight chain $(C_5\text{-}C_{10})$alkane) using a sacrificial hydrogen acceptor in the presence of catalysts comprising: (i) a hydrogen transfer catalyst and (ii) an alkene dimerization catalyst so as to generate one or more higher molecular weight hydrocarbons (e.g., alkanes or alkenes); wherein the hydrogen transfer catalyst is an iridium pincer complex catalyst and the alkene dimerization catalyst is tantalum catalyst, wherein the one or more higher molecular weight hydrocarbons comprise carbon atoms from the first alkane and the second alkane. In a further embodiment, the sacrificial hydrogen acceptor is styrene, tert-butylethylene or a combination thereof. In yet a further embodiment, the first alkane and the second alkane have the same structure. In an alternate embodiment, the first alkane and the second alkane do not have the same structure.

In a certain embodiment, for the methods disclosed herein, the hydrogen transfer catalyst and the dimerization catalyst are heterogeneous catalysts. In a further embodiment, the dimerization catalyst comprises a structure of Formula II:

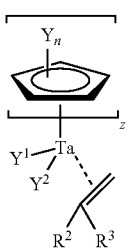

(II)

wherein: Z is either 1 or 2; n is an integer from 1 to 5; each Y is independently selected from D, H, optionally substituted $(C_1-C_6)$alkyl, silane, and $(C_1-C_4)$alkylsilane; $Y^1$ is a H, D, halo, ↑S, =O, PMe$_3$, =C(H)(CMe$_3$); $Y^2$ is a H, D, halo, =S, =O, PMe$_3$, or absent; $R^2$ is a H, aryl, optionally substituted $(C_1-C_{15})$alkyl, or an optionally substituted $(C_1-C_{15})$hetero-alkyl; and $R^3$ is a H, aryl, optionally substituted $(C_1-C_{15})$alkyl, or an optionally substituted $(C_1-C_{15})$hetero-alkyl. In another embodiment, the dimerization catalyst comprises a structure of Formula II(a):

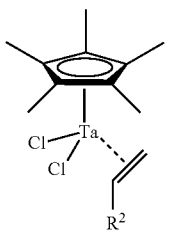

II(a)

wherein, $R^2$ is a phenyl. In yet another embodiment, the hydrogen transfer catalyst comprises a structure of Formula I:

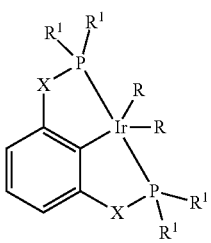

(I)

wherein, each R is independently H or a $(C_1-C_{30})$hydrocarbyl radical; each $R^1$ is independently a $(C_1-C_{30})$hydrocarbyl radical; and each X is independently an O or CH$_2$. In a further embodiment, the hydrogen transfer catalyst comprises a structure of Formula I(a):

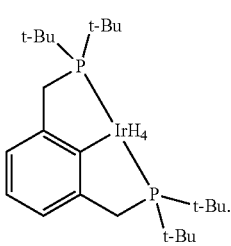

I(a)

In a particular embodiment, for the methods disclosed herein the hydrogen transfer catalyst is immobilized on a solid support, wherein the reaction is carried out in a solvent system, and wherein the method further comprises the step of separating free hydrogen transfer catalyst from the solvent. In a further embodiment, the solvent system comprises the first alkane and/or the second alkane.

In another embodiment, for the methods disclosed herein, the method further comprises the step of hydrogenating or reducing the one or more higher molecular weight hydrocarbons made by the methods disclosed herein.

The disclosure further provides for a liquid hydrocarbon fuel comprising the one or more higher molecular weight hydrocarbons made by the methods disclosed herein.

The disclosure also provides for an apparatus for carrying out the methods of the disclosure, which comprises an inlet and an outlet; and a bed or column comprising a hydrogen transfer catalyst and a dimerization catalyst disclosed herein. In yet a further embodiment, for the bed or column comprising the catalysts: (i) the hydrogen transfer catalyst is immobilized on a solid support; and (ii) the dimerization catalyst is immobilized on a solid support.

through 4 half-lives (two runs, final 160 h data point not included in linear correlation).

Figure 8:
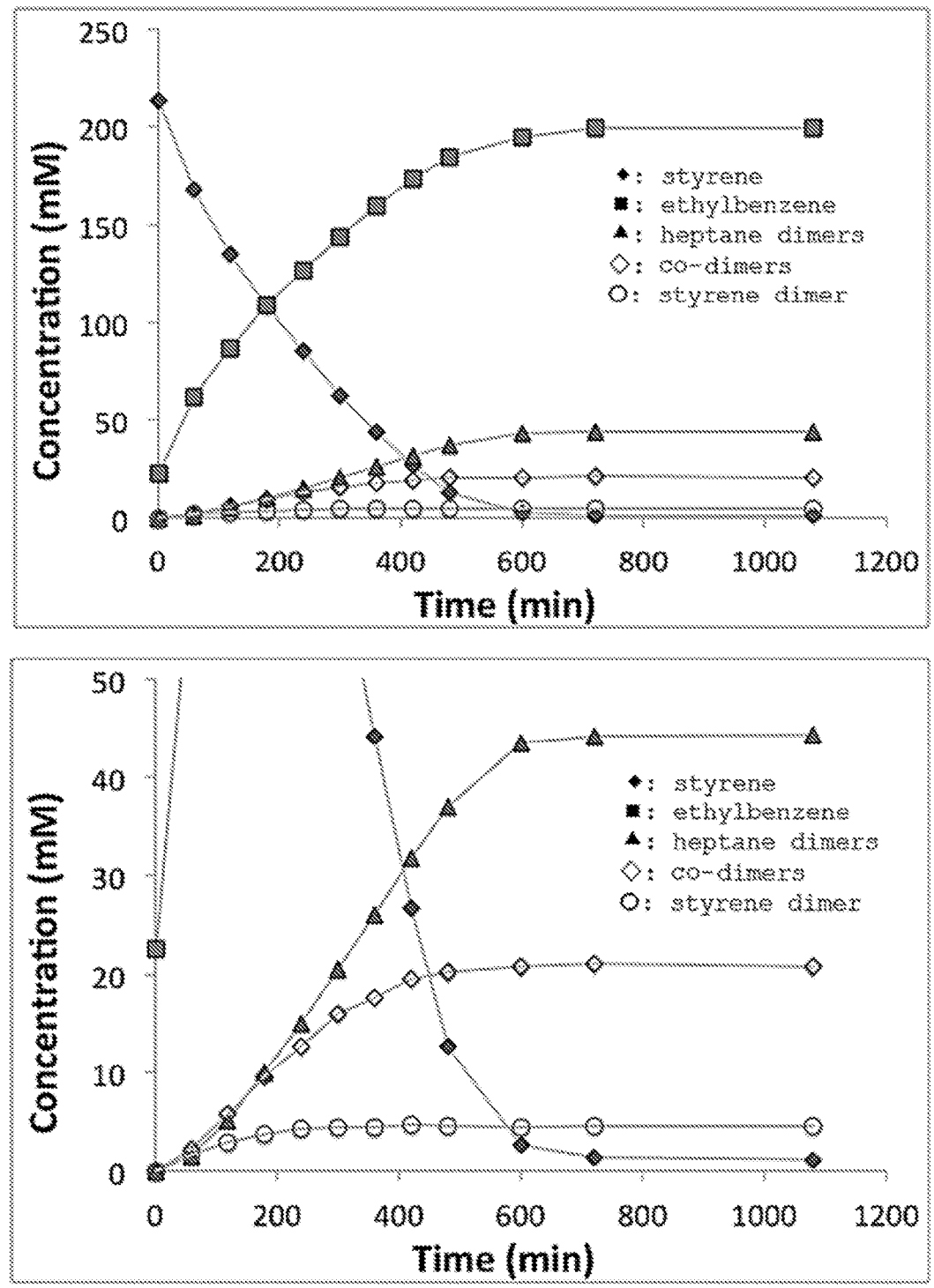

FIG. 8. Reaction progress for entry 7 (Table 4). Legend: ♦: styrene; ■: ethylbenzene; ▲: heptane dimers; ◇: co-dimers; ○: styrene dimer. Lines are drawn as visual guides only.

Figure 9:
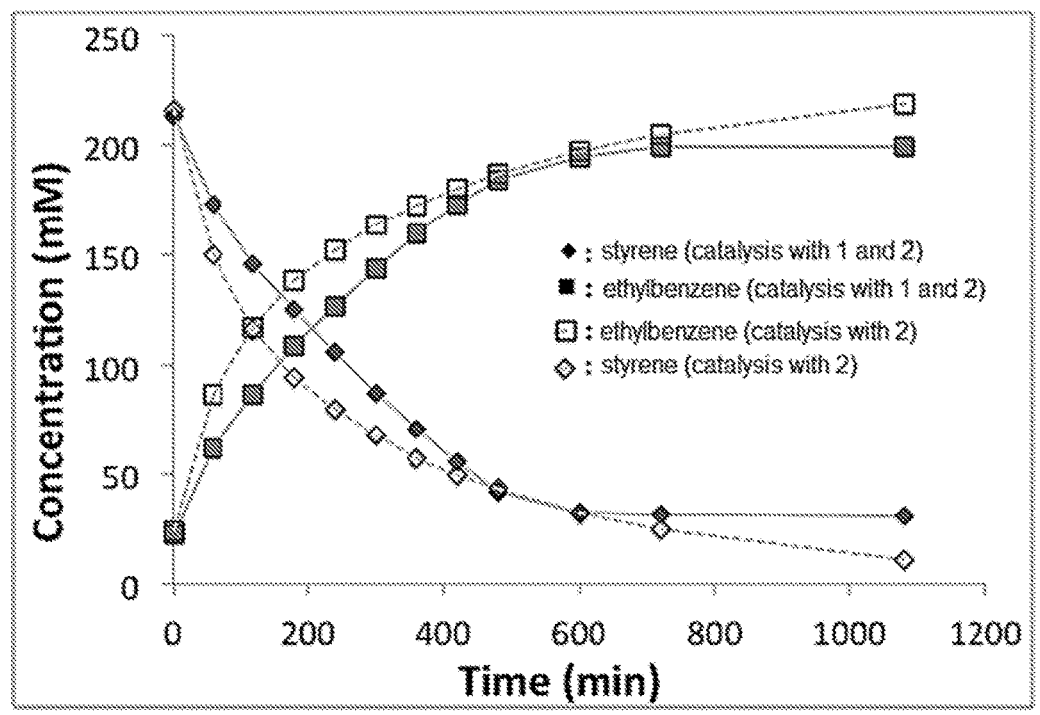

FIG. 9. Comparison of transfer hydrogenation progress in the conversion of styrene (diamonds) to ethylbenzene (squares) for catalysis with 2 only (unshaded diamonds and squares, dashed lines) and with 1 and 2 in tandem (shaded diamonds and squares, solid lines; values corrected for styrene converted to co-dimers and styrene dimers).

Figure 10:
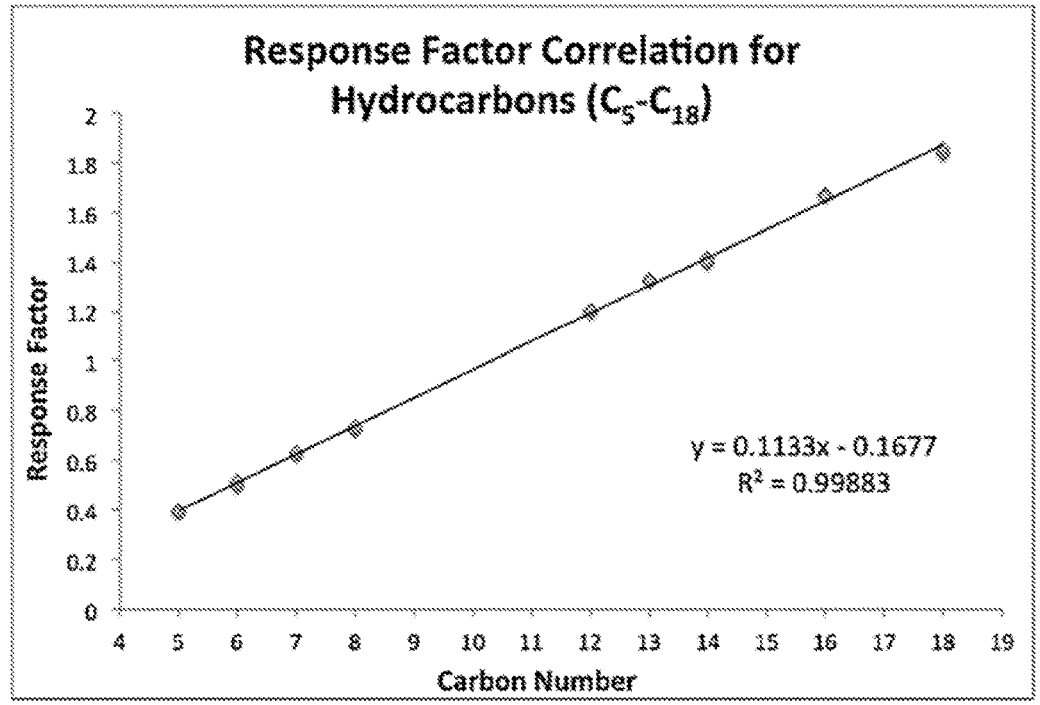

FIG. 10. Linear correlation of response factors versus carbon number.

Figure 11:
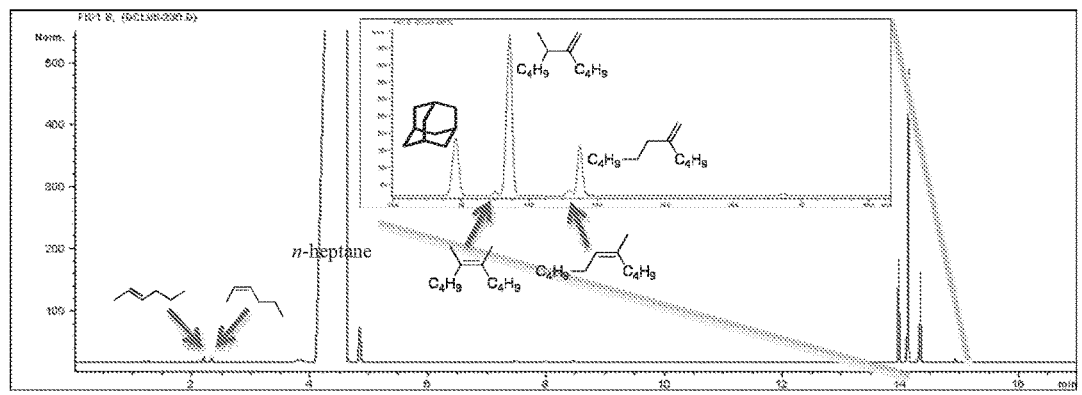

FIG. 11. GC trace of the dimerization of 1-hexene to produce $C_{12}$ dimers.

Figure 12:
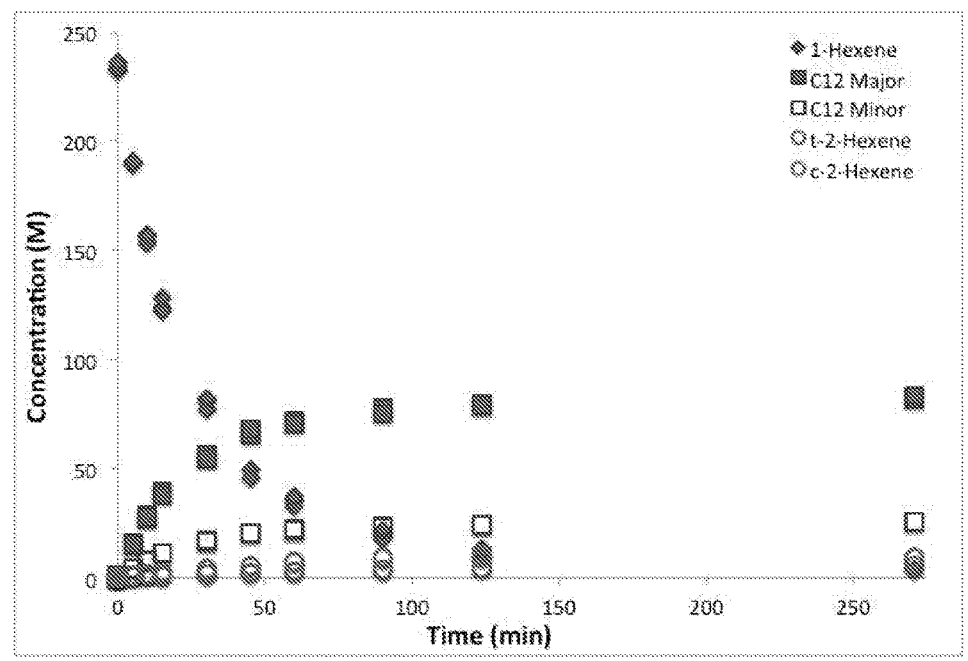

FIG. 12. Time course plot of the dimerization of 1-hexene by 1 (overlay of three runs).

Figure 13:
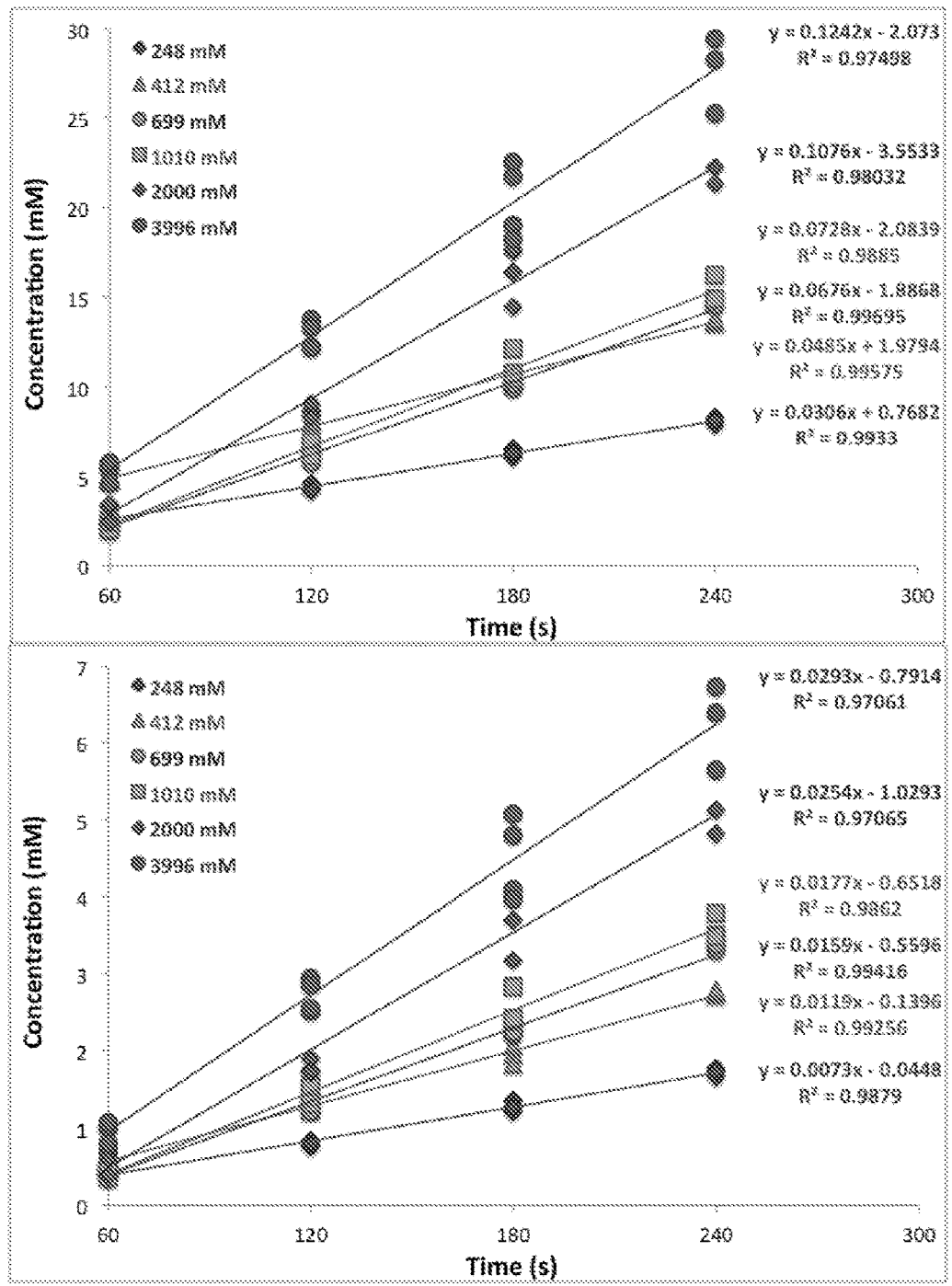

FIG. 13. Initial rate of 1-hexene dimerization as a function of $[1\text{-hexene}]_0$ at 80° C. Top: Rate vs.

Figure 14:
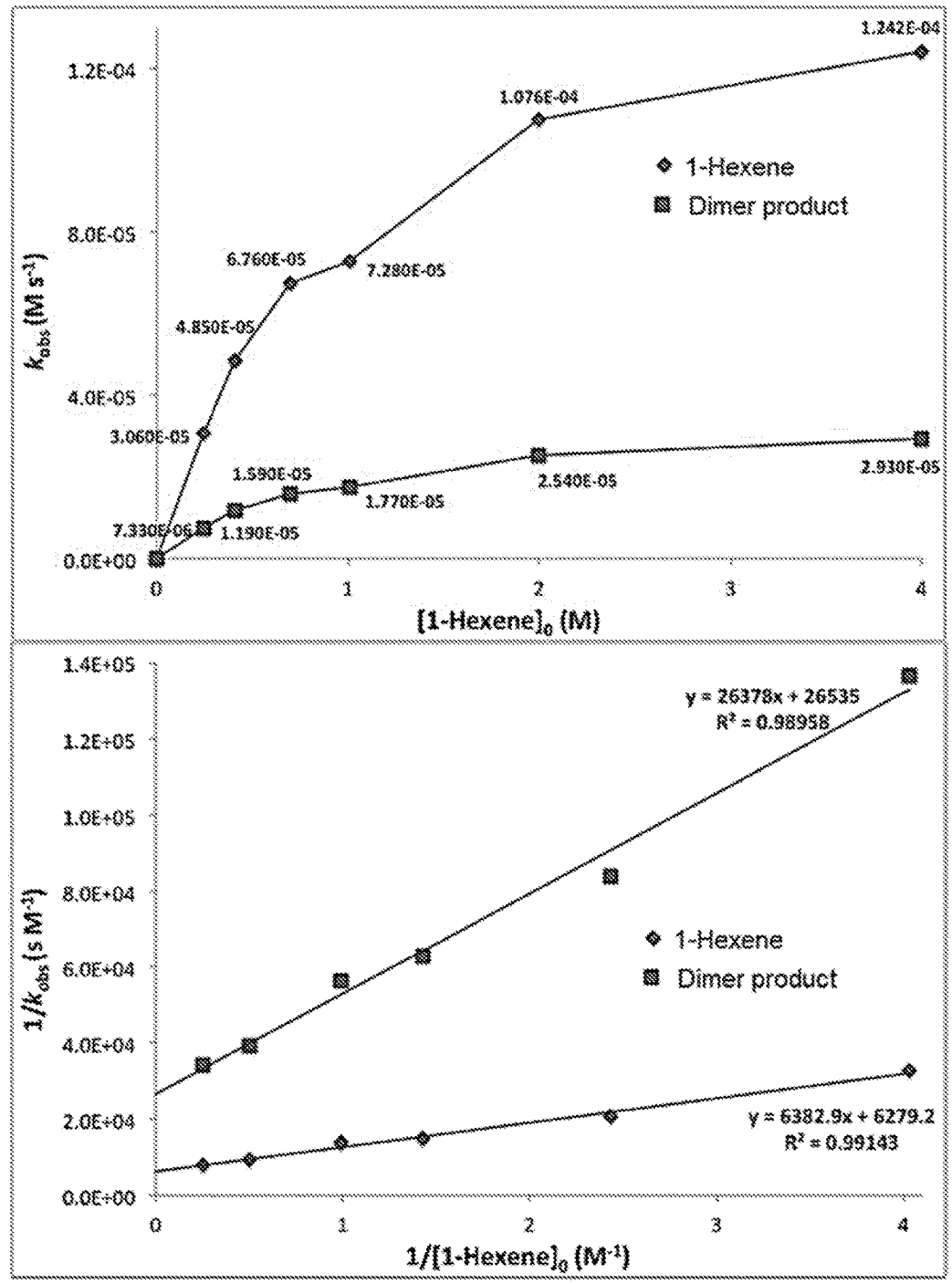

FIG. 14. Initial rate of 1-hexene dimerization as a function of $[1\text{-hexene}]_0$ at 80° C. Top: Rate vs. concentration. Bottom: Double reciprocal plot. Legend: diamond, 1-hexene; square, dimer product.

Figure 15:
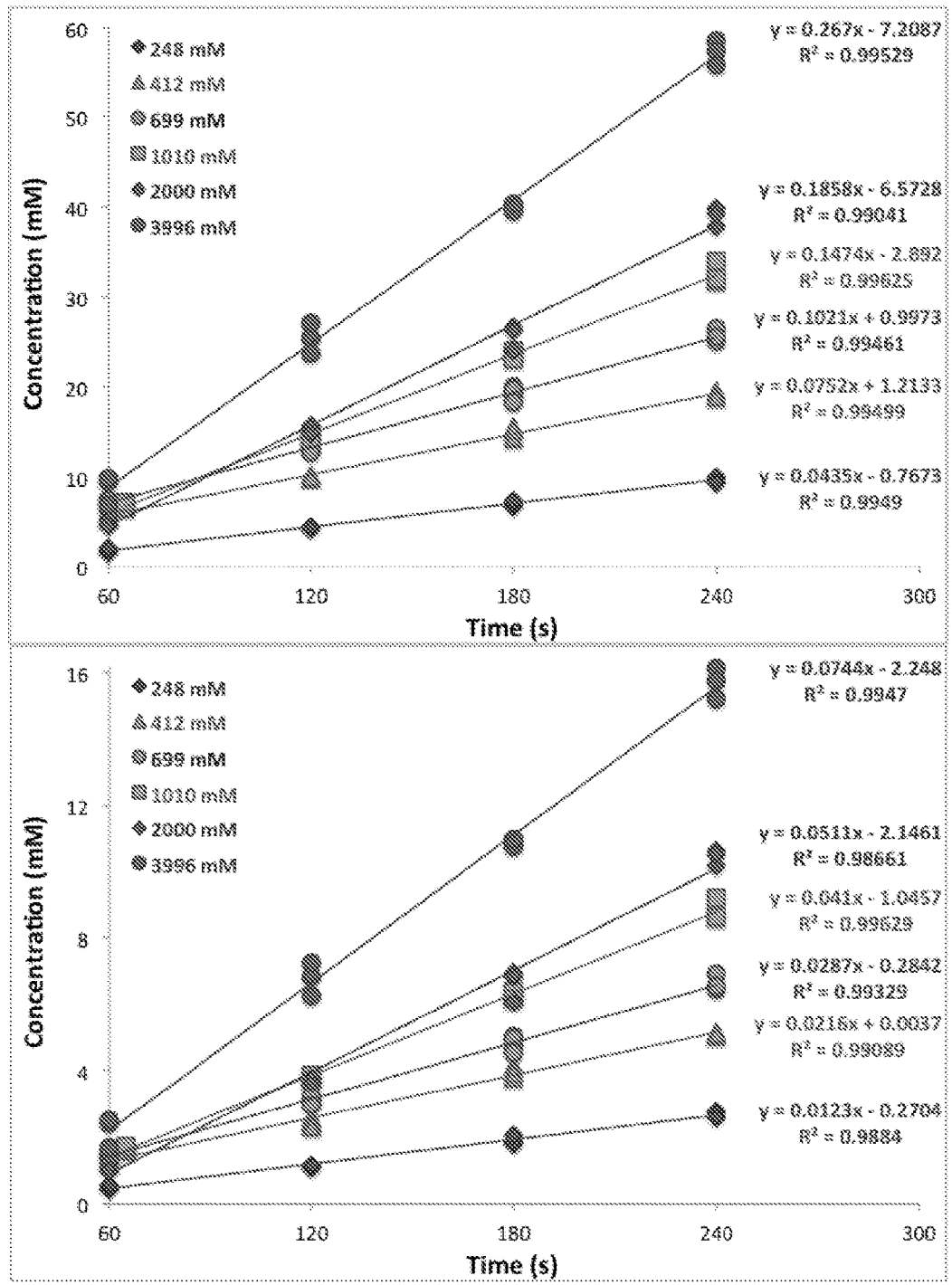

FIG. 15. Initial rate measurements for 1-hexene dimerization at 90° C. Top: Major isomer product. Bottom: Minor isomer product. Legend: diamond, 1-hexene; square, dimer product.

Figure 16:
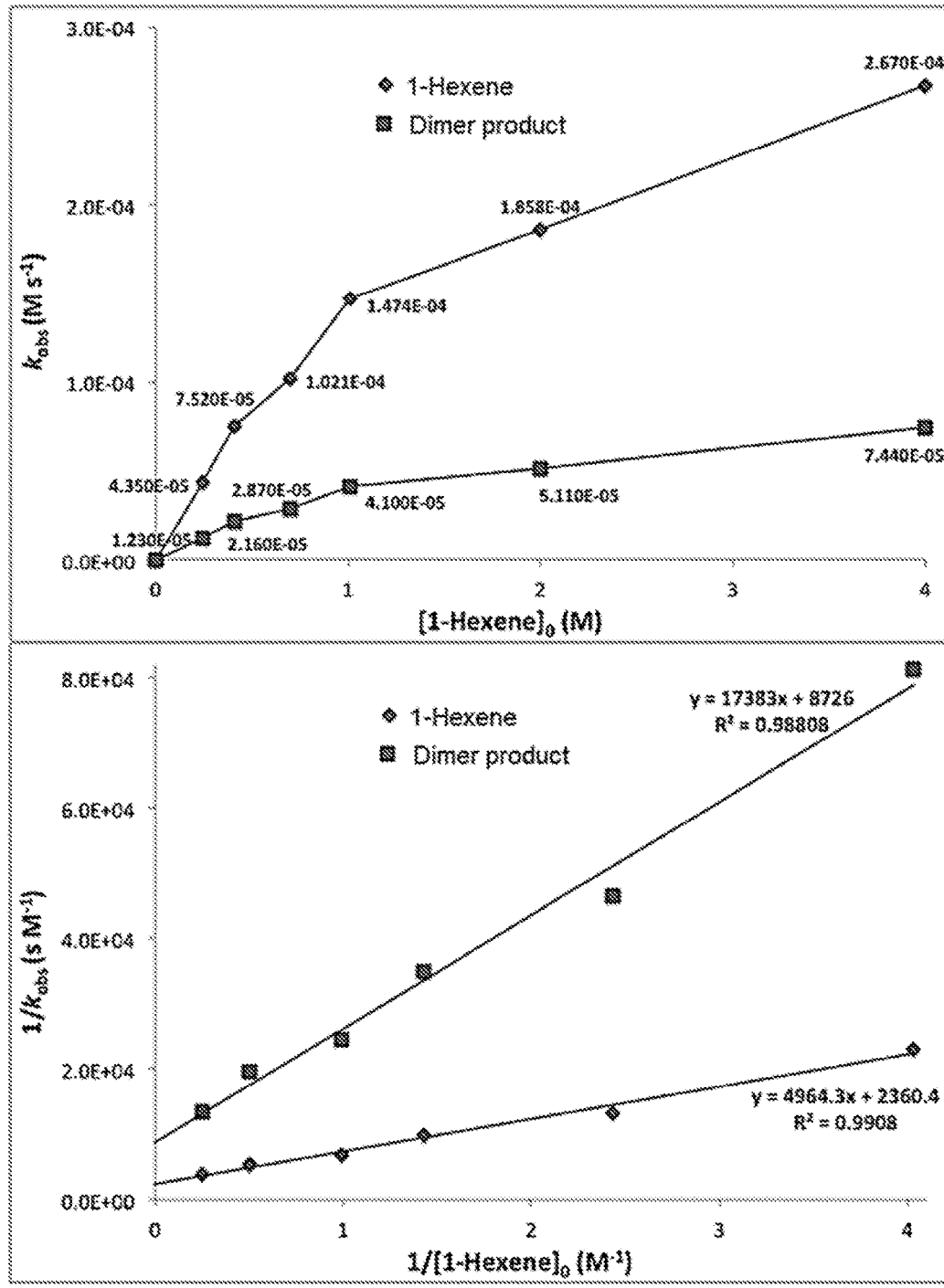

FIG. 16. Initial rate of 1-hexene dimerization as a function of $[1\text{-hexene}]_0$ at 90° C. Top: Rate vs. concentration. Bottom: Double reciprocal plot. Legend: diamond, 1-hexene; square, dimer product.

Figure 17:
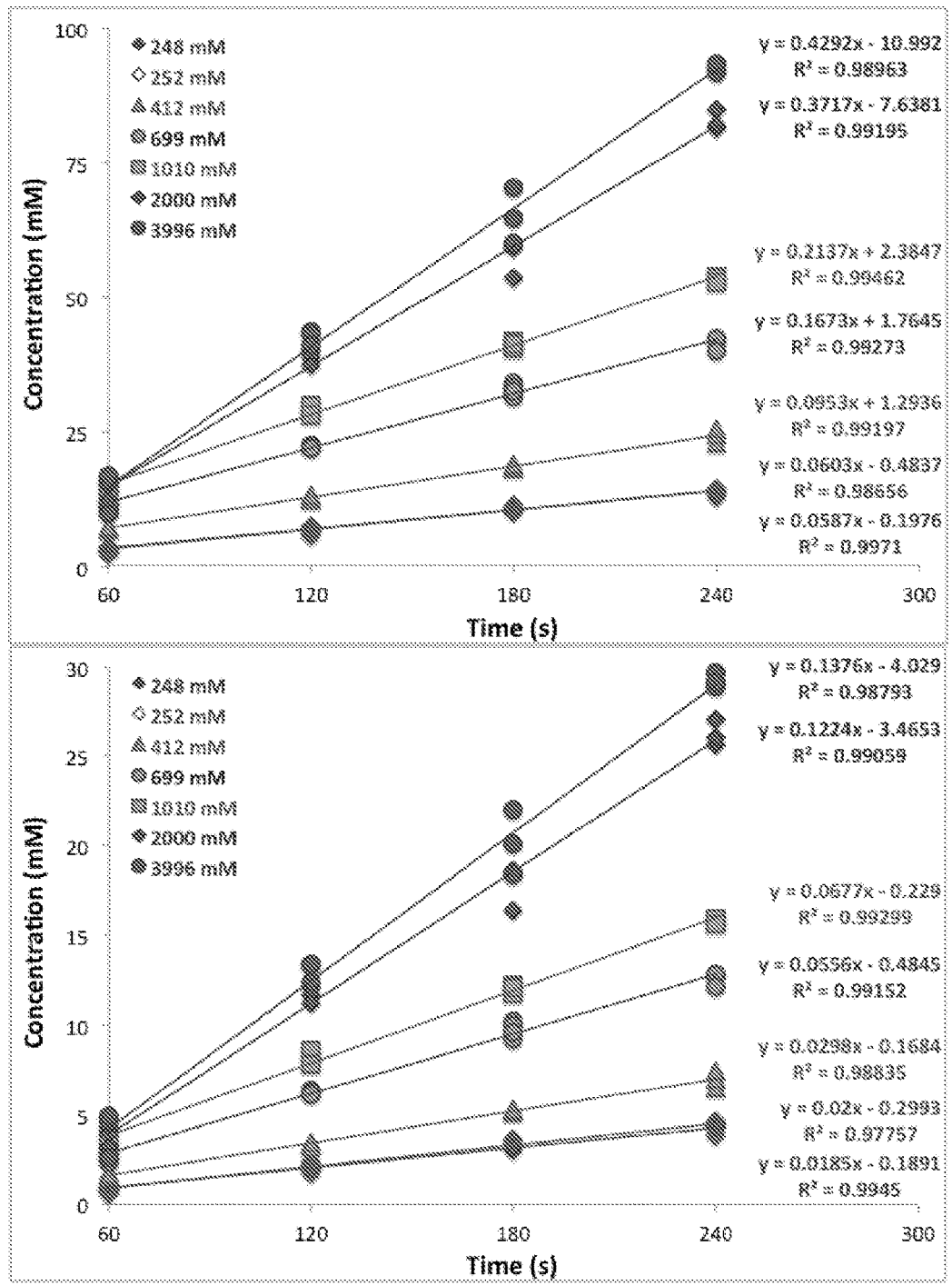

FIG. 17. Initial rate measurements for 1-hexene dimerization at 100° C. Top: Major isomer product. Bottom: Minor isomer product. Legend: diamond, 1-hexene; square, dimer product.

Figure 18:
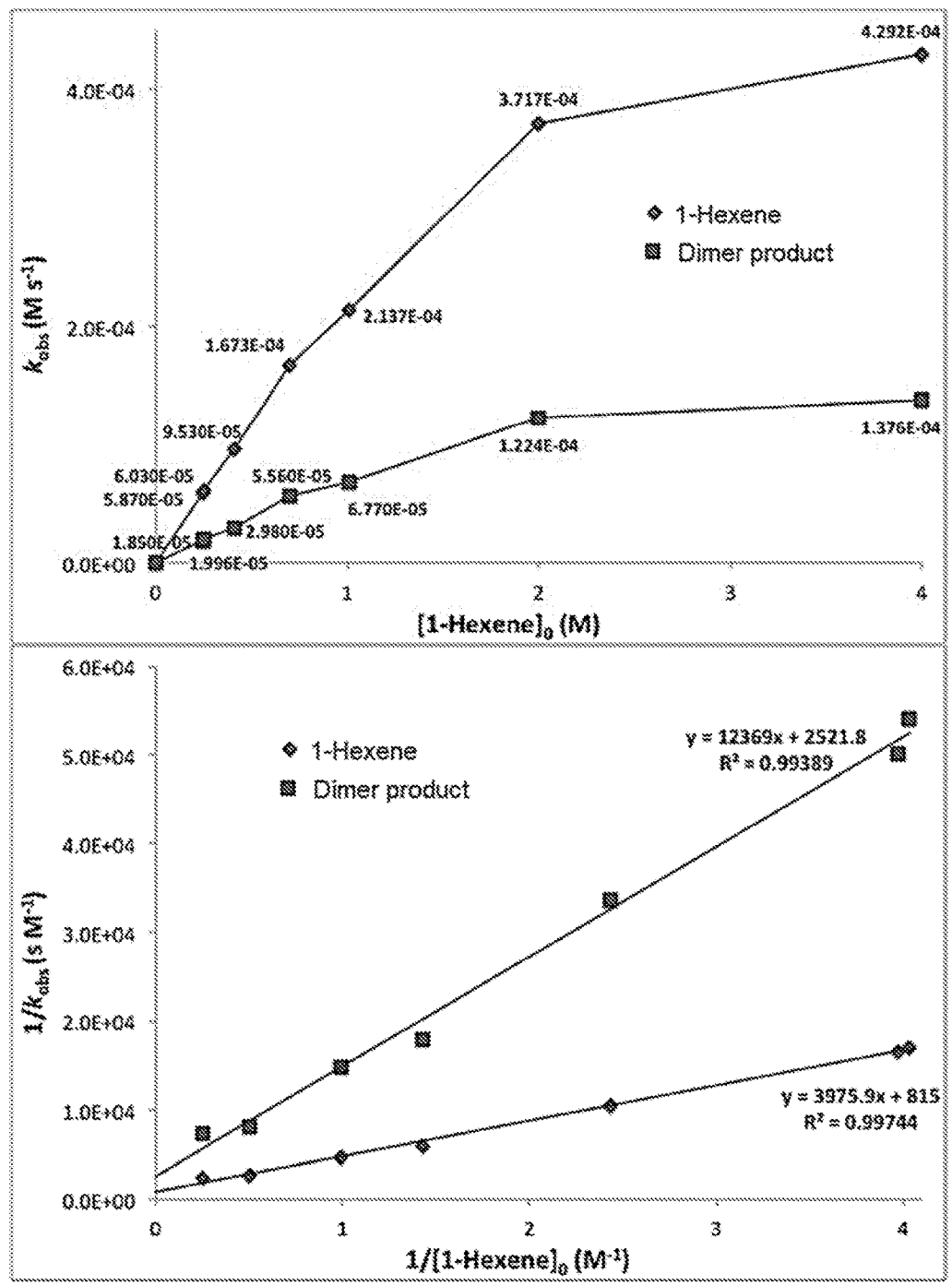

FIG. 18. Initial rate of 1-hexene dimerization as a function of $[1\text{-hexene}]_0$ at 100° C. Top: Rate vs. concentration. Bottom: Double reciprocal plot. Legend: diamond, 1-hexene; square, dimer product.

Figure 19:
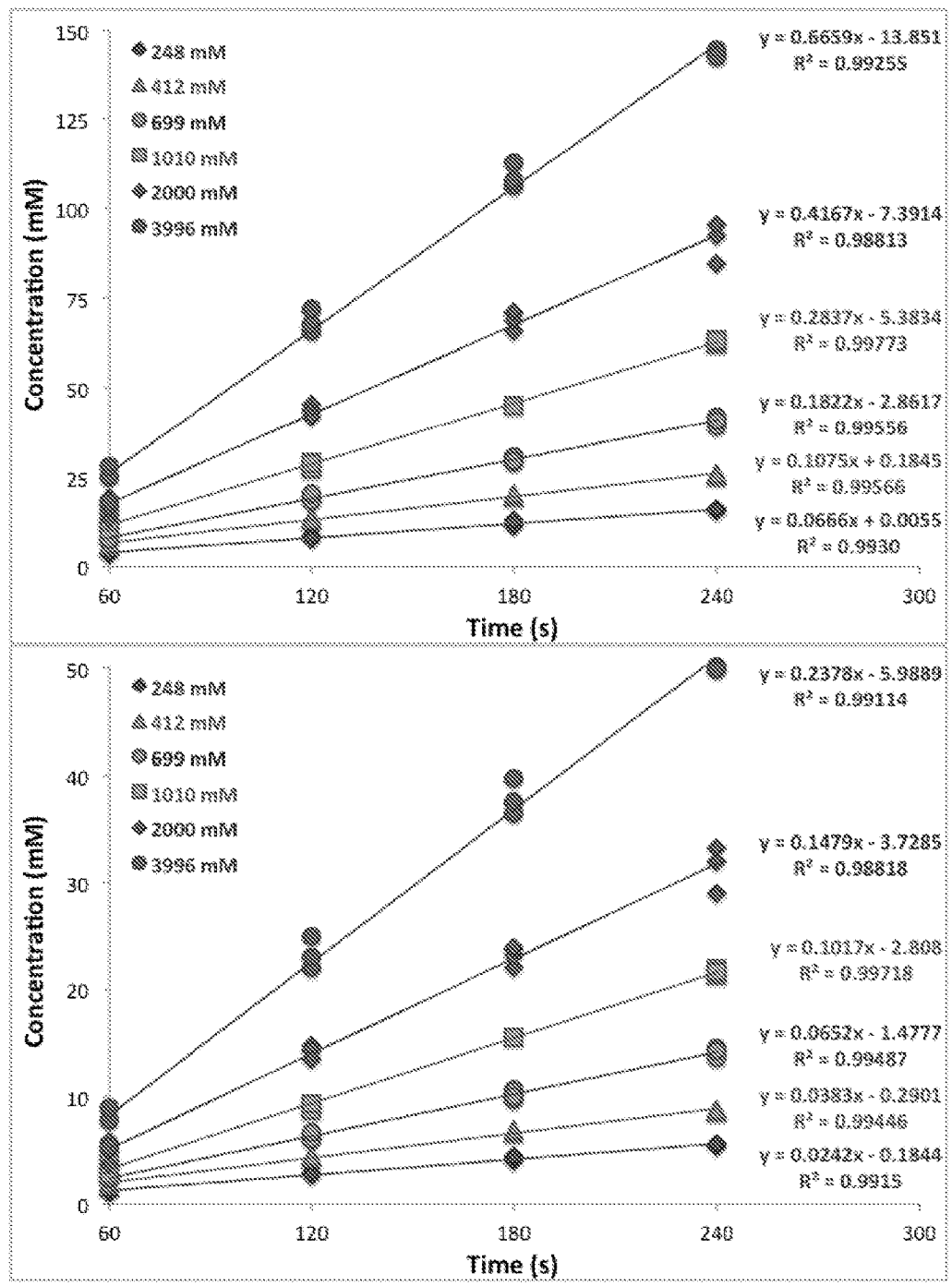

FIG. 19. Initial rate measurements for 1-hexene dimerization at 110° C. Top: Major isomer product. Bottom: Minor isomer product. Legend: diamond, 1-hexene; square, dimer product.

Figure 20:
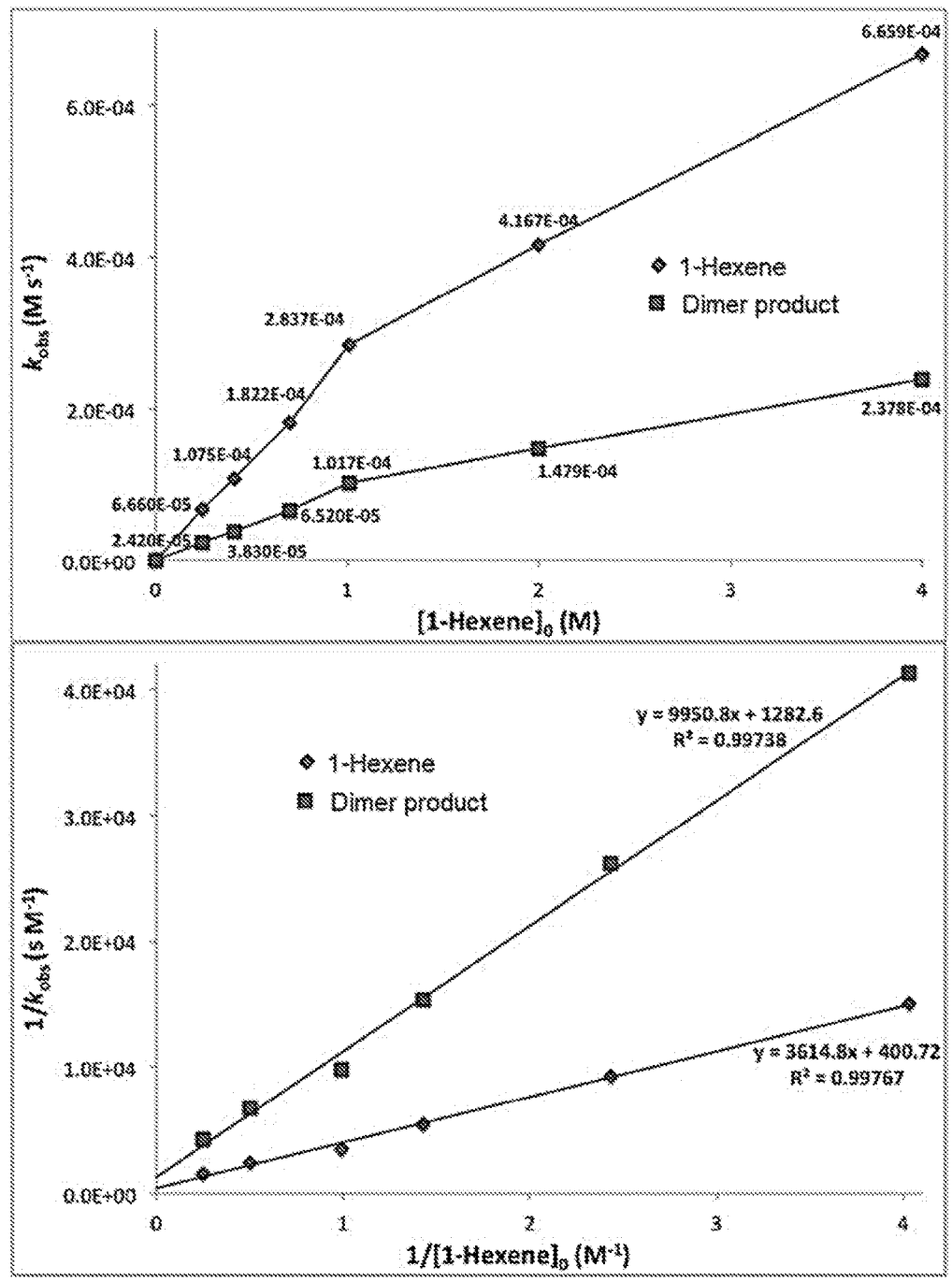

FIG. 20. Initial rate of 1-hexene dimerization as a function of $[1\text{-hexene}]_0$ at 110° C. Top: Rate vs. concentration. Bottom: Double reciprocal plot. Legend: diamond, 1-hexene; square, dimer product. Legend: diamond, 1-hexene; square, dimer product.

Figure 21:
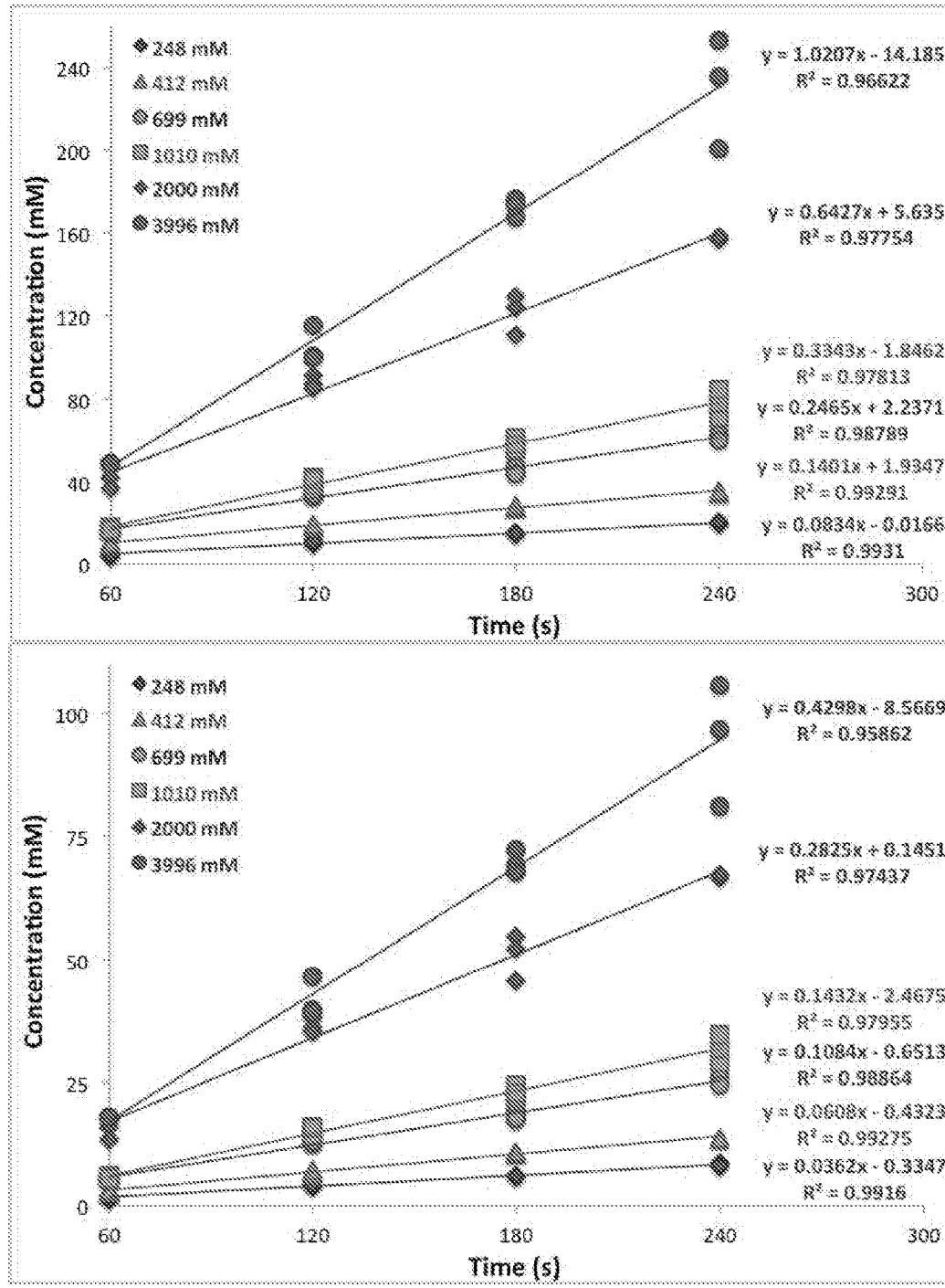

FIG. 21. Initial rate measurements for 1-hexene dimerization at 125° C. Top: Major isomer product. Bottom: Minor isomer product. Legend: diamond, 1-hexene; square, dimer product.

Figure 22:
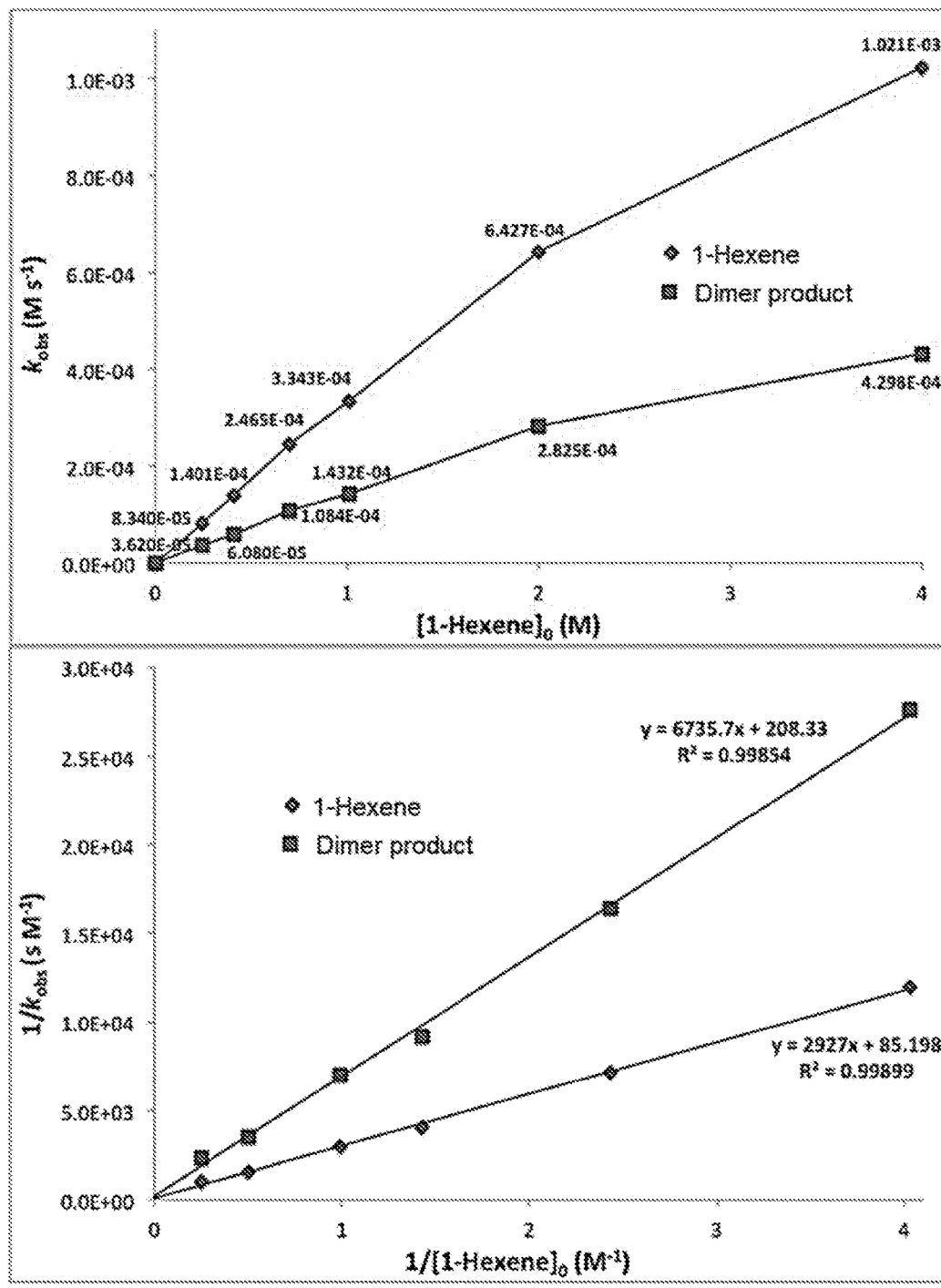

FIG. 22. Initial rate of 1-hexene dimerization as a function of $[1\text{-hexene}]_0$ at 125° C. Top: Rate vs. concentration. Bottom: Double reciprocal plot. Legend: diamond, 1-hexene; square, dimer product.

Figure 23:
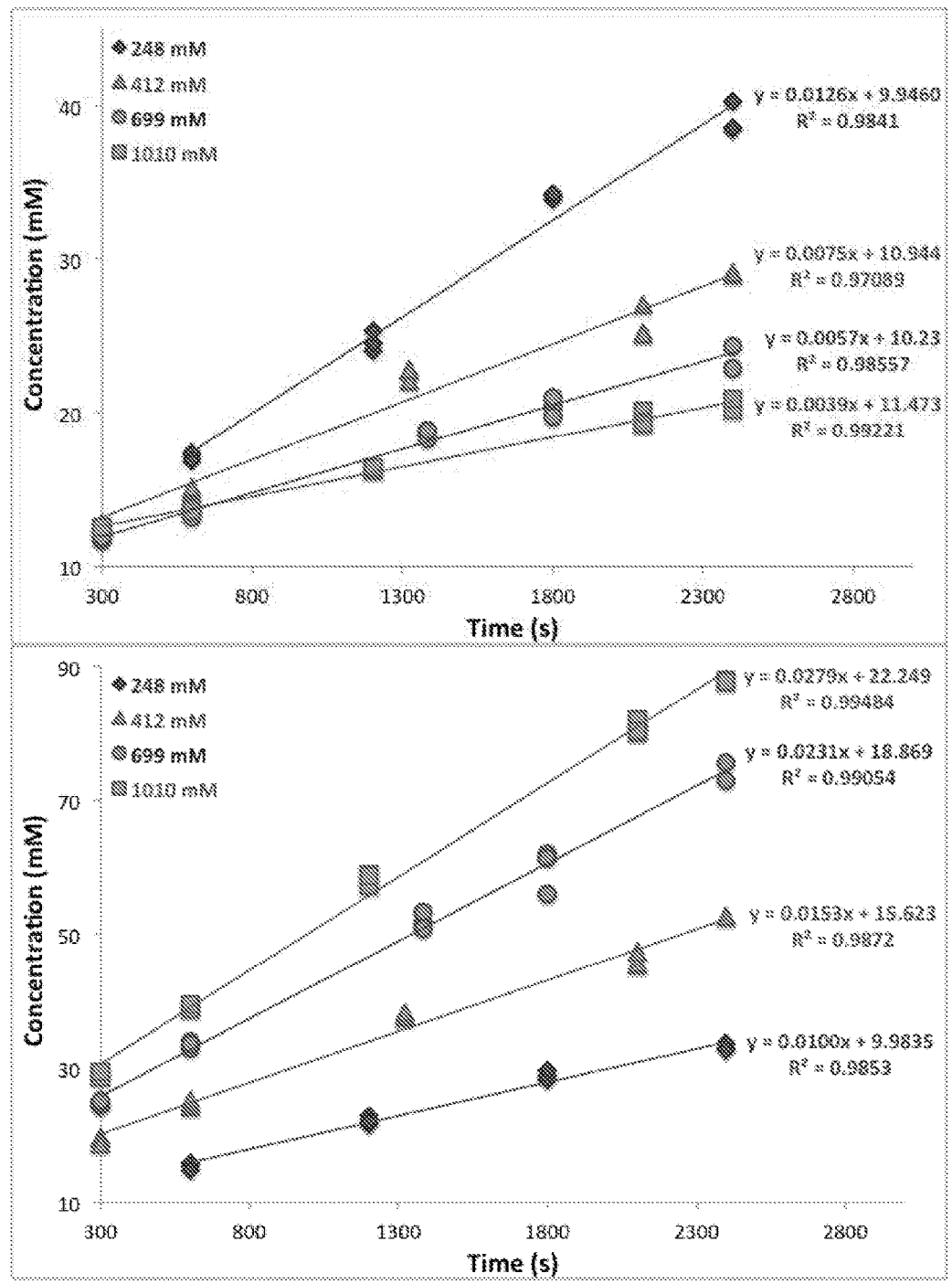

FIG. 23. Initial rate measurements for 1-hexene/n-decane transfer hydrogenation at 100° C. Top: n-Hexane formation (hydrogenation). Bottom: 2-Hexenes formation (isomerization).

Figure 24:
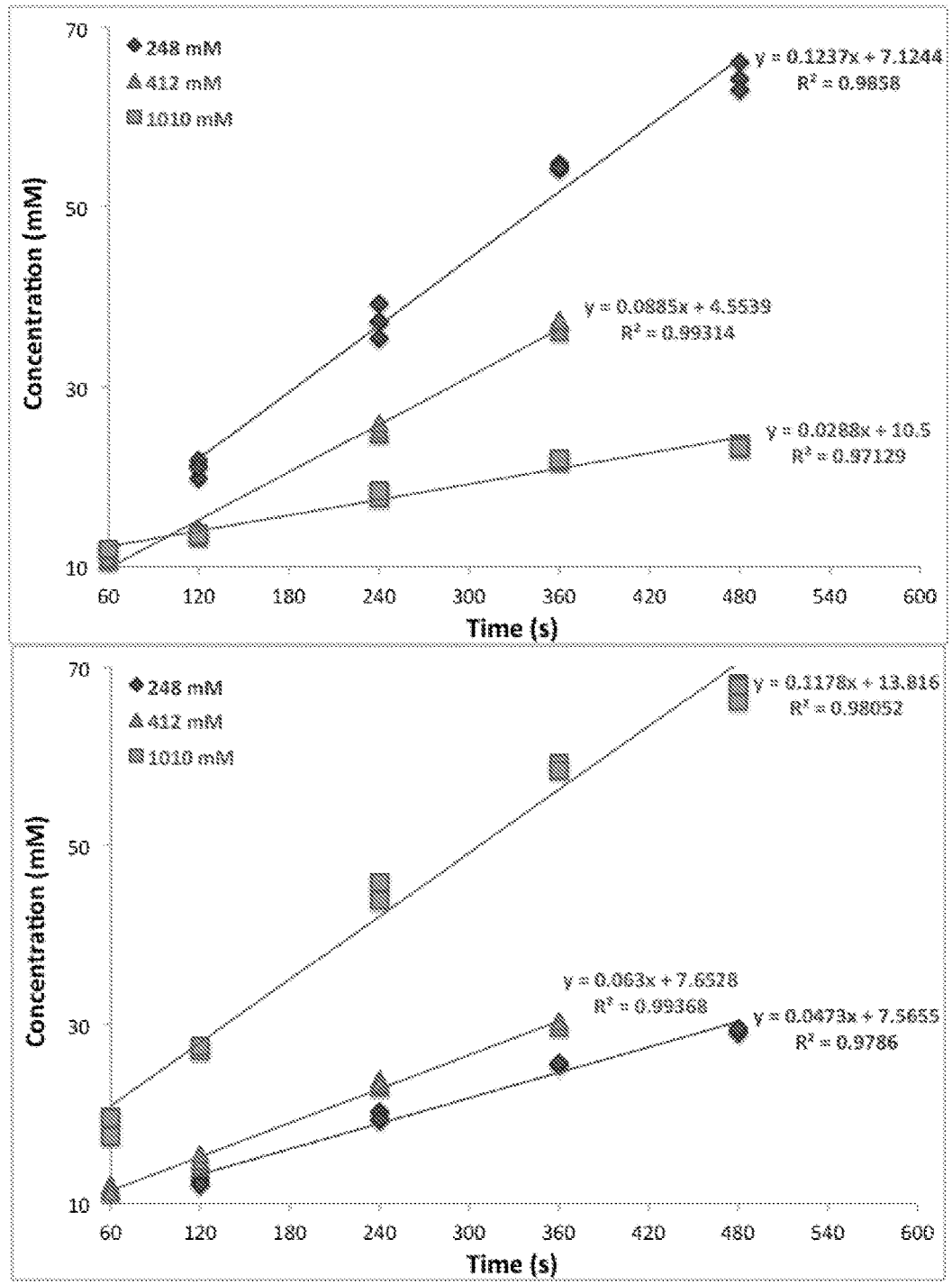

FIG. 24. Initial rate measurements for 1-hexene/n-decane transfer hydrogenation at 125° C. Top: n-Hexane formation (hydrogenation). Bottom: 2-Hexenes formation (isomerization).

Figure 25:
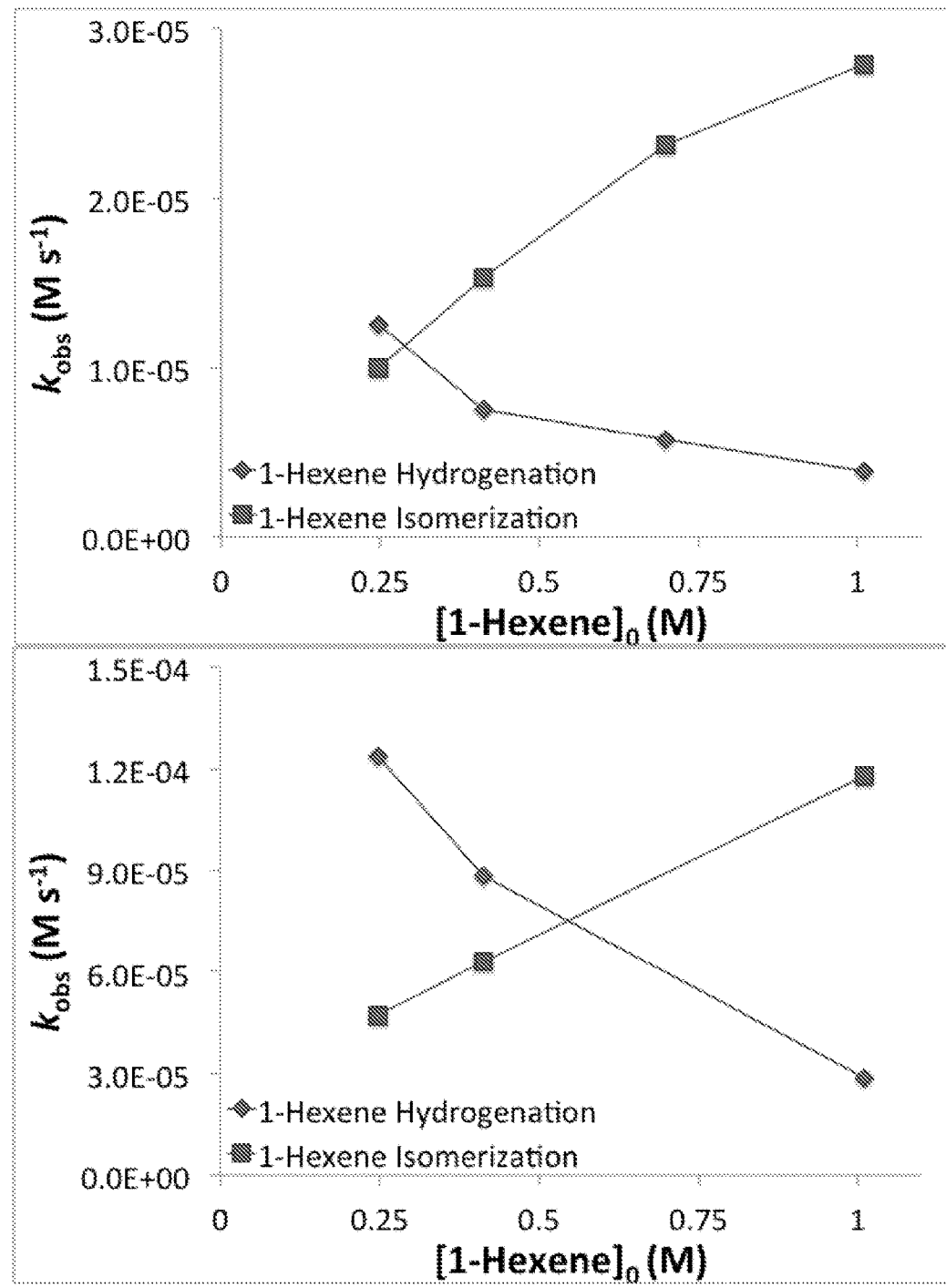

FIG. 25. Initial rate of 1-hexene hydrogenation and isomerization by 2 (5 mM) versus $[1\text{-hexene}]_0$. Top: 100° C. Bottom: 125° C.

Figure 26:
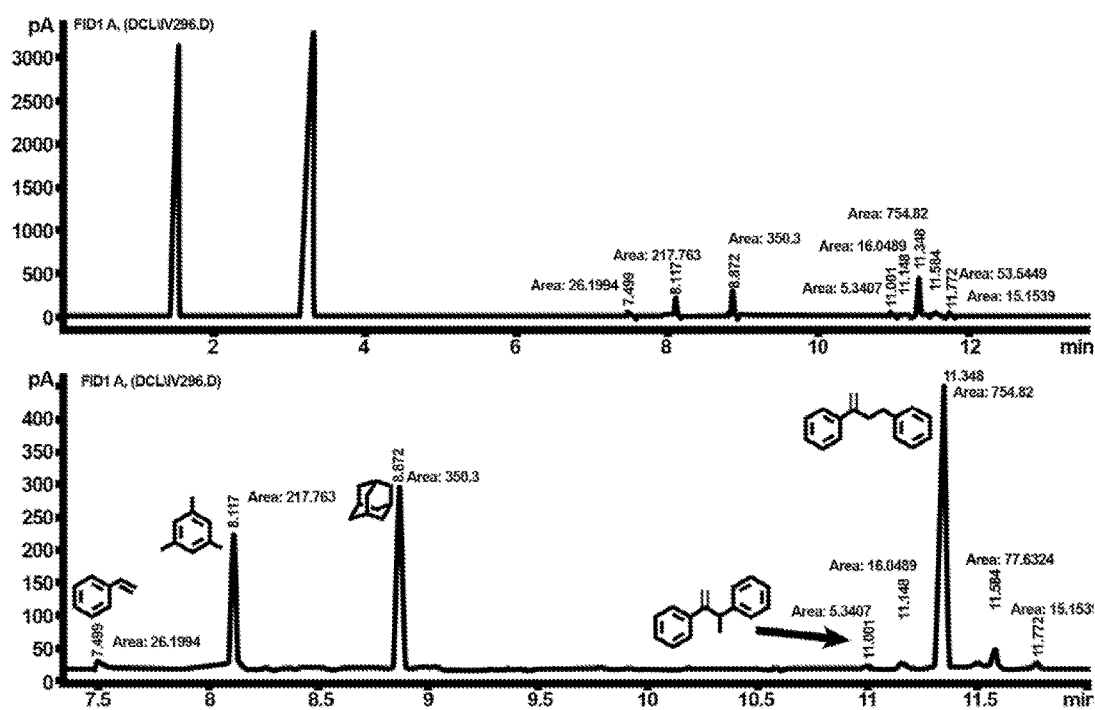

FIG. 26. GC trace of styrene (500 mM) dimerization by 1 (25 mM), 110° C., 72 h.

Figure 27:
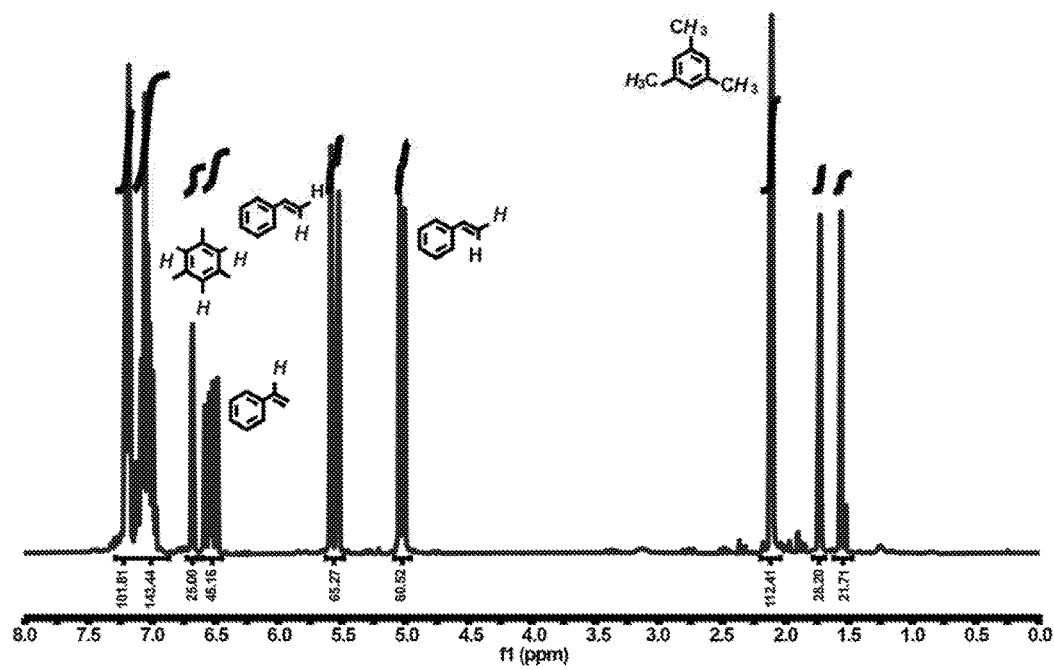

FIG. 27. Initial $^1$H NMR spectrum of styrene (500 mM) dimerization by 1.

Figure 28:
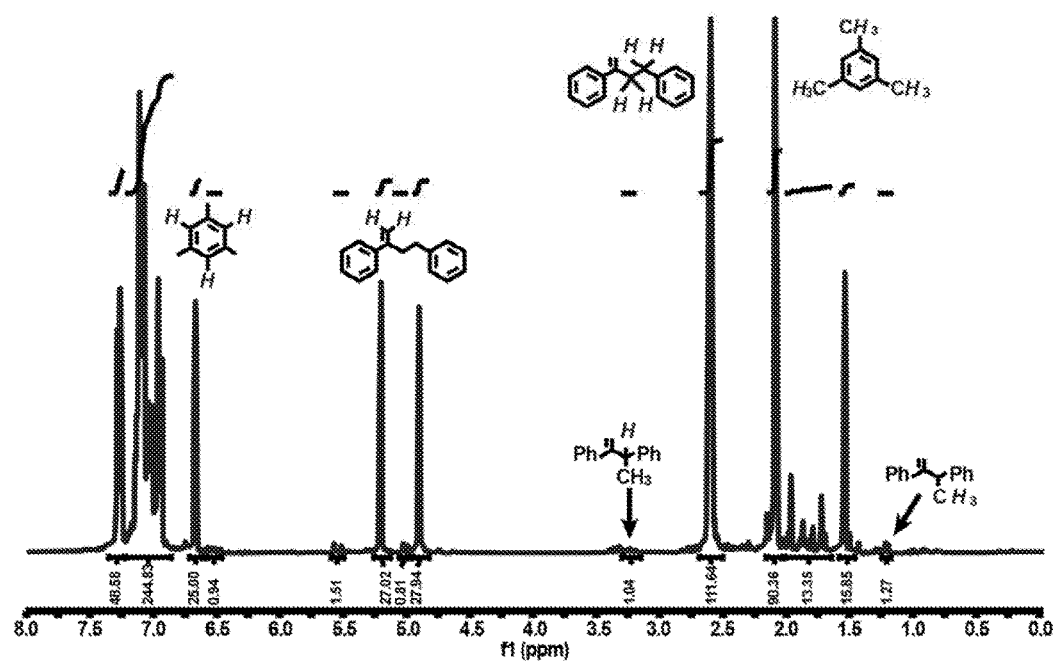

FIG. 28. $^1$H NMR spectrum of styrene (500 mM) dimerization by 1 (25 mM), 110° C., 72 h.

Figure 29:
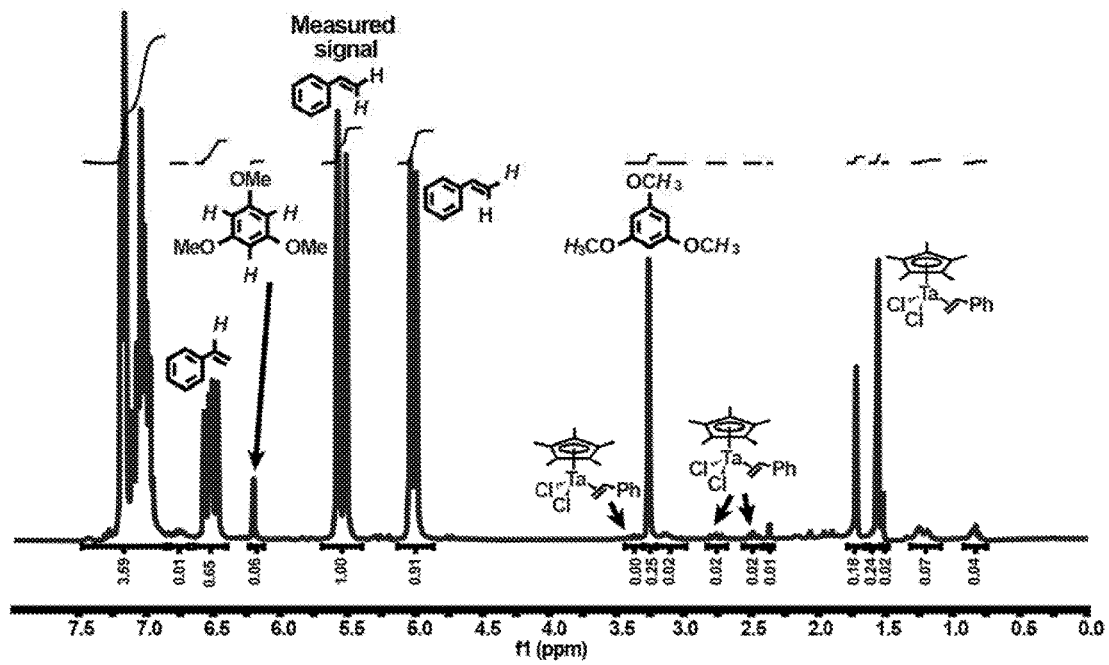

FIG. 29. $^1$H NMR spectrum of the dimerization of styrene with 1 (t=0 h, initial).

Figure 30:
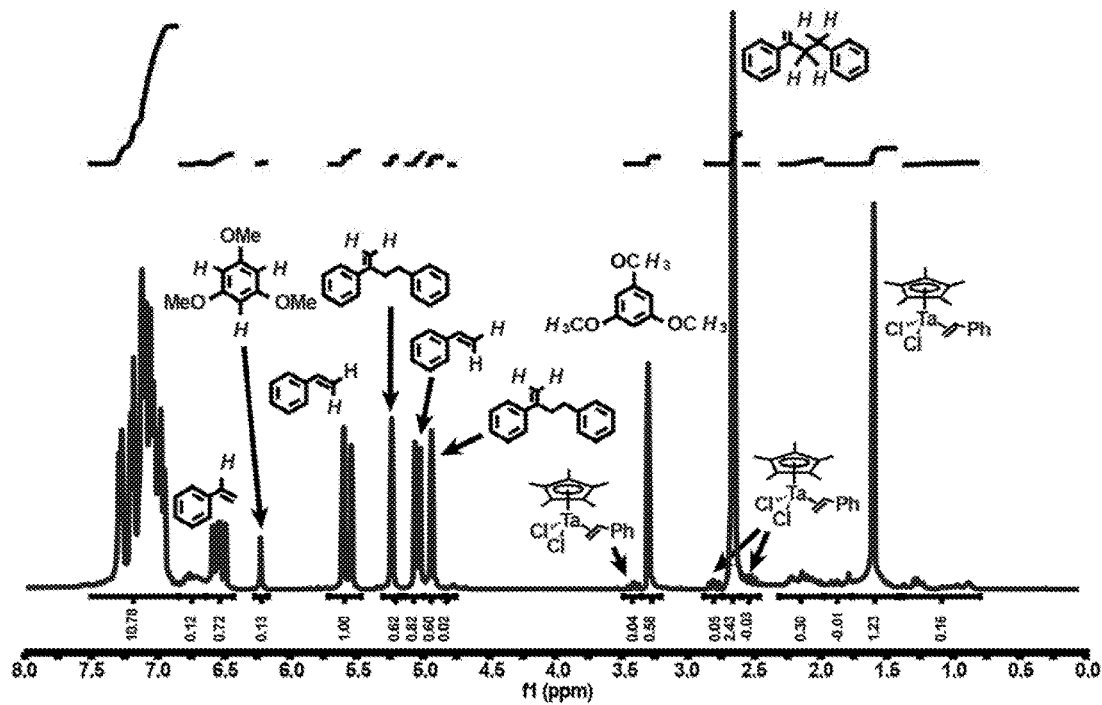

FIG. 30. $^1$H NMR spectrum of the dimerization of styrene with 1 (t=42 h, ~50%).

Figure 31:
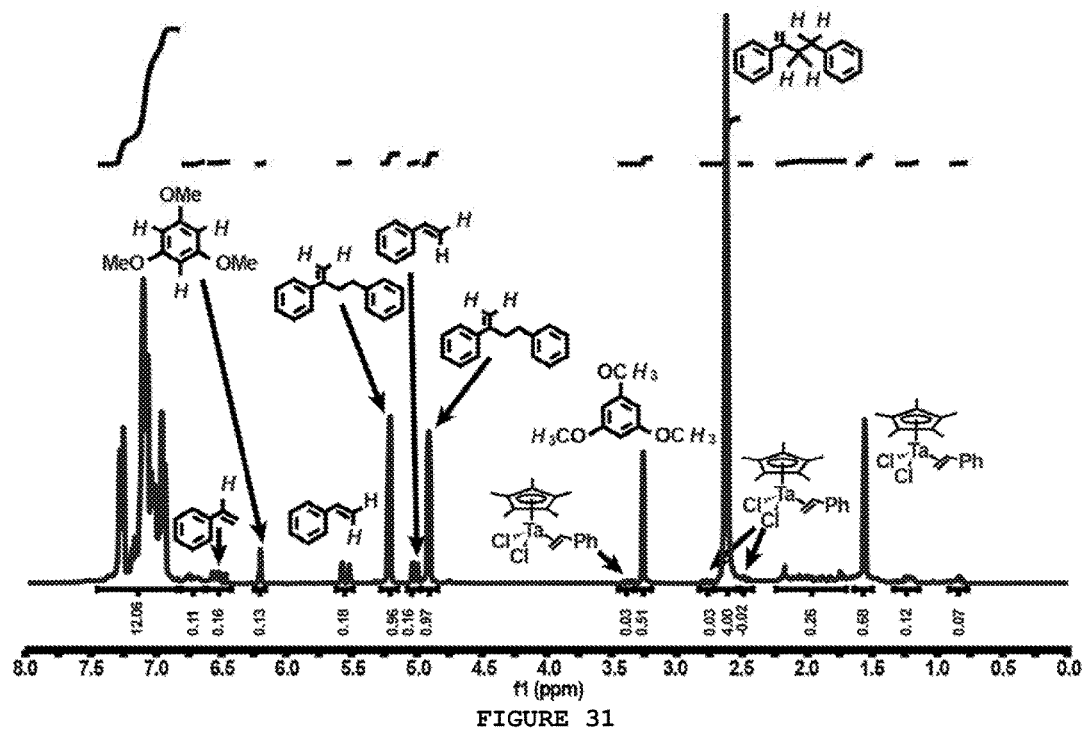

FIG. 31. $^1$H NMR spectrum of the dimerization of styrene with 1 (t=160 h, final point).

Figure 32:
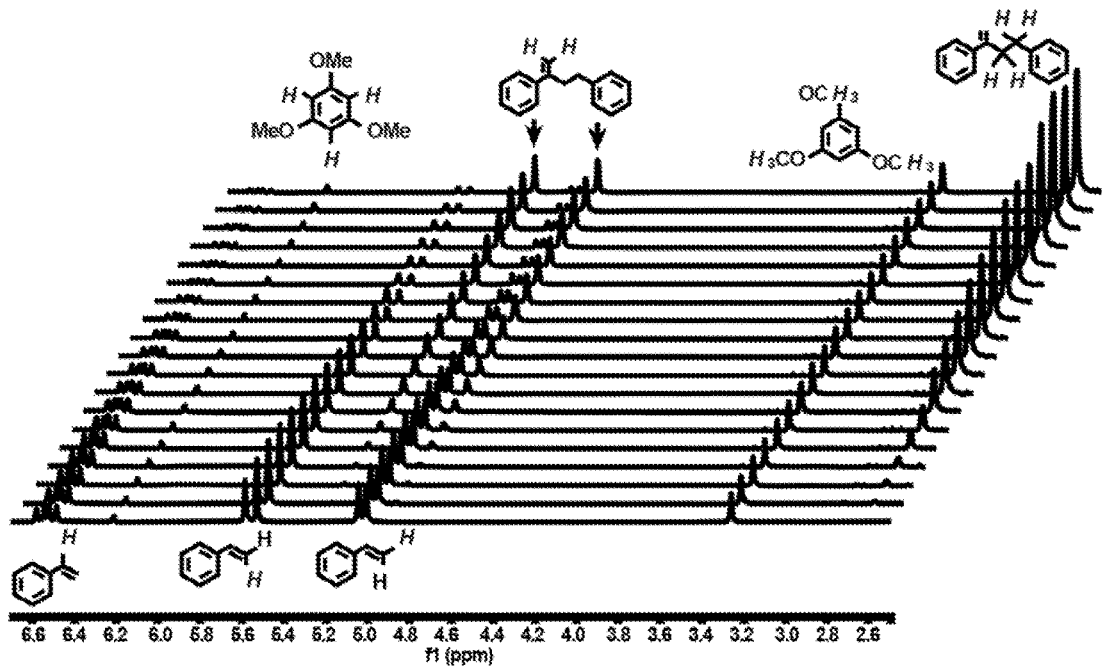

FIG. 32. Stack plot of $^1$H NMR spectra (2.5-6.7 ppm) for styrene dimerization catalyzed by 1 at 100° C. Nineteen spectra were taken at the following time points: 0, 1, 2, 4, 7, 10, 18, 24, 32, 42, 52, 64, 72, 88, 97, 109, 119, 134, and 160 hours (t=0 h at bottom).

Figure 33:
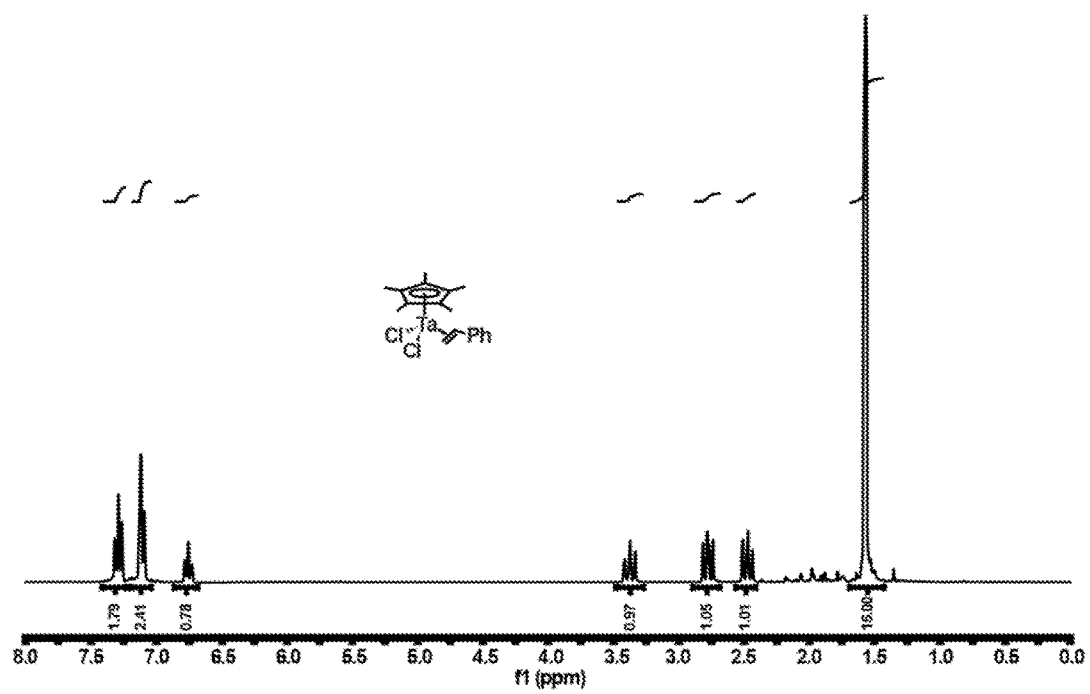

FIG. 33. $^1$H NMR spectrum of Cp*TaCl$_2$(styrene)$^3$ in $C_6D_6$, establishing chemical shifts for comparison to catalytic runs.

Figure 34:
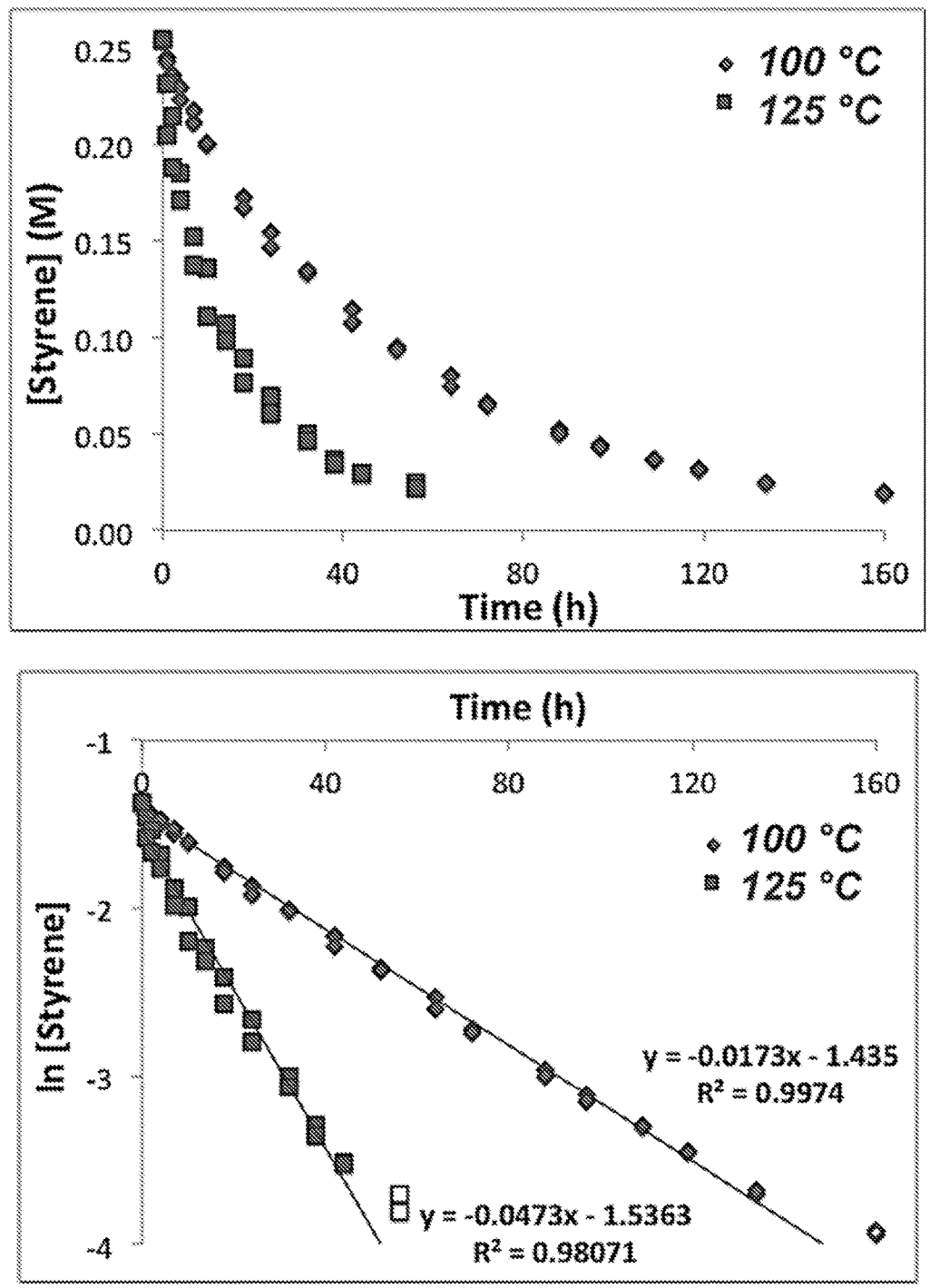

FIG. 34. Consumption of styrene during dimerization catalyzed by 1 at 100° C. and 125° C. monitored by $^1$H NMR spectroscopy (two runs). Top: Conc. plot. Bottom: ln plot. Legend: diamond, concentration of styrene at 100° C.; square, concentration of styrene at 125° C.

Figure 35:
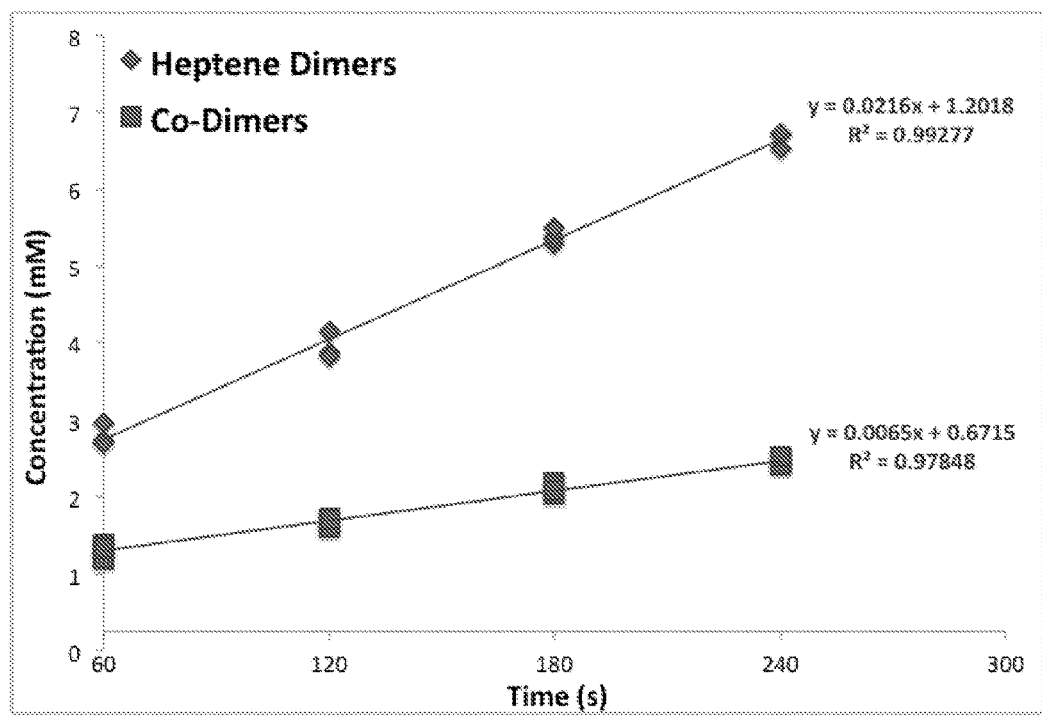

FIG. 35. Initial rates of styrene/1-heptene co-dimerization with 1. Data for each time point was collected from 3 different vials, giving 12 data points for each initial rate determination.

Figure 36:
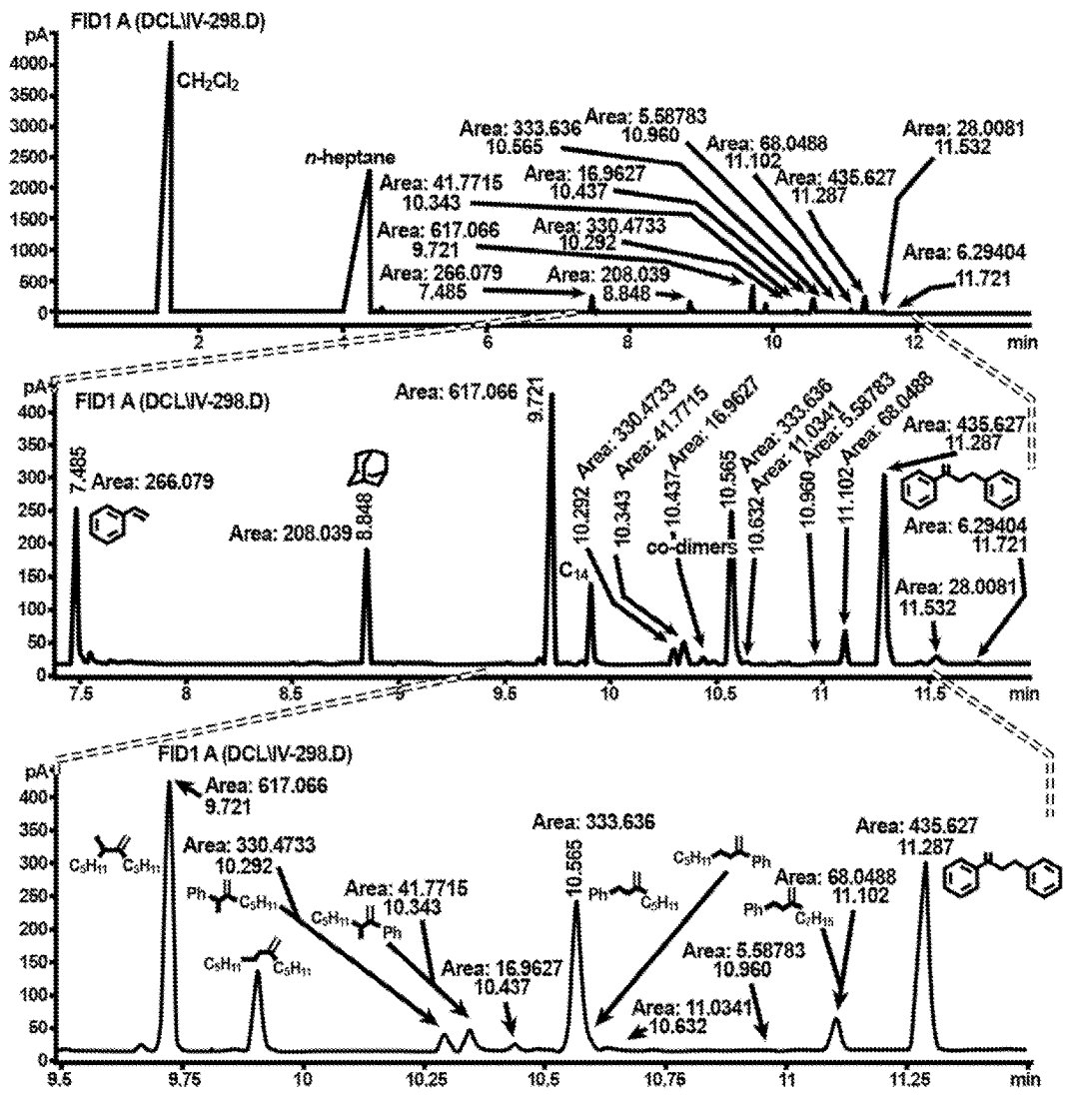

FIG. 36. GC trace of the co-dimerization of styrene (250 mM) and 1-heptene (250 mM) with 1 (25 mM) to produce co-dimers. The $C_{14}$ products (1-heptene dimers) are assigned based upon the work of McLain et al. (*J. Am. Chem. Soc.* 102:5610 (1980)); the co-dimers are assigned based on GC/MS and comparison to authentic samples of three of the proposed compounds (vide infra). The styrene/1-nonane co-dimer (peak at 11.102 min) is assigned based on GC/MS, and its regiochemistry by analogy to the major isomer of the styrene/1-heptene co-dimers. The 1-nonane is presumably generated from coupling 1-heptene and ethylene (from 1).

Figure 37:
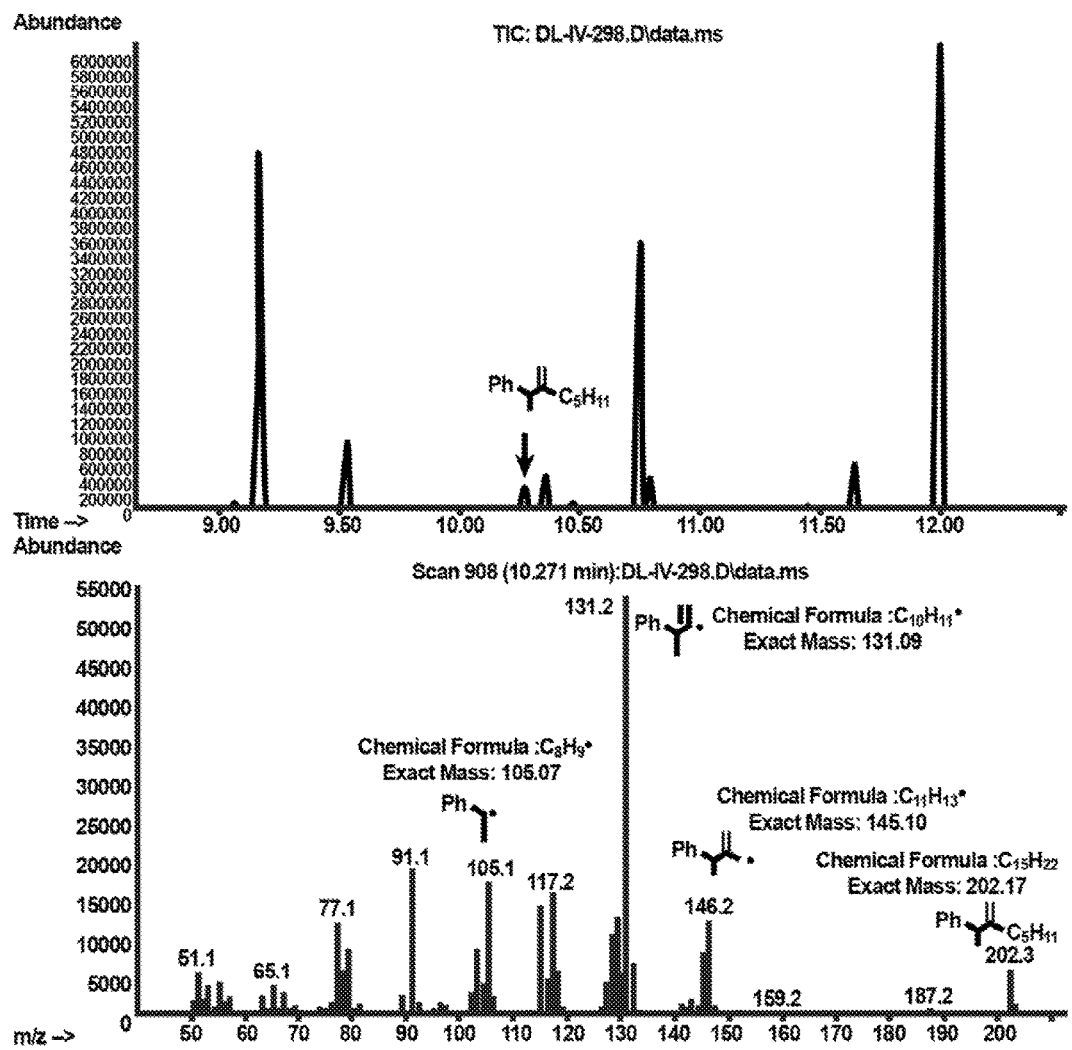

FIG. 37. GC/MS trace of the co-dimerization of styrene (250 mM) and 1-heptene (250 mM) with 1 (25 mM) to produce co-dimers. Mass spectrum corresponds to indicated peak.

Figure 38:
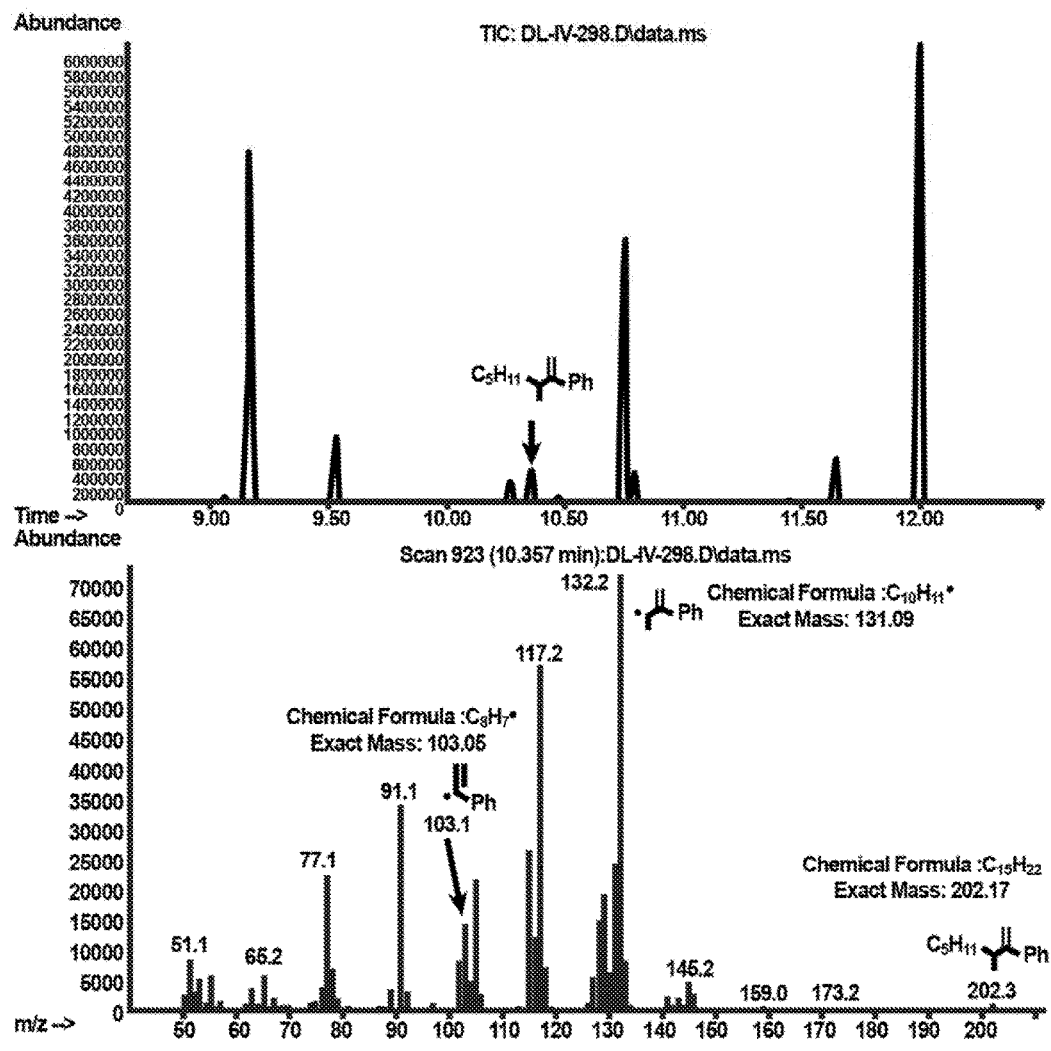

FIG. 38. GC/MS trace of the co-dimerization of styrene (250 mM) and 1-heptene (250 mM) with 1 (25 mM) to produce co-dimers. Mass spectrum corresponds to indicated peak.

Figure 39:
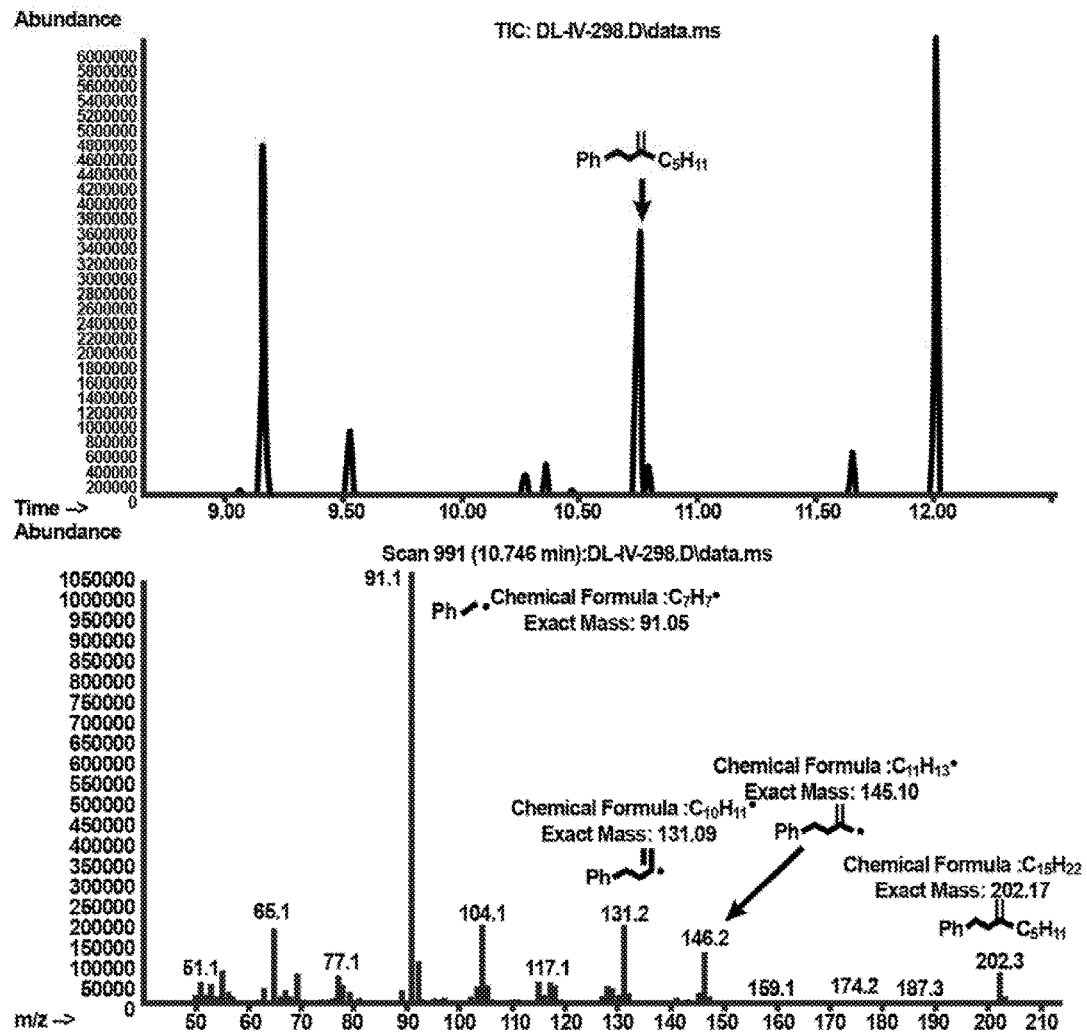

FIG. 39. GC/MS trace of the co-dimerization of styrene (250 mM) and 1-heptene (250 mM) with 1 (25 mM) to produce co-dimers. Mass spectrum corresponds to indicated peak.

Figure 40:
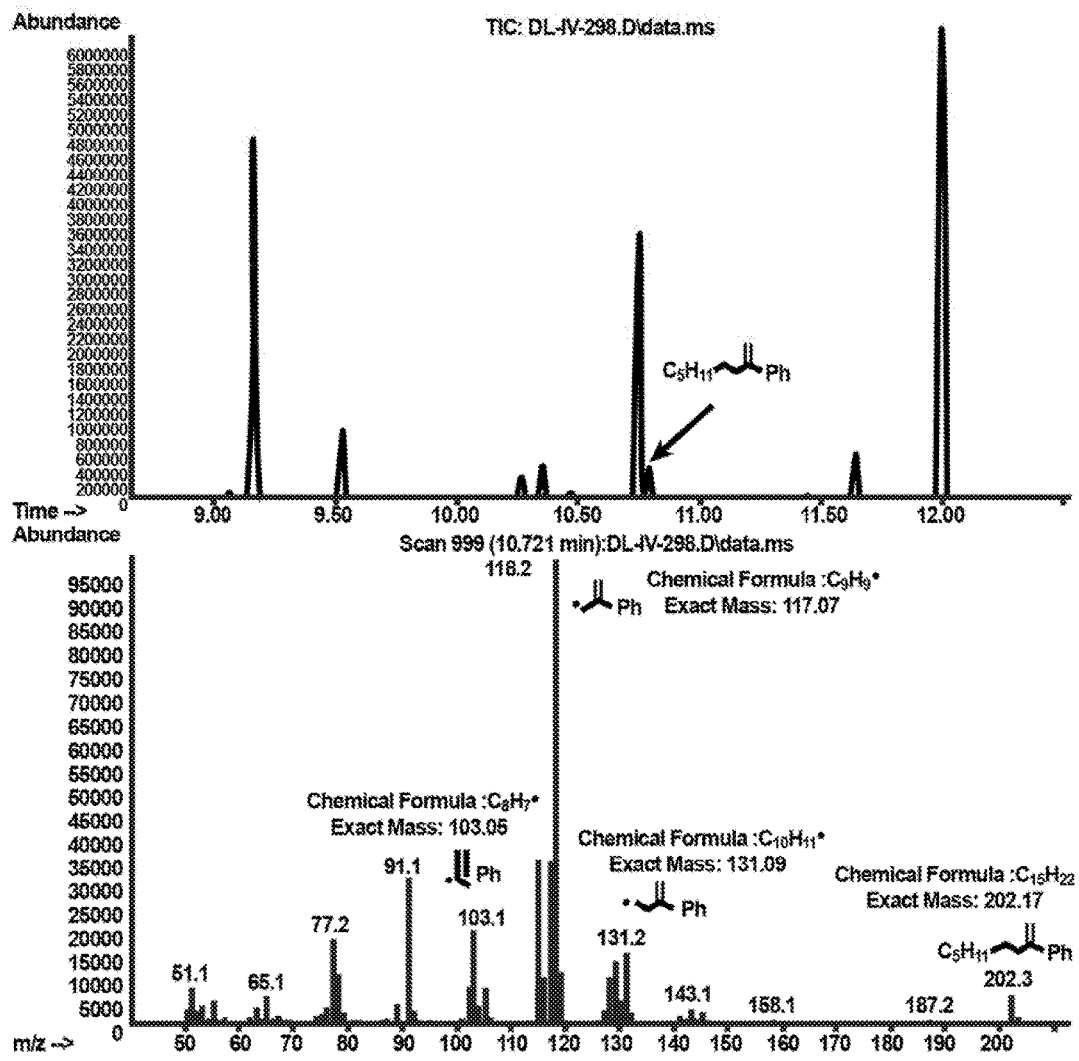

FIG. 40. GC/MS trace of the co-dimerization of styrene (250 mM) and 1-heptene (250 mM) with 1 (25 mM) to produce co-dimers. Mass spectrum corresponds to indicated peak.

Figure 41:
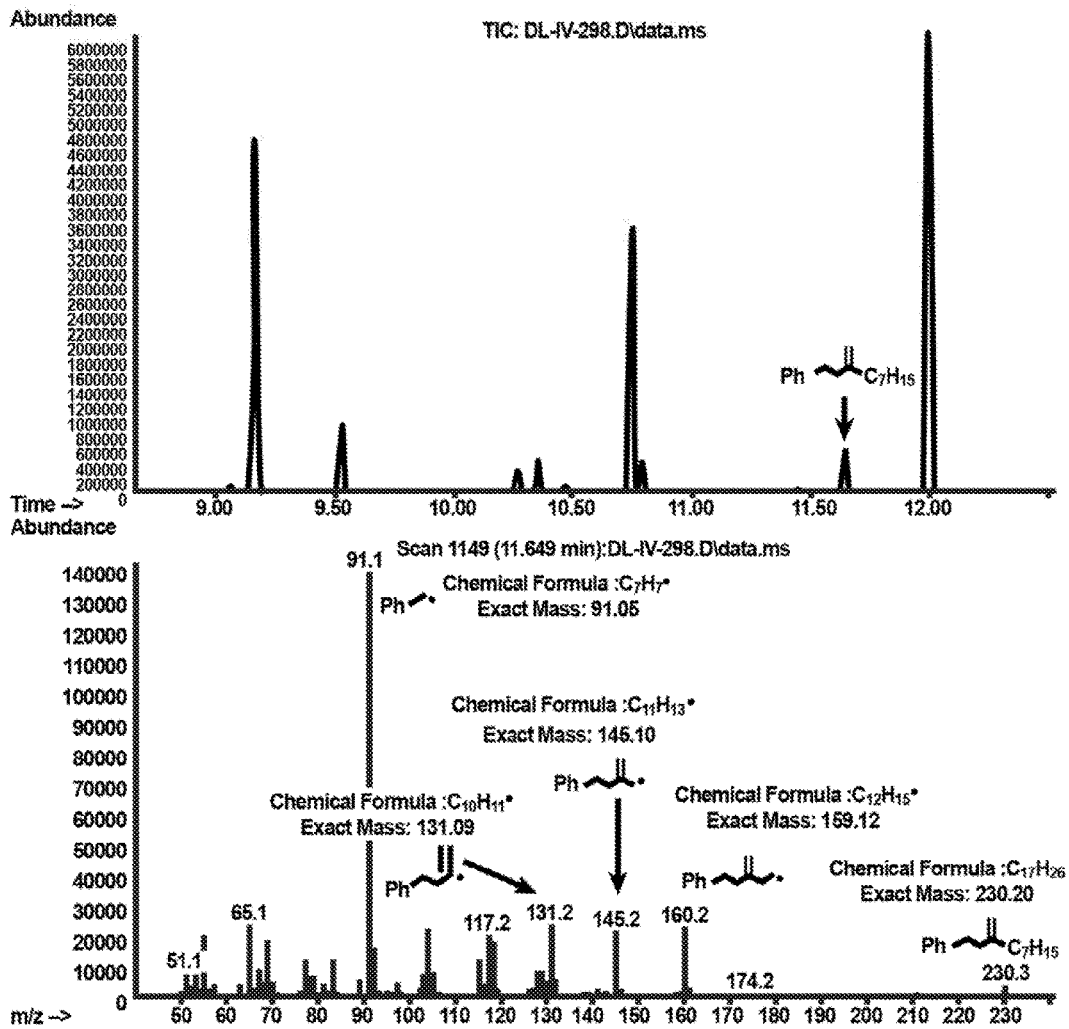

FIG. 41. GC/MS trace of the co-dimerization of styrene (250 mM) and 1-heptene (250 mM) with 1 (25 mM) to produce co-dimers. Mass spectrum corresponds to indicated peak.

Figure 42:
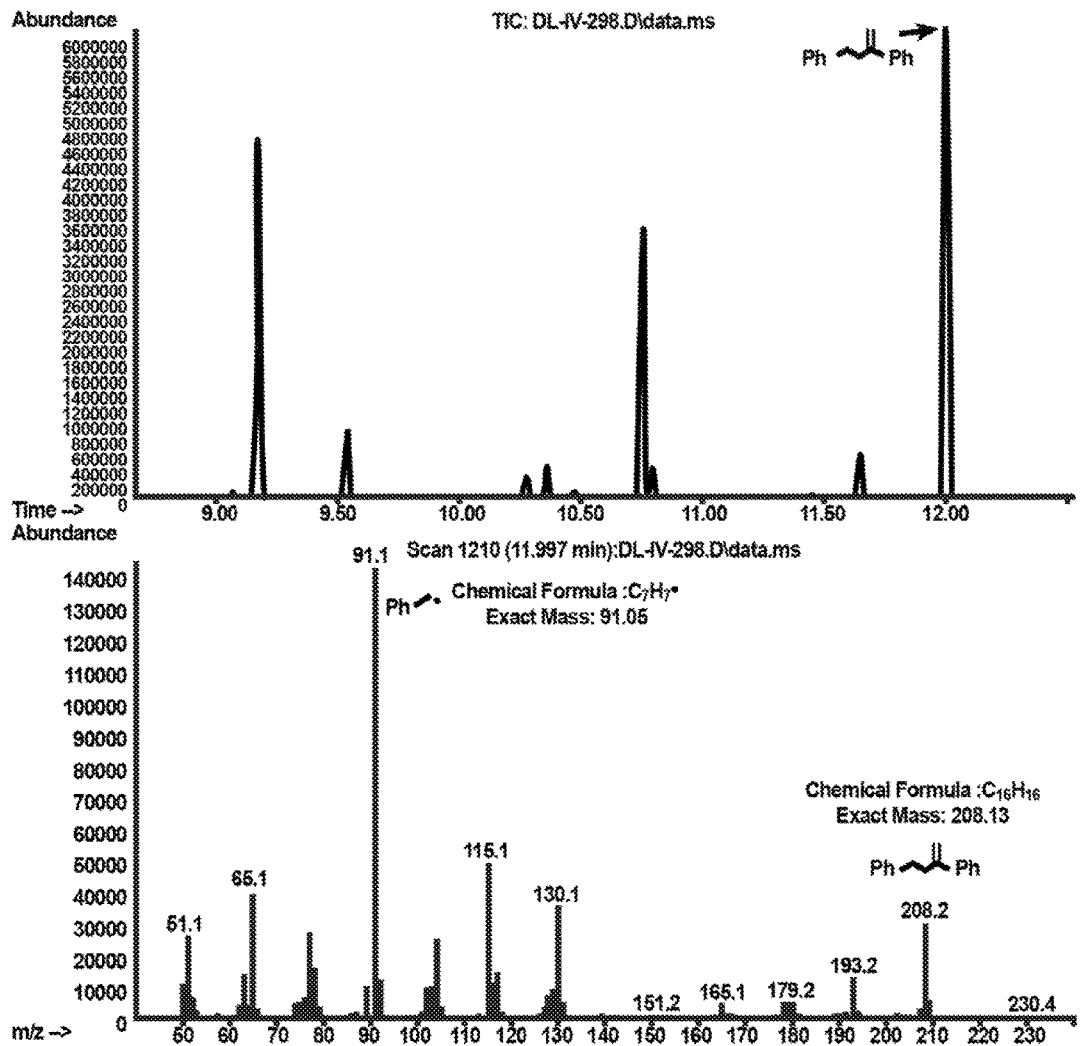

FIG. 42. GC/MS trace of the co-dimerization of styrene (250 mM) and 1-heptene (250 mM) with 1 (25 mM) to produce co-dimers. Mass spectrum corresponds to indicated peak.

Figure 43:
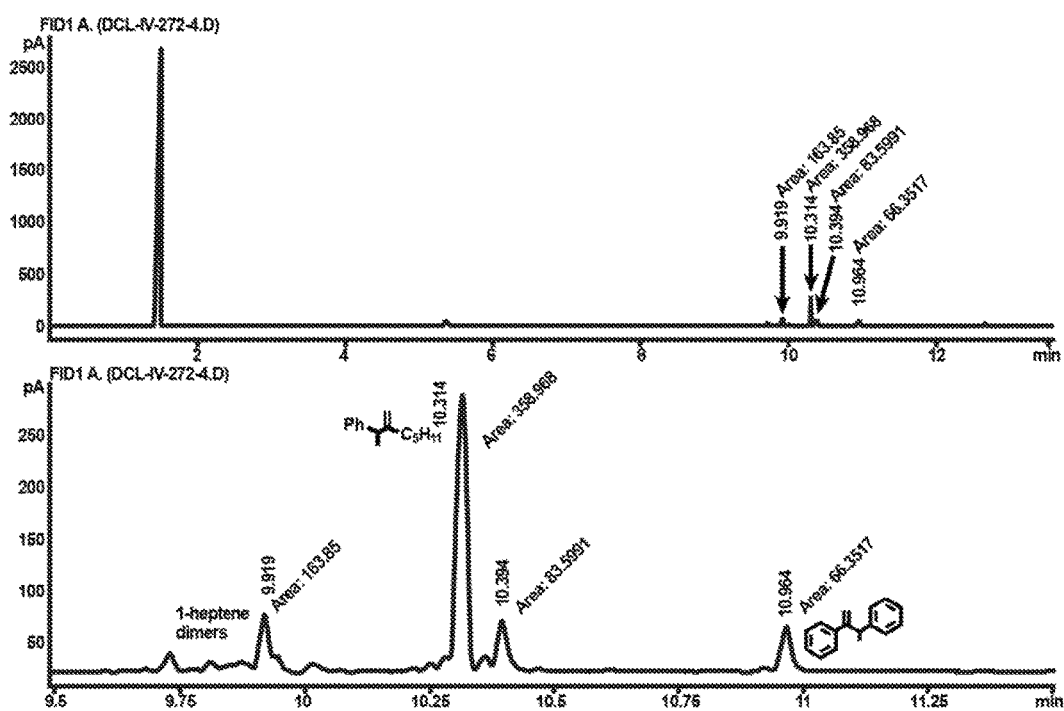

FIG. 43. GC trace of the nickel-catalyzed co-dimerization of styrene and 1-heptene to generate the major product shown. The 1-heptene dimers and styrene dimer are assigned based on GC/MS (vide infra). The regiochemistry of the styrene dimer for this Ni-catalyst was similar to that presented by Ho et al. (Angew. Chem. Int. Ed. 49:9182 (2010)).

Figure 44:
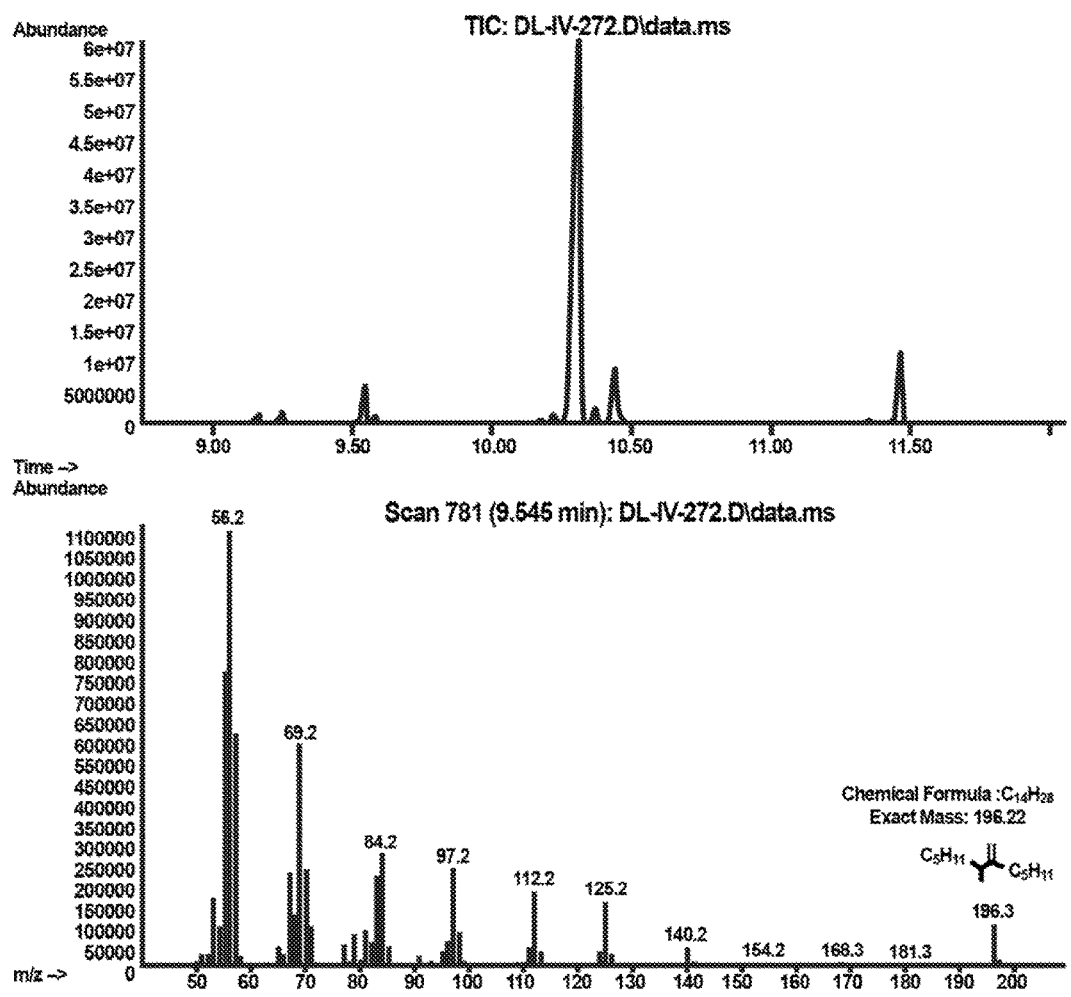

FIG. 44. GC/MS trace of the nickel-catalyzed co-dimerization of styrene and 1-heptene. Mass spectrum corresponds to indicated peak.

Figure 45:
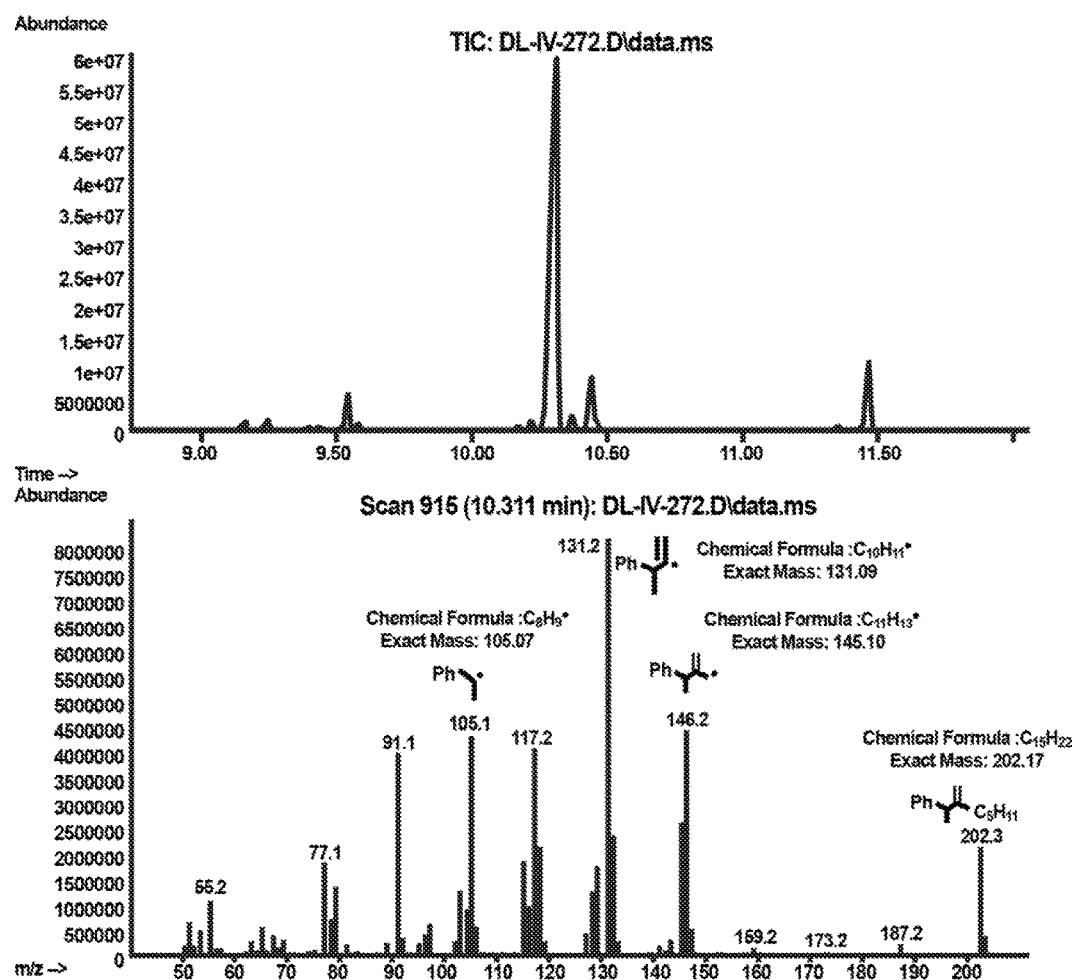

FIG. 45. GC/MS trace of the nickel-catalyzed co-dimerization of styrene and 1-heptene. Mass spectrum corresponds to indicated peak.

Figure 46:
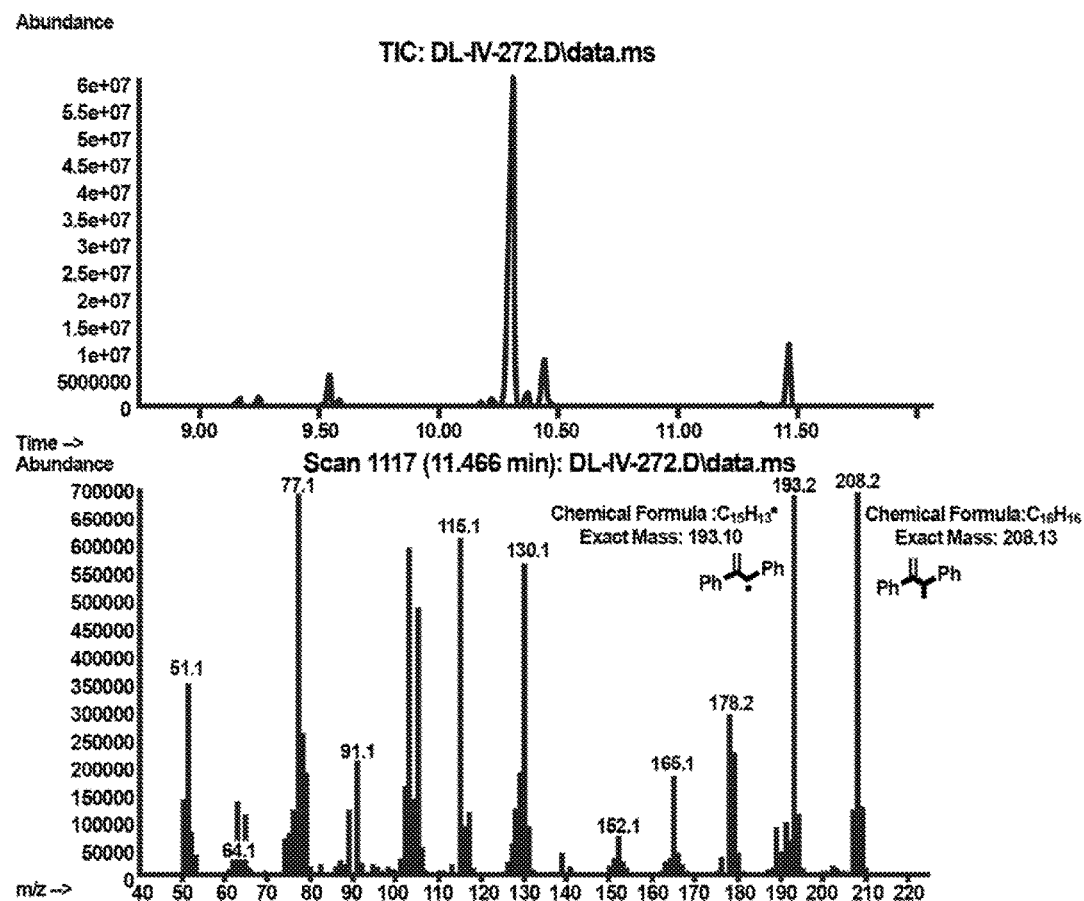

FIG. 46. GC/MS trace of the nickel-catalyzed co-dimerization of styrene and 1-heptene. Mass spectrum corresponds to indicated peak.

Figure 47:
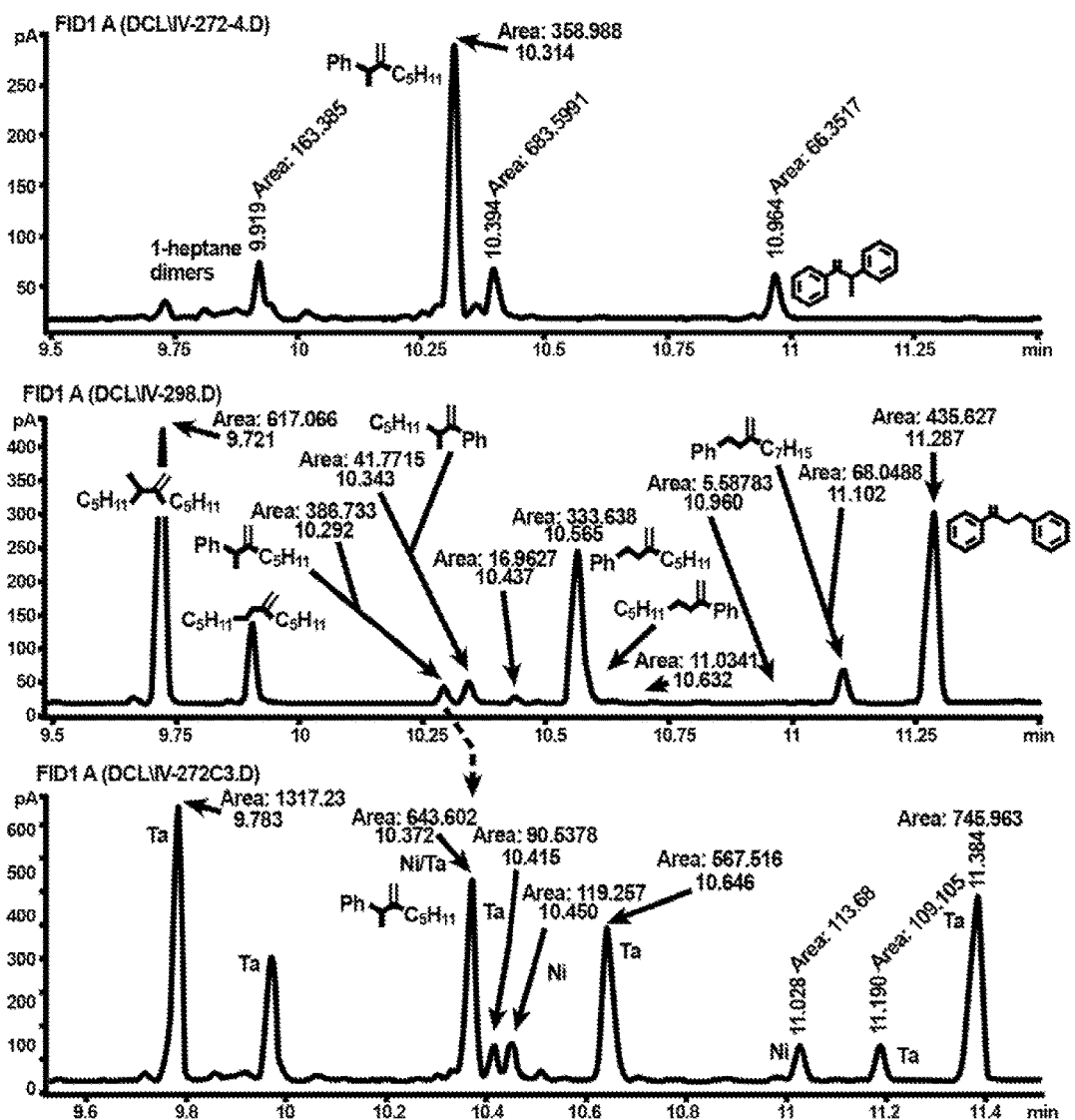

FIG. 47. Top: Reproduction of FIG. 43 (bottom). Middle: Reproduction of FIG. 36 (bottom). Bottom: GC trace of the co-injection of styrene/1-heptene co-dimerization reactions effected by 1 and the in situ generated Ni-catalyst. The peaks marked with "Ta" are from the tantalum-catalyzed reaction, and those marked with "Ni" are from the nickel-catalyzed reaction. The red arrow highlights that the co-dimer peak at 10.29 min (middle trace) corresponds to the 2-phenyl-3-methylene-octane product.

Figure 48:
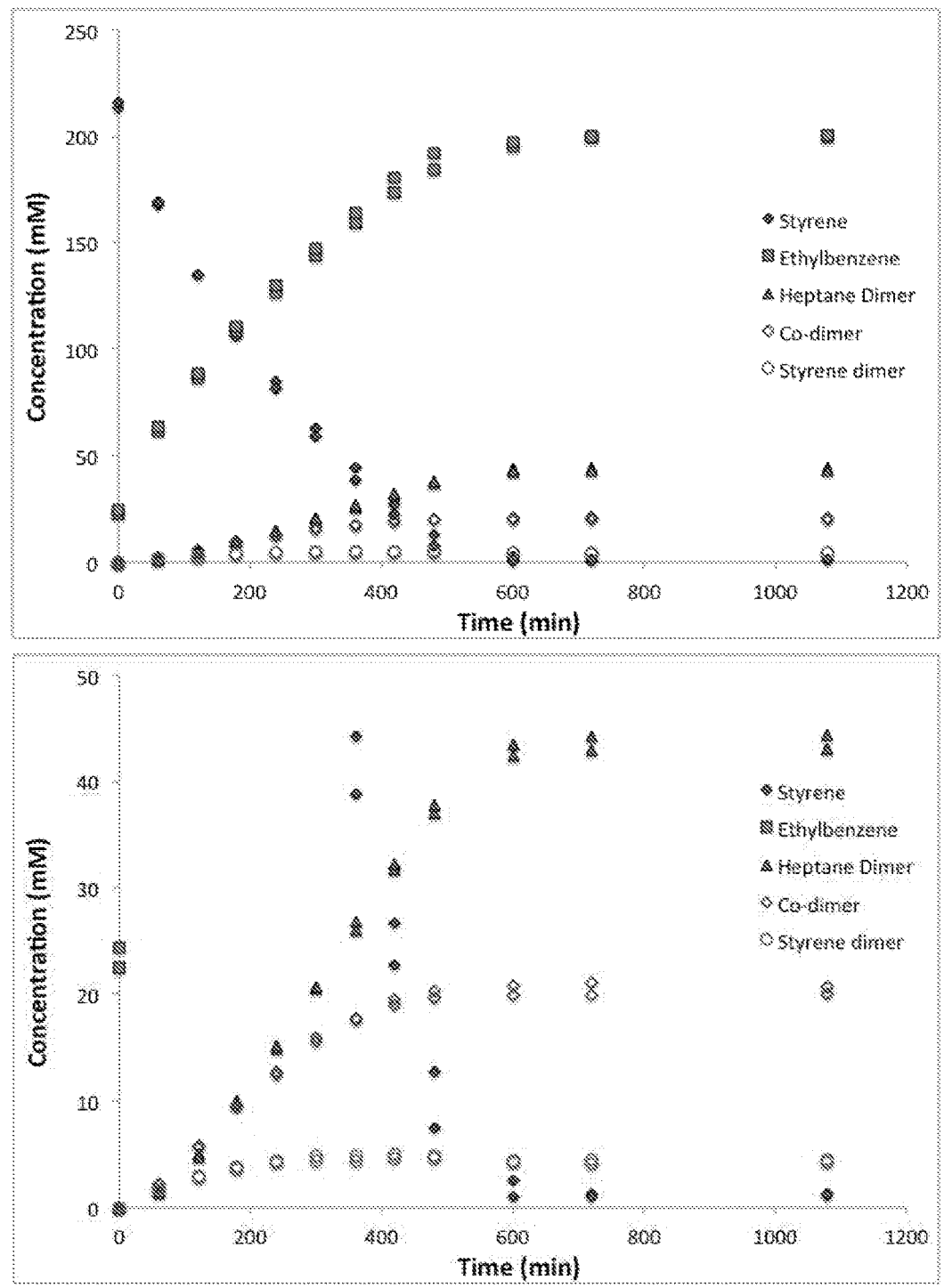

FIG. 48. Plots of reaction progress over time for Entry 7 in Table 4. Top: Overlay of both data sets. Bottom: Expansion of product concentration range. Lines are drawn as visual guides.

Figure 49:
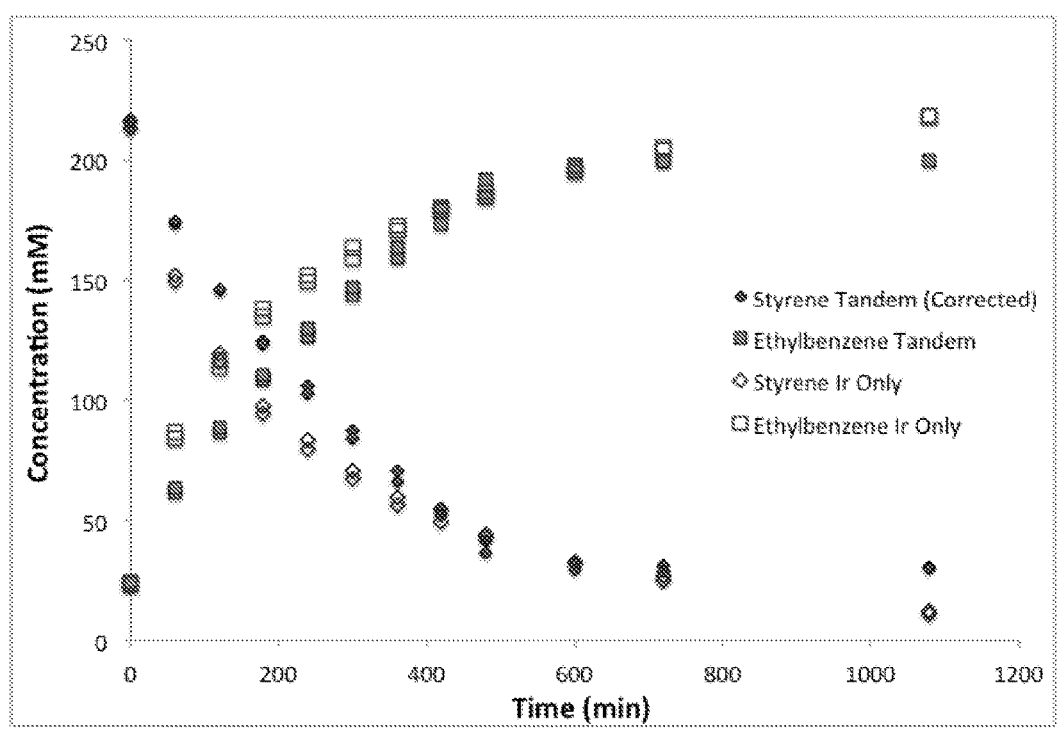

FIG. 49. Overlay of reaction progress for runs from Entry 7 in Table 4 (filled points), and styrene/n-heptane transfer hydrogenation catalyzed by only 2 (hollow points). Only styrene and ethylbenzene concentrations are shown for clarity. The styrene concentration for the tandem reactions was corrected by compensating for the amount of styrene consumed in dimerization reactions to form either styrene dimers or styrene/n-heptane co-dimers.

DETAILED DESCRIPTION

As used herein and in the appended claims, the singular forms "a," "an," and "the" include plural referents unless the context clearly dictates otherwise. Thus, for example, reference to "a catalyst" includes a plurality of such catalysts and reference to "the alkane" includes reference to one or more alkanes and so forth.

Also, the use of "or" means "and/or" unless stated otherwise. Similarly, "comprise," "comprises," "comprising" "include," "includes," "including," "have," "haves," and "having" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

As exploitation of traditional crude oil reserves becomes economically and geopolitically more volatile, and concern regarding $CO_2$ emissions from the current inefficient use of carbon-based energy carriers increases, many countries and industries are actively pursuing alternate fuel sources. These factors are driving the development of new technologies for fuel production from carbon sources such as bitumen and kerogen (so-called oil sands and shale oil), natural gas, and lignocellulosic biomass. In contrast to fuels derived from crude oil that are collected by fractional distillation, obtaining hydrocarbons in the desired weight range from these alternate carbon sources often requires extensive refining and synthetic manipulation, such as catalytic cracking and Fischer-Tropsch synthesis using syngas. In addition to the optimal fuel-range hydrocarbons ($C_8$-$C_{22}$), lighter alkanes and alkenes are abundant by-products of these processes. Currently, these light hydrocarbons have little value as fuels due to their volatility and low volumetric energy density. This inherent inefficiency in fuel production will increase both the economic and environmental cost of continued exploitation of these emerging carbon sources.

In order to better utilize low carbon number energy carriers, these feedstocks need to be upgraded to higher molecular weight compounds, ideally in the diesel fuel-range ($C_{10}$-$C_{22}$). Such a process must necessarily perform chemistry on alkanes under relatively mild conditions: the entropic cost of coupling smaller carbon chains into larger ones means that high temperatures are potentially thermodynamically incompatible. One possible technology for achieving this goal is alkane metathesis. Alkane metathesis operates via combined alkane dehydrogenation and alkene metathesis using either two separate catalysts, or one catalyst capable of both transformations. In the ideal case, two $C_n$ alkanes afford one $C_{2n-2}$ alkane and one equivalent of ethane in an approximately thermoneutral reaction; however, alkane metathesis tends toward a statistical carbon number distribution of alkanes, with few examples that can achieve any selectivity for the desired $C_{2n-2}$ product. While further catalyst development efforts may result in a viable process, alternative methods for upgrading light hydrocarbons are also needed.

The disclosure provides an approach toward light hydrocarbon upgrading based on a tandem alkane dehydrogenation and alkene dimerization. This method takes advantage of the mixed nature of many light by-product streams by incorporating both alkanes and alkenes as substrates. In an ideal system (shown for a linear alkane and 1-alkene in Scheme I), one catalyst would dimerize the alkene component of the mixed feedstock to a $C_{2n}$ alkene. Subsequent transfer hydrogenation by a second catalyst would convert the alkane component to a 1-alkene, while hydrogenating the $C_{2n}$ product to an alkane. The 1-alkene thus formed is then catalytically dimerized with a second equivalent of 1-alkene, and the cycle continues; the net reaction is coupling of alkane and alkene to higher alkane, with no by-products generated. Calculations indicate that such a reaction is thermodynamically favored below ~250° C.; therefore, catalysts for both dimerization and transfer hydrogenation must operate with appreciable rates at relatively mild temperatures.

Scheme I: Idealized Tandem Catalytic Approach toward Alkane/Alkene Upgrading

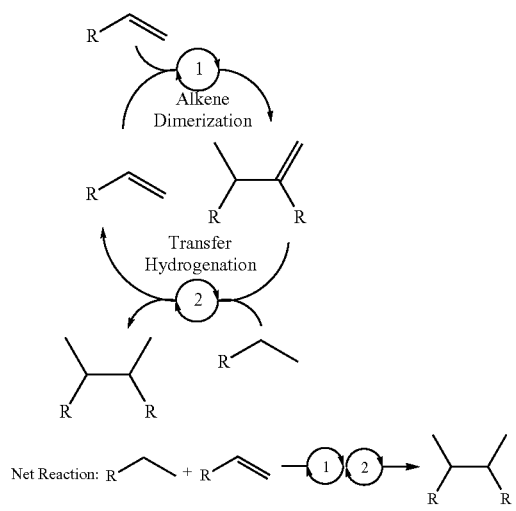

The disclosure demonstrates this process using a dual homogeneous catalytic system in which a dimerization catalyst (1) comprises a structure of Formula II effects alkene dimerization, and alkane/alkene transfer hydrogenation is carried out by a hydrogenation catalyst. These catalysts function in tandem to affect alkane/alkene coupling.

In a particular embodiment, hydrogen transfer catalyst (2) comprises a structure of Formula I:

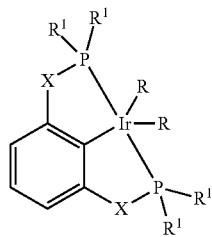

(I)

wherein, each R is independently H or a $(C_1-C_{30})$hydrocarbyl radical; each $R^1$ is independently a $(C_1-C_{30})$hydrocarbyl radical; and each X is independently an O or $CH_2$.

In a further embodiment, hydrogen transfer catalyst (2) comprises a structure of Formula I(a):

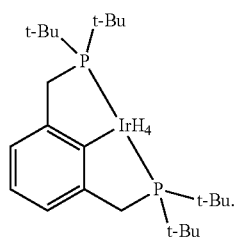

I(a)

In a particular embodiment, dimerization catalyst (1) comprises a structure of Formula II:

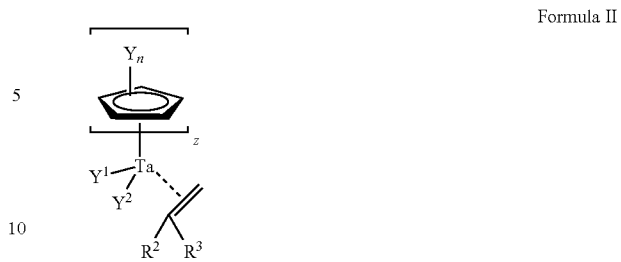

Formula II wherein, Z is either 1 or 2; n is an integer from 1 to 5; each Y is independently selected from D, H, optionally substituted $(C_1-C_6)$alkyl, silane, and $(C_1-C_4)$alkylsilane; $Y^1$ is a H, D, halo, $=S$, $=O$, $PMe_3$, $=C(H)$ $(CMe_3)$; $Y^2$ is a H, D, halo, $=S$, $=O$, $PMe_3$, or absent; $R^2$ is a H, aryl, optionally substituted $(C_1-C_{15})$alkyl, or an optionally substituted $(C_1-C_{15})$hetero-alkyl; and $R^3$ is a H, aryl, optionally substituted $(C_1-C_{15})$alkyl, or an optionally substituted $(C_1-C_{15})$ hetero-alkyl.

In another embodiment, dimerization catalyst (1) comprises a structure of Formula II(a):

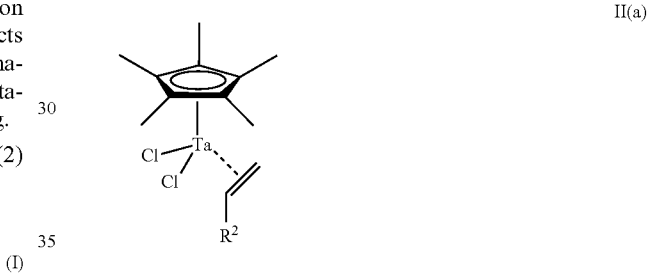

II(a)

wherein, $R^2$ is an aryl, optionally substituted $(C_1-C_{15})$alkyl, or an optionally substituted $(C_1-C_{15})$hetero-alkyl.

Ta-based alkene dimerization catalyst having the general Formula II were used in the Examples presented herein. Cp*TaX$_2$(alkene) complexes are reported to be "indefinitely active" for the selective dimerization of 1-alkenes to two regioisomers at temperatures up to 100° C. (see Scheme II below); they are inert to internal alkenes and the product 1,1-disubstituted alkenes. In addition, no co-catalyst or activator is required.

Scheme II

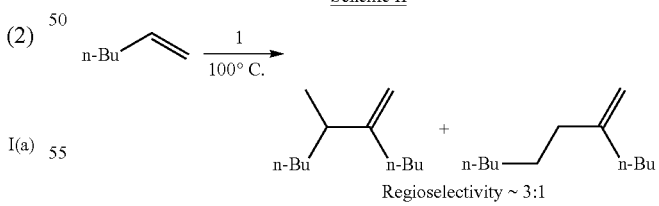

Regioselectivity ~ 3:1

As described above, the disclosure provides a dual homogeneous catalytic system for alkane/alkene coupling based on an early/late transition metal dichotomy: alkene dimerization is effected by a dimerization catalyst (1) comprising the structure of Formula II or Formula II(a), while transfer hydrogenation is performed by a hydrogen transfer catalyst (2) comprising the structure of Formula I of Formula I(a). This system is capable of coupling, for example, 1-hexene and n-heptane with a high degree of catalyst cooperativity. This system operates by a sacrificial $H_2$ acceptor pathway, in which the alkene substrate, and not the $C_{2n}$ product, acts as the hydrogen acceptor (Scheme III). Thus, for every equivalent of alkane upgraded, one equivalent of a different alkane is generated as a byproduct. An additional feature of this system is that in most cases the alkene substrate can also function as a coupling partner: for example, in 1-hexene/n-heptane mixtures, competitive homodimerization of 1-hexene generates a substantial amount of $C_{12}$, along with $C_{13}$ resulting from the coupling of 1-hexene and 1-heptene (generated via transfer hydrogenation).

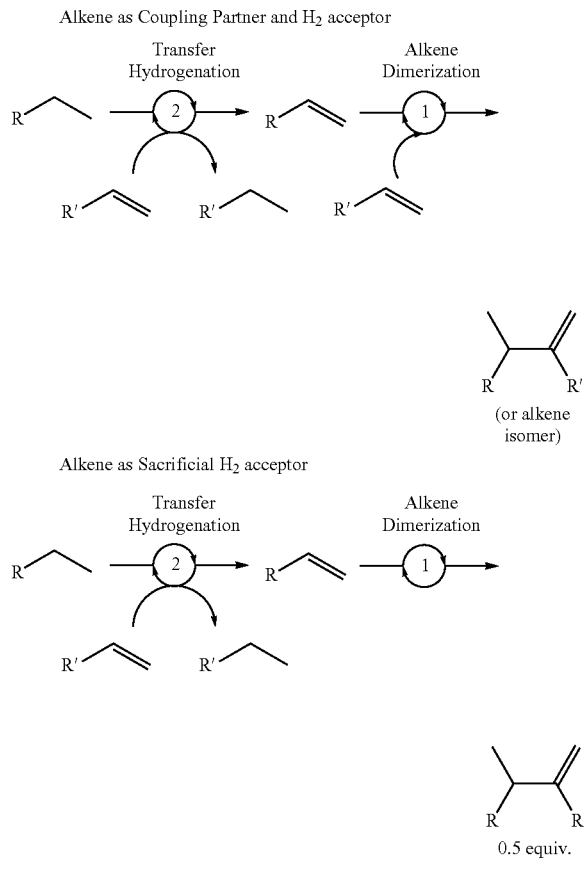

Figure 1:
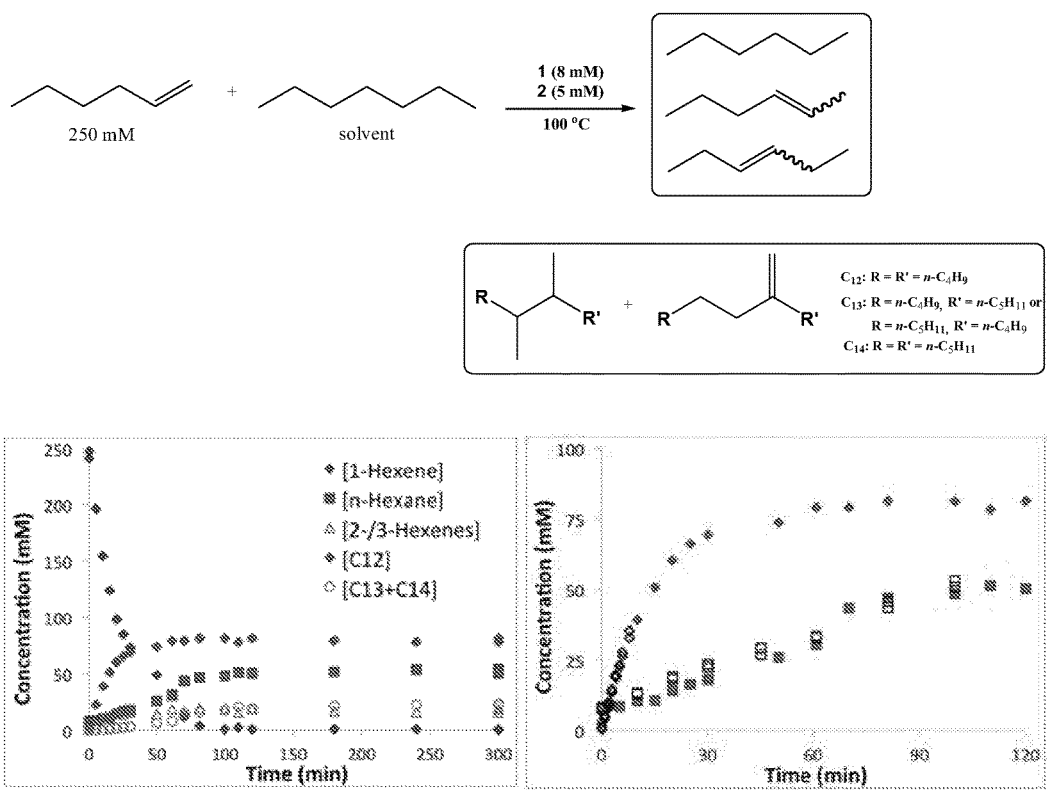
FIG. 1. A time evolution plot of the tandem catalytic coupling of 1-hexene/n-heptane. Top: Reaction conditions and products observed ("1" denotes dimerization catalyst; "2" denotes hydrogenation catalysts). Bottom left: Time course plot for concentrations of all observed species. Bottom right: Expansion and simplification showing formation of $C_{12}$ (from 1-hexene dimerization) and n-hexane (from 1-hexene/n-heptane transfer hydrogenation). Points are from tandem reactions, while black hollow points represent several individual catalytic runs with either 1 (diamonds) or 2 (squares). These data indicate that the rates of the individual catalytic reactions are identical to the rates observed during tandem catalysis, and therefore the two catalysts operate independently.

Both catalysts operate independently, with no mutual inhibition or decomposition over the course of the reaction (see FIG. 1). For example, kinetic studies reveal that 1-hexene dimerization catalyzed by the dimerization catalyst of Formula II exhibits positive order (<1) dependence on [1-hexene], with an approach to saturation at high concentrations; additionally, the dimerization rate increases very little with temperature. In stark contrast, the rate of 1-hexene/n-heptane transfer using the hydrogenation catalyst of Formula I has inverse order dependence on [1-hexene], and increases substantially with temperature. These opposing kinetic features lead to an imbalance in the relative rates of these two processes as either the concentration of 1-hexene is raised, or the reaction temperature is raised. In an effort to identify other alkene/alkane combinations that are amenable to tandem catalysis, the use of styrene has been studied as a sacrificial hydrogen acceptor for alkane dimerization. By attenuating the ratio of the two catalysts, a high degree of selectivity (>26:1) for tandem catalysis in this styrene/alkane system can be realized.

The disclosure also provides a in-depth kinetic study of the dimerization of 1-hexene catalyzed by dimerization catalyst 1 (see, Scheme I-III) at elevated temperatures and low initial substrate concentrations. The catalyst of Formula II (e.g., Cp*TaCl$_2$(alkene) complexes) undergo rapid decomposition at 100° C. in the absence of added alkene. Thus, catalyst decomposition at these elevated temperatures should be especially problematic at low concentrations of 1-alkene, since these conditions would favor Cp*TaCl$_2$(alkene) as the catalyst resting state. It is surprising, then, that the tandem catalytic alkane/alkene coupling operates at exactly this set of conditions with no apparent catalyst decomposition, even over >30 hours with 1-alkene added slowly via syringe pump (see Examples, below).

Thus, an aspect of the disclosure is that the transfer hydrogenation/dimerization occurs in a single-stage tandem process. In one particular version the $C_n$ alkene reactant is dimerized by dimerization catalyst 1 (comprising a structure of Formula II or II(a)) to generate a new $C_{2n}$ alkene product. This $C_{2n}$ alkene is converted to the $C_{2n}$ alkane by transfer hydrogenation with hydrogenation transfer catalyst 2 (comprising a structure of Formula I or I(a)); the source of hydrogen in this case is the $C_n$ alkane reactant. This generates a $C_n$ alkene, which will undergo dimerization with dimerization catalyst 1 having the structure of Formula II or II(a), producing more $C_{2n}$ alkene. This process would continue until all of the alkene equivalents are consumed and converted to the $C_{2n}$ alkane. For simplicity Scheme IV shows a single isomer of the product, but a different isomer or a mixture of two or more might result preferentially, depending on the choice of dimerization catalyst 1.

Scheme IV

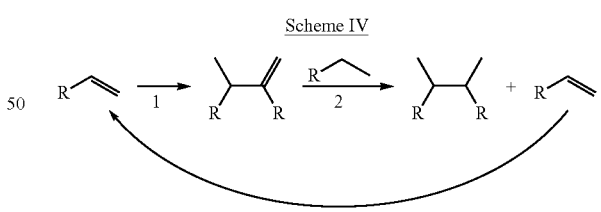

This tandem process can also be applied to a number of alternate transformations, such as combining transfer hydrogenation with oligomerization, such that the reaction of one molecule of $C_n$ alkane with x molecules of $C_n$ alkene would result in a $C_{(x+1)n}$ alkane. It may also be possible to effect conversion of two (or more) molecules of $C_n$ alkane to higher alkanes, either by carrying out the reaction in the presence of a sacrificial hydrogen acceptor, such as an alkene that cannot undergo oligomerization or another species; or by devising conditions such that the $H_2$ liberated during transfer dehydrogenation can be separated from reactant and products.

In order for this tandem process to occur, the two catalysts are present in the same reactor, and retain their activity under the reaction conditions needed to effect both transformations. This is accomplished by careful choice of the two catalysts such that mutual or individual deactivation does not occur. For example, in a batch reaction, both catalysts are dissolved and/or suspended in the reaction medium containing or consisting of the alkane/alkene mixture. In a flow reactor, the two catalysts would be supported on the same solid, or two solid catalysts would be intimately mixed, and the alkane/alkene reactants passed over this dual catalyst as either a gas or liquid.

The specific examples below have been successfully carried out, demonstrating the feasibility of the disclosed process. The disclosure thus, provides a homogeneous dual Ta/Ir catalyst system can affect both selective coupling of alkane/alkene mixtures and dimerization of alkanes to branched alkene products with a high degree of cooperation. Additional modification can include modifying the Ir catalyst and/or by selecting a different dimerization catalyst to produce less branched alkene isomers; these latter products may be more desirable from a fuels standpoint as well.

Example 1

General Considerations:

All experiments were performed under an argon inert atmosphere using standard Schlenk line, high-vacuum line, or glovebox techniques. Solvents for routine syntheses (pentane, toluene, diethyl ether, tetrahydrofuran (THF)) were dried by passage through activated alumina, degassed under vacuum by several freeze-pump-thaw cycles, and stored over activated 4 Å molecular sieves under an inert atmosphere. n-Heptane for use in catalytic reactions (HPLC grade, >99%, Sigma-Aldrich) was pre-dried by stirring ~400 mL over $CaH_2$ (~10 g) for at least 48 hours. The solvent was then vacuum transferred onto "titanocene" (~1 g) and stirred overnight; the solution remained black-green throughout. The n-heptane was collected from this titanocene solution by a final vacuum transfer and stored under an argon atmosphere. 1-Hexene, 1-heptene, and neohexene (isoprene-free) were distilled under argon from $CaH_2$ after stirring for several days.

NMR Spectroscopy:

Spectra were acquired on a Varian Mercury 300 MHz instrument with a relaxation delay time of 2 seconds. Spectra were processed in the following way using MestReNova: automatic baseline correction, automatic phase correction, exponential apodization along t1 of 1.00 Hz, and automatic linear correction applied to the integrals.

GC Analysis:

Gas chromatography was performed on an Agilent 6890N instrument using a flame ionization detector and a DB-1 capillary column (10 m length, 0.10 mm diameter, 0.40 μm film). Runs used the following program: hold at 35° C. for 2 minutes, ramp temperature at 2° C. min$^{-1}$ to 50° C., hold at 50° C. for 2 minutes, ramp temperature at 100° C. min$^{-1}$ to 290° C., hold at 290° C. for 5 minutes.

Response factors for linear hydrocarbons ranging from $C_5$ to $C_{18}$ versus adamantane were determined by the following procedure. Two standard samples were prepared containing known amounts of ten compounds (n-pentane, 1-hexene, n-heptane, n-octane, 1-dodecene, 1-tridecene, 1-tetradecene, 1-hexadecene, n-octadecane, and adamantane) dissolved in dichloromethane. Analysis of these two solutions by GC generated data used to calculate individual response factors for each compound versus adamantane using the following formula:

Resp. factor=$([Area_{analyte}] \times [mmol_{adamantane}])/([Area_{adamantane}] \times [mmol_{analyte}])$ The following response factors were obtained:

|  | Run 1 | Run 2 |
| --- | --- | --- |
| n-Pentane | 0.3947 | 0.3979 |
| 1-Hexene | 0.4970 | 0.5158 |
| n-Heptane | 0.6250 | 0.6320 |
| n-Octane | 0.7215 | 0.7364 |
| 1-Dodecene | 1.1945 | 1.2061 |
| 1-Tridecene | 1.3309 | 1.3274 |
| 1-Tetradecene | 1.4134 | 1.3967 |
| 1-Hexadecene | 1.6722 | 1.6639 |
| n-Octadecane | 1.8343 | 1.8544 |

These data were plotted versus carbon number, giving a linear correlation in the range analyzed (See FIG. 10).

The equation of the line was used to determine response factors for all of the hydrocarbons analyzed (the branching in the $C_{12}$-$C_{14}$ dimers generated in catalytic reactions is assumed to have negligible effect on the response).

| $C_6$ | 0.5121 |
| --- | --- |
| $C_{12}$ | 1.1919 |
| $C_{13}$ | 1.3052 |
| $C_{14}$ | 1.4185 |

The response factor for neohexene versus adamantane was established to lie outside this correlation, and was determined independently from two separate runs. The response factors were 0.5982 (run 1) and 0.5853 (run 2) for an average value of 0.5853.

GC/MS analysis was performed on an HP Model 6890N instrument using an HP5-1 column (30 m length, 25 mm diameter, 0.40 μm film) and an HP 5973 mass-selective EI detector.

Dimerization of 1-Hexene Using Dimerization Catalyst:

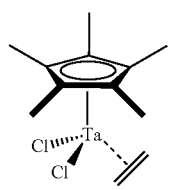

1

Dimerization catalyst 1 (6.6 mg, 0.016 mmol) was dissolved in 2 mL of a standard solution of 1-hexene (240.8 mM) and adamantane (25.4 mM) in n-heptane in a 4 mL screw-top vial. The vial sealed with a Teflon-lined screw cap. The mixture was heated briefly with a heat gun to dissolve the precatalyst and ensure a homogeneous solution. The solution was then split into ten aliquots of 0.2 mL each in ten separate 4 mL vials containing stir bars. These vials were sealed and stirred at 100° C. in an aluminum block heater (except for one vial representing $t_0$). At specified time intervals, vials were removed from the heat block, immersed in a dry-ice/acetone bath to rapidly cool the contents, and then diluted with dichloromethane to quench the reaction. These solutions were passed through a short plug of silica gel into a GC autosampler vial, and analyzed by GC. This procedure was repeated three times to generate the time profile shown in FIG. 2.

Procedure for Determining Initial Rates of 1-Hexene Dimerization.

Dimerization catalyst 1 (10.0 mg, 0.0240 mmol) was dissolved in 3 mL of a standard solution of 1-hexene (248, 252, 412, 699, 1010, 2000, or 3996 mM) and adamantine internal standard (~25 mM) in n-decane in a 4 mL screw-top vial. The vial was sealed with a Teflon-lined screw cap. The mixture was heated briefly with a heat gun and stirred vigorously to dissolve the precatalyst and ensure a homogeneous solution. The solution was then split into fifteen aliquots of 0.2 mL each in fifteen separate 4 mL vials containing stir bars. These vials were sealed and stirred at 80, 90, 100, 110, or 125° C. in an aluminum block heater. At specified time intervals, (1, 2, 3, or 4 minutes) vials were removed from the heat block, immersed in a dry-ice/acetone bath to rapidly cool the contents, and then diluted with dichloromethane to quench the reaction. These solutions were passed through a short plug of silica gel into a GC autosampler vial, and analyzed by GC.

Data for each time point was collected from 3 or 4 different vials, giving 12-15 data points for each initial rate determination. The concentrations of both major and minor product isomers were plotted versus time, and the $k_{obs}$ values calculated by linear regression analysis (TABLE 1, FIGS. 13, 15, 17, 19, and 21). These data were used to generate double reciprocal plots for each product isomer at each temperature (see FIGS. 14, 16, 18, 20, and 22). These plots were subject to linear regression analysis to generate slope/intercept values, which were used to calculate $k_1$, $K_{eq}$, and $k_2 K_{eq}'$ according to equations 1-8.

$$\text{Rate} = \frac{k_1 K_{eq}[1-\text{Hexene}][Ta]_0}{1 + K_{eq}[1-\text{Hexene}]} \quad (1)$$

$$\text{Rate}^{-1} = \frac{1}{k_1 K_{eq}[Ta]_0}[1-\text{Hexene}]^{-1} + \frac{1}{k_1 [Ta]_0} \quad (2)$$

$$k_1 = \frac{1}{b[Ta]_0} \quad (3)$$

$$K_{eq} = \frac{b}{m} \quad (4)$$

$$\text{Rate} = \frac{k_2 K_{eq}'[1-\text{Hexene}][Ta]_0}{1 + K_{eq}[1-\text{Hexene}]} \quad (5)$$

$$\text{Rate}^{-1} = \frac{1}{k_2 K_{eq}'[Ta]_0}[1-\text{Hexene}]^{-1} + \frac{K_{eq}}{k_2 K_{eq}'[Ta]_0} \quad (6)$$

$$k_2 K_{eq}' = \frac{1}{m[Ta]_0} \quad (7)$$

$$K_{eq} = \frac{b}{m} \quad (8)$$

TABLE 1

Initial Rate Data (numbers in parentheses are standard error determined from regression analysis)

| Entry | Temp. (° C.) | [1-Hexene]$_0$ (mM) | $k_{obs}$ Major ($10^{-5}$ M s$^{-1}$) | $k_{obs}$ Minor ($10^{-5}$ M s$^{-1}$) |
|---|---|---|---|---|
| 1 | 80 | 248 | 3.06 (8) | 0.73 (3) |
| 2 | 80 | 412 | 4.85 (10) | 1.19 (3) |
| 3 | 80 | 699 | 6.76 (12) | 1.59 (4) |
| 4 | 80 | 1010 | 7.28 (25) | 1.77 (7) |
| 5 | 80 | 2000 | 10.76 (44) | 2.54 (13) |
| 6 | 80 | 3996 | 12.42 (55) | 2.93 (14) |
| 7 | 90 | 248 | 4.35 (10) | 1.23 (4) |
| 8 | 90 | 412 | 7.52 (15) | 2.16 (6) |
| 9 | 90 | 699 | 10.21 (21) | 2.87 (7) |
| 10 | 90 | 1010 | 14.74 (29) | 4.10 (8) |
| 11 | 90 | 2000 | 18.58 (58) | 5.11 (19) |
| 12 | 90 | 3996 | 26.70 (58) | 7.44 (17) |
| 13 | 100 | 248 | 5.87 (10) | 1.85 (4) |
| 14 | 100 | 252 | 6.03 (12) | 2.00 (5) |
| 15 | 100 | 412 | 9.53 (27) | 2.98 (10) |
| 16 | 100 | 699 | 16.73 (41) | 5.56 (15) |
| 17 | 100 | 1010 | 21.37 (52) | 6.77 (19) |
| 18 | 100 | 2000 | 37.2 (11) | 12.24 (38) |
| 19 | 100 | 3996 | 42.9 (14) | 13.76 (48) |
| 20 | 110 | 248 | 6.66 (18) | 2.42 (7) |
| 21 | 110 | 412 | 10.75 (22) | 3.83 (9) |
| 22 | 110 | 699 | 18.22 (35) | 6.52 (13) |
| 23 | 110 | 1010 | 28.37 (48) | 10.17 (19) |
| 24 | 110 | 2000 | 41.7 (13) | 14.79 (45) |
| 25 | 110 | 3996 | 66.6 (18) | 23.78 (71) |
| 26 | 125 | 248 | 8.34 (22) | 3.62 (11) |
| 27 | 125 | 412 | 14.01 (33) | 6.08 (14) |
| 28 | 125 | 699 | 24.65 (76) | 10.84 (32) |
| 29 | 125 | 1010 | 33.4 (16) | 14.32 (65) |
| 30 | 125 | 2000 | 64.3 (34) | 28.3 (16) |
| 31 | 125 | 3996 | 102.1 (64) | 43.0 (30) |

Kinetic Fitting Using DynaFit.

Figure 2:
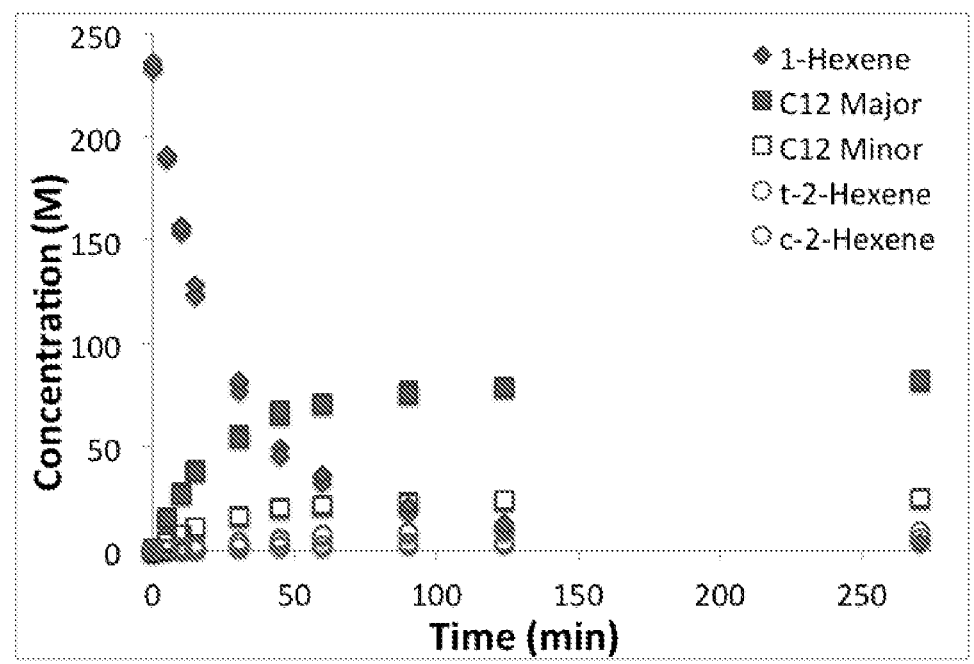
FIG. 2. A time evolution plot of the tandem catalytic coupling of the dimerization of 1-hexene (240 mM) catalyzed by 1 (8 mM) at 100° C. (three runs).
Figure 3:
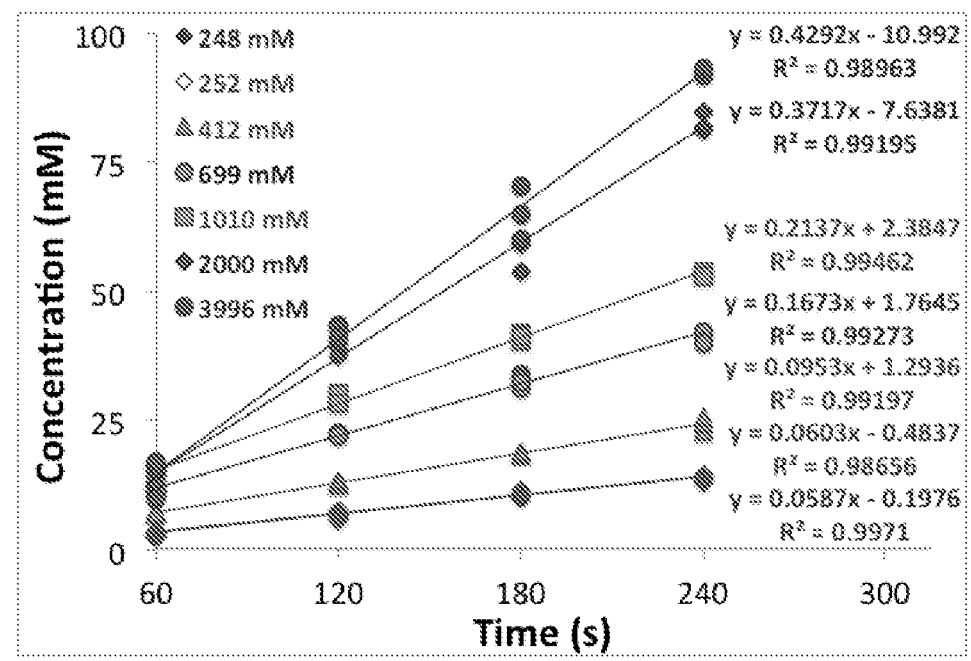
FIG. 3. Initial rate of formation of the major regioisomer from dimerization of 1-hexene (248-3996 mM) catalyzed by 1 (8 mM) at 100° C. (each line generated by linear regression of an overlay of at least three runs).
Figure 4:
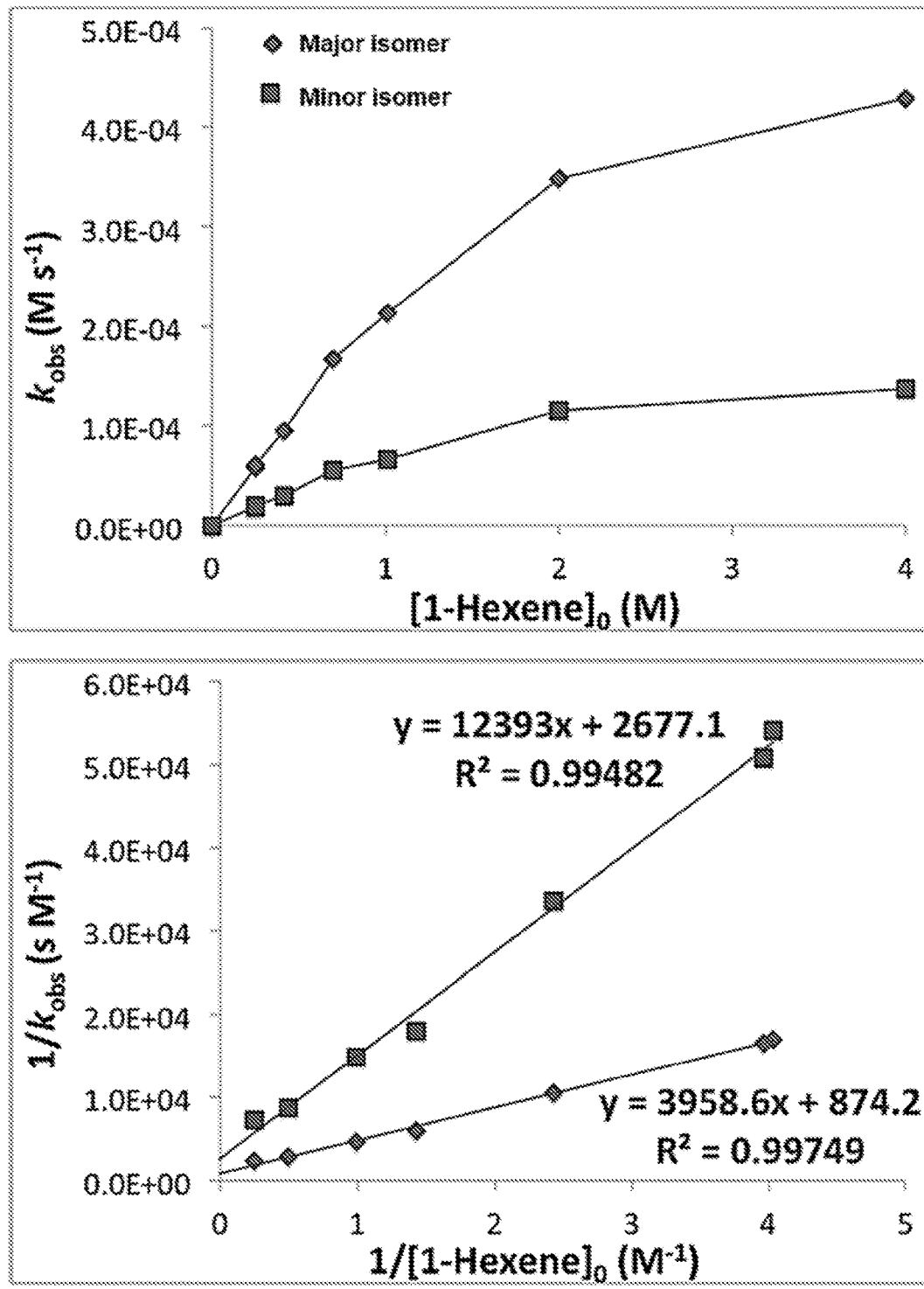
FIG. 4. Top: Plot of initial rate ($k_{obs}$) for 1-hexene dimerization (points represented by diamonds: major isomer; points represented by squares: minor isomer) catalyzed by 1 (8 mM) at 100° C. versus [1-hexene]$_0$ (248 mM-3996 mM; data from Table 1), indicating an approach to saturation. Bottom: Corresponding double-reciprocal plot to calculate values for $K_{eq}$, $k_1$, and $k_2K_{eq}$' according to equations 1-8.
Figure 5:
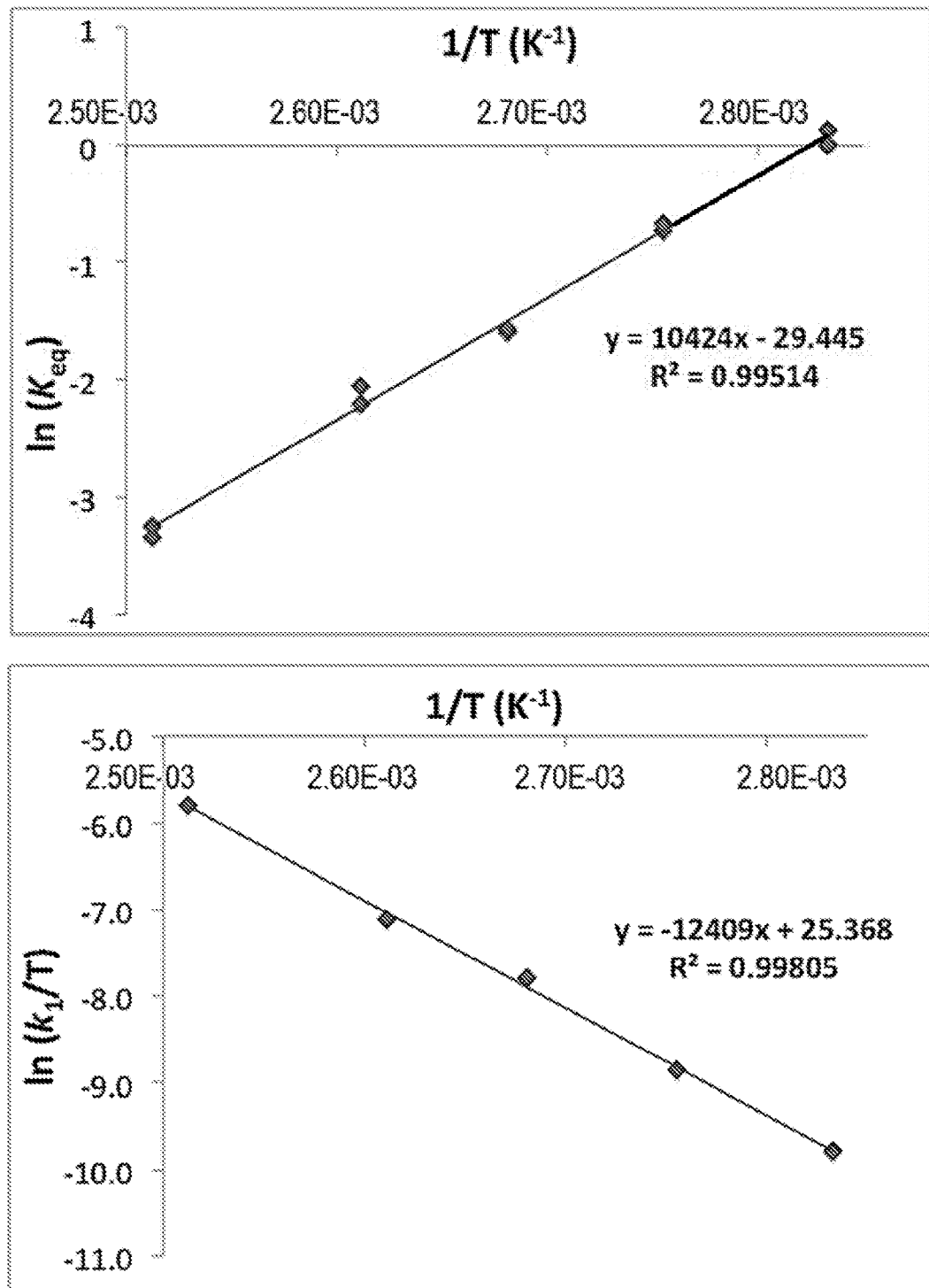
FIG. 5. Left: van't Hoff plot (80° C.-125° C.) for the equilibrium Cp*TaCl$_2$(1-hexene) (A)+1-hexene⇌Cp*TaCl$_2$(metallacycle) (B) governed by $K_{eq}$, with thermodynamic parameters. Right: Eyring plot (80° C.-125° C.) for the unimolecular decomposition of Cp*TaCl$_2$(metallacycle) (B into C) governed by $k_1$, with activation parameters.

The full time course data represented in FIG. 2 was fitted according to the mechanistic model from Scheme V, as well as terms for alkene isomerization to cis- and trans-2-hexene, using the freeware kinetics program DynaFit. Values for the rate and equilibrium constants $k_1$, $K_{eq}$, and $k_2 K_{eq}'$ determined at 100° C. were used. All equilibria were assumed to be rapid. The values of $K_{off}$ and $K_{off}'$ were set at different values ($K_{off}=K_{off}'=1, 2.5, 5, 10,$ and 15) and the quality of the fit determined by inspection.

Scheme V: Postulated Catalytic Cycles for the Dimerization of 1-Alkenes into Two Regioisomers Catalyzed by 1

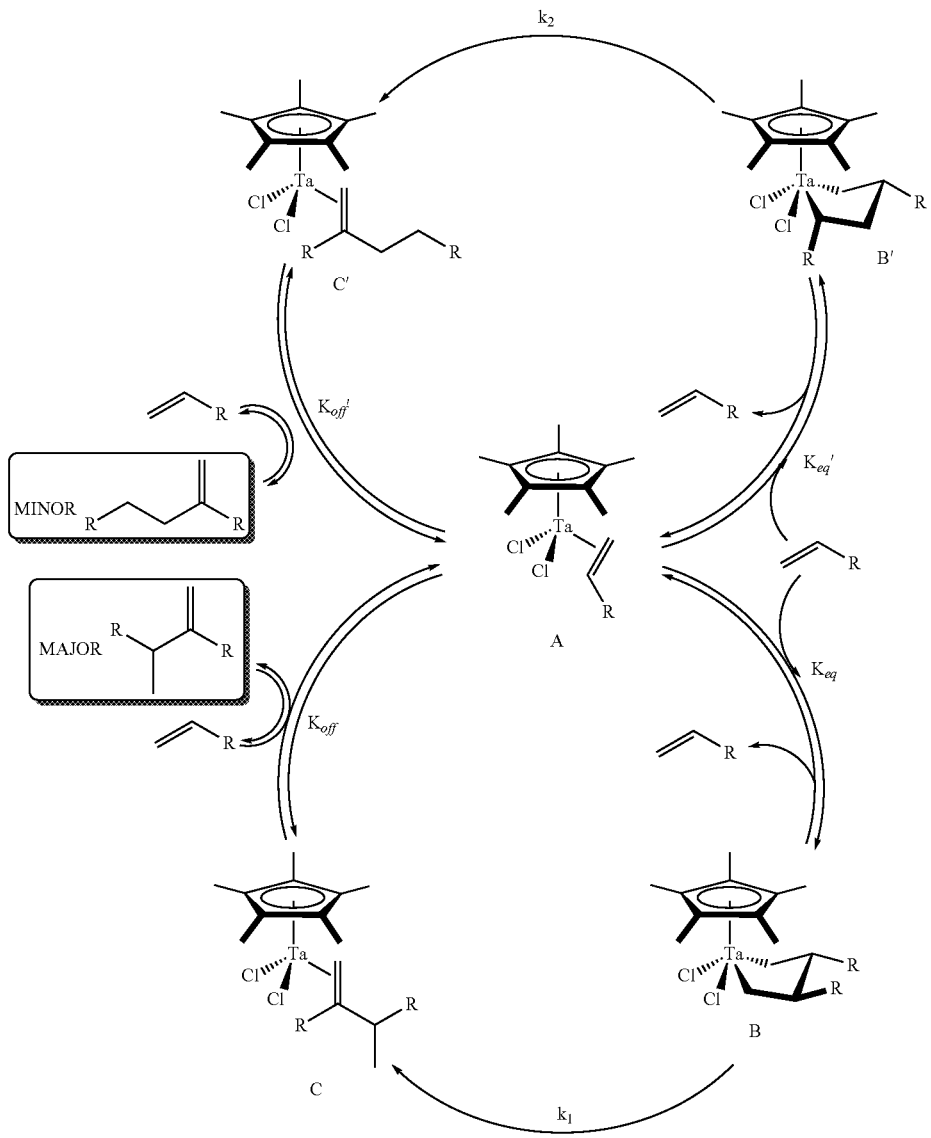

Intermediate values of $K_{off} \cong K_{off}' \cong 2.5\text{-}5$ gave the best correlation. Refining $K_{off}$ and $K_{off}'$ gave values of 4.4 (6) and 2.8 (9) respectively. Second order rate constants for alkene isomerization were determined by fitting according to the equation:

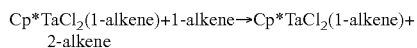

Cp*TaCl$_2$(1-alkene)+1-alkene→Cp*TaCl$_2$(1-alkene)+ 2-alkene (not an elementary step)

These values are $3.6(2)\times10^{-3}$ $M^{-1}$ $s^{-1}$ and $1.8(2)\times10^{-3}$ $M^{-1}$ $s^{-1}$ for the formation of cis- and trans-2-hexene respectively. Presumably this isomerization occurs via a Π-allylic-type mechanism, since the major catalyst resting state is the [Ta](1-alkene) complex, rather than an insertion/β-hydride elimination mechanism; however, due to the low degree of isomerization observed, the mechanism of this side-reaction was not experimentally tested.

Procedure for Determining Initial Rates of 1-Hexene/n-Decane Transfer Hydrogenation.

Hydrogen transfer catalyst 2 (8.8 mg, 0.0150 mmol) was dissolved in 3 mL of a standard solution of 1-hexene (248, 412, 699, or 1010 mM) and adamantine internal standard (~25 mM) in n-decane in a 4 mL screw-top vial. The solution was stirred to dissolve the precatalyst and ensure a homogeneous solution. The solution was then split into fifteen aliquots of 0.2 mL each in fifteen separate 4 mL vials containing stir bars. These vials were sealed and stirred at either 100 or 125° C. in an aluminum block heater. At specified time intervals, (10, 20, 30, or 40 minutes) vials were removed from the heat block, immersed in a dry-ice/acetone bath to rapidly cool the contents, and then diluted with dichloromethane to quench the reaction. These solutions were passed through a short plug of silica gel into a GC autosampler vial, and analyzed by GC.

Data for each time point was collected from 3 or 4 different vials, giving 12-15 data points for each initial rate determination. The concentrations of n-hexane and the 2-hexenes (combined) were plotted versus time, and the $k_{obs}$ values calculated by linear regression analysis (See FIG. 23 and FIG. 24). These rate data were then plotted versus [1-hexene]$_0$ (see FIG. 25).

Heating a solution of 1-hexene (248 mM) and hydrogen transfer catalyst 2 (5 mM) in n-decane leads to the generation of several products that can be analyzed by GC (Scheme VI).

Scheme VI

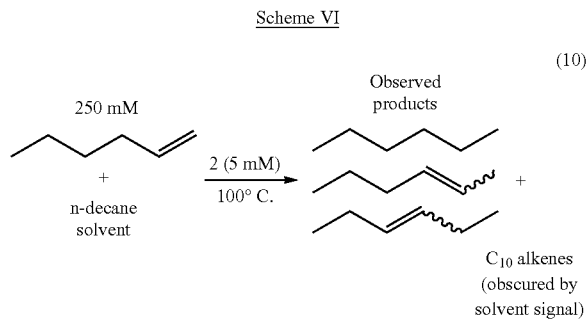

C$_{10}$ alkenes (obscured by solvent signal)

In the C$_6$ fraction, n-hexane (from transfer hydrogenation) and internal hexenes (from alkene isomerization) are observed. C$_{10}$ alkenes are also observed (including 1-decene), but accurate quantification of these species is not reliable due to overlap with the large signal for n-decane solvent. Therefore, the formation of n-hexane and internal hexenes has been monitored to generate initial rate data for transfer hydrogenation and alkene isomerization respectively (Table 2).

TABLE 2

Initial Rate Data for 1-Hexene/n-Decane Transfer Hydrogenation and 1-Hexene Isomerization Catalyzed by 2.

| Entry | [1-Hexene]$_0$ (mM) | Temp. (° C.) | $k_{obs}$ (hydrog) (10$^{-5}$ M s$^{-1}$)$^a$ | $k_{obs}$ (isom) (10$^{-5}$ M s$^{-1}$)$^a$ |
|---|---|---|---|---|
| 1 | 248 | 100 | 1.26 (5) | 1.00 (4) |
| 2 | 412 | 100 | 0.753 (38) | 1.53 (5) |
| 3 | 699 | 100 | 0.572 (20) | 2.31 (7) |
| 4 | 1010 | 100 | 0.387 (10) | 2.79 (6) |
| 5 | 248 | 125 | 12.4 (4) | 4.73 (20) |
| 6 | 412 | 125 | 8.85 (23) | 6.30 (16) |
| 7 | 1010 | 125 | 2.88 (14) | 11.8 (5) |

$^a$Numbers in parenthesis are standard error from regression analysis.

Figure 6:
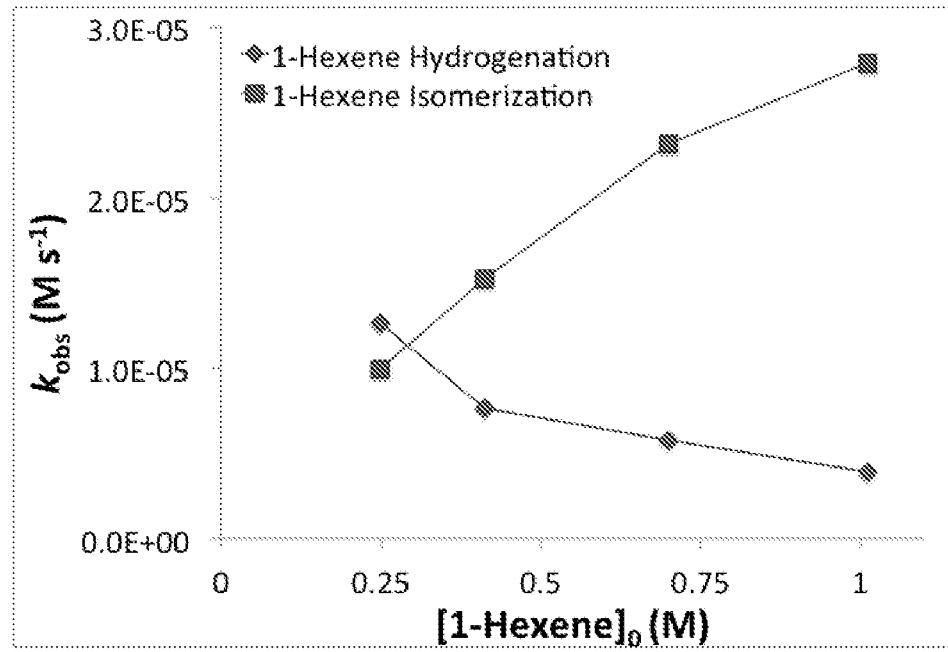
FIG. 6. Rates of 1-hexene/n-decane transfer hydrogenation and 1-hexene isomerization catalyzed by 2 at 100° C. versus initial [1-hexene] (248-1010 mM). The data clearly show inverse order in 1-hexene for transfer hydrogenation, and positive order in 1-hexene for isomerization.

Analysis of the initial rates of transfer hydrogenation and isomerization versus [1-hexene]$_0$ reveals that transfer hydrogenation is inverse order in [1-hexene] from 248-1010 mM, whereas isomerization is positive order in [1-hexene], exhibiting saturation behavior (see FIG. 6). The inverse dependence on [1-hexene] is consistent with previous work on cyclooctane/tert-butylethylene (TBE) transfer hydrogenation catalyzed by hydrogen transfer catalyst 2: the rate is first order in [TBE] at low concentrations (where the Ir dihydride F is the major resting state), and inverse order at higher concentrations. While inhibition by TBE is due to reversible oxidative addition/reductive elimination of a vinyl C—H bond, linear alpha olefins (LAOS, such as 1-hexene) inhibit catalysis by competitive formation of the 1-alkene complex G. Indeed, G (where the alkene is 1-octene) is reportedly a major resting state in TBE/n-octane transfer hydrogenation. Thus, at higher [1-hexene], the equilibrium in Scheme VII would be shifted toward G, which is not on the transfer hydrogenation cycle.

Scheme VII

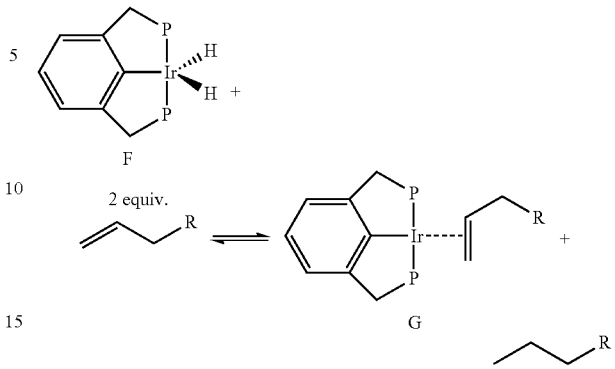

This shift in equilibrium between resting states is also consistent with the observation that the transfer hydrogenation rate is affected dramatically by temperature, increasing nearly 10-fold from 100-125° C. (see Table 2, entries 1 and 5). The equilibrium in Scheme VII is a 3-into-2 reaction, which means that the reverse direction is entropically favored; thus, an increase in temperature would shift the equilibrium toward F, which is an on-cycle intermediate for transfer hydrogenation. Furthermore, since G is also an active catalyst for alkene isomerization, this shift should decrease the rate of isomerization relative to transfer hydrogenation. This is exactly the case, where with an initial [1-hexene] of 248 mM, $k_{obs}$(hydrog)/$k_{obs}$(isom) is 1.26 at 100° C. and 2.62 at 125° C. Of course, temperature effects on the other steps of both catalytic cycles will influence these rates as well.

Notably, the determination that isomerization is positive order in [1-hexene] (from initial rate data) is in contrast to the zero order dependence previously reported for alkene isomerization catalyzed by hydrogen transfer catalyst 2 (observation over 5 half-lives with initial [1-alkene]=100 mM). This reaction proceeds by a Π-allylic mechanism that has a unimolecular turnover-limiting step and thus should be zero order in [1-alkene]; however, the positive order dependence observed here can be explained in terms of the equilibrium between resting states in Scheme VII. As the concentration of 1-hexene is increased, the steady state concentration of G will increase, leading to a higher rate of alkene isomerization. Thus, increasing [1-hexene] not only inhibits transfer hydrogenation, it also favors the undesirable alkene isomerization pathway. The trend toward saturation in the rate of 1-hexene isomerization shown in FIG. 6 is entirely consistent with a unimolecular turnover-limiting step in the n-allylic isomerization catalytic cycle.

Implications for Tandem Catalytic Alkane/Alkene Coupling.

The diametrically opposed kinetic trends in alkene dimerization catalyzed by dimerization catalyst 1 and transfer hydrogenation catalyzed by hydrogen transfer catalyst 2 is a major factor in the homogeneous tandem catalytic coupling of 1-hexene and n-heptane. As for many other one-pot dual catalyst processes, the optimal conditions for the individual catalysts do not necessarily translate into the optimal conditions for the pair. While dimerization catalyst 1 operates most efficiently at lower temperatures and high substrate loading, hydrogen transfer catalyst 2 works best at high temperatures and low substrate loading. Thus, in order to best match the rates of the two individual reactions, tandem catalysis is effective at a moderate temperature (100° C.) and an alkene concentration that is as low as possible. In terms of simple batch reactions, the initial optimization led to a 1-hexene loading of ~250 mM (see TABLE 3, entry 1).

TABLE 3

Temperature and Concentration Effects on 1-Hexane/n-Heptane Coupling by 1 and 2.

| Entry | [1-Hexane]$_0$ (mM) | [1]/[2] (mM) | Temp. (° C.) | n-Hexane (mM)$^a$ | $C_{12}$ (mM)$^a$ | $C_{13}/C_{14}$ (mM)$^a$ | TON for 1$^b$ | TON for 2$^b$ | Coop. (%) |
|---|---|---|---|---|---|---|---|---|---|
| 1 | 250  | 8/5 | 100 | 52  | 81  | 13/10 | 13 (3) | 10 (6)  | 63 |
| 2 | 500  | 8/5 | 100 | 88  | 193 | 15/10 | 27 (3) | 18 (7)  | 40 |
| 3 | 1000 | 8/5 | 100 | 87  | 432 | 18/10 | 58 (4) | 17 (8)  | 45 |
| 4 | 250  | 8/5 | 125 | 106 | 58  | 15/13 | 11 (4) | 21 (8)  | 39 |
| 5 | 500  | 8/5 | 125 | 140 | 162 | 24/14 | 25 (5) | 28 (10) | 37 |
| 6 | 1000 | 8/5 | 125 | 161 | 386 | 32/14 | 54 (6) | 32 (12) | 38 |
| 7 | 250  | 8/5 | 150 | 147 | 39  | 12/12 | 8 (3)  | 29 (7)  | 24 |
| 8 | 500  | 8/5 | 150 | 216 | 128 | 26/15 | 21 (5) | 43 (11) | 27 |
| 9 | 1000 | 8/5 | 150 |     |     |       |        |         |    |

$^a$Determined by GC/FID using adamantane as an internal st., avg. of at least 2 runs.
$^b$TONs in parentheses are for production of $C_{13}$ + $C_{14}$.

Raising the substrate loading to 500 or 1000 mM merely results in the production of more $C_{12}$ homodimer, with little additional tandem catalysis observed (see entries 2 and 3 of Table 3); this is due to the positive order dependence on [1-hexene] for dimerization catalyst 1, and the inverse order dependence on [1-hexene] for hydrogen transfer catalyst 2. Conversely, raising the temperature to 125° C. or 150° C. dramatically reduces catalyst cooperativity (entries 4 and 7 of Table 3), due to the much stronger temperature dependence exhibited by hydrogen transfer catalyst 2 relative to dimerization catalyst 1.

While increasing [1-hexene] or temperature results in a rate imbalance between the two catalysts, it is possible that increasing both of these variables would have complementary effects, allowing a higher degree of tandem catalysis at increased substrate loading Procedure for Styrene Dimerization Using Dimerization Catalyst 1.

Dimerization Catalyst 1 (10.4 mg, 0.025 mmol), styrene (53.5 mg, 0.514 mmol), and mesitylene (internal standard, 10.8 mg, 0.0898 mmol) were dissolved in $C_6D_6$ (1 mL). This solution was then transferred into two J. Young NMR tubes. Initial $^1H$ NMR spectra were recorded (see FIG. 27), and then the tubes were heated to 110° C. in an oil bath. After set time intervals, the tubes were removed from the oil baths and new spectra acquired, until ~95% conversion was reached (about 72 h, see FIG. 28). NMR yields were determined in the following manner: The area of the signal for the three aromatic protons of the mesitylene internal standard (~6.75 ppm) was set at 25.00. The areas of the peaks for the two terminal alkene protons of styrene were determined in the initial spectra, as well as the areas of the two peaks for the vinylidene protons of the major product at 72 hours. The ratios of these values were determined, giving four measurements of the yield. These values were averaged for each run, and then these two values were averaged again to give a final NMR yield of ~88%. The peaks for the minor regioisomer (d, 3H, 1.23 ppm, $CH_3$; m, 1H, 3.25 ppm, —CH(CH$_3$)Ph) were also integrated in the 72 h spectra, giving an average NMR yield of ~2%.

NMR Yields:
Run 1: 82.8%; 89.3%; 85.6%; 92.3%. Average: 87.5% (Minor isomer: 2.3%)
Run 2: 84.4%; 86.3%; 90.9%; 92.9%. Average: 88.6% (Minor isomer: 2.3%)

Once NMR yields were established, the two samples were combined and diluted with dichloromethane to a total volume of ~4 mL. Adamantane (16.2 mg, GC standard) was added, and the mixture analyzed by GC (see FIG. 26). The yield of both major and minor styrene dimers was determined to be 81% (major) and 2% (minor).

Heating a 500 mM solution of styrene in $C_6D_6$ with 25 mM dimerization catalyst 1 to 110° C. does in fact lead to dimerization, albeit slowly ($t_{1/2}$~14 h, see Scheme VIII). By $^1H$ NMR spectroscopy and GC analysis, there is one major product of this reaction, the "head-to-tail" dimer formed. Interestingly, there is a complete switch in regioselectivity from reactions with LAOS; the "tail-to-tail" product in styrene dimerization is formed.

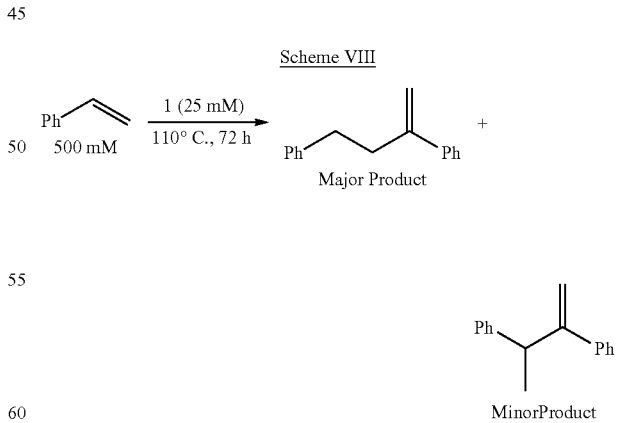

Scheme VIII

Procedure for Monitoring Dimerization of Styrene Over Four Half Lives.

Dimerization catalyst 1 (6.6 mg, 0.016 mmol), styrene (53.0 mg, 0.509 mmol), and 1,3,5-trimethoxybenzene (internal standard, 1.6 mg) were dissolved in $C_6D_6$ (2 mL). This solution was then split evenly into four J. Young NMR tubes. Initial $^1$H NMR spectra were recorded, and then the tubes were heated to either 100° C. (two tubes) or 125° C. (two tubes) in an oil bath. After set time intervals, the tubes were removed from the oil baths and new spectra acquired, until ~4 half lives had passed. The three aromatic protons of the 1,3,5-trimethoxybenzene internal standard (~6.25 ppm) were integrated versus the terminal vinylic proton of styrene that is cis relative to the phenyl group (~5.6 ppm), with the former area set at 25.00. The concentration of styrene at each time point was determined by the following formula, wherein $[Styrene]_0$=0.255 M; I=area of vinylic signal @5.6 ppm; and $I_0$=initial area of vinylic signal @5.6 ppm:

$$[Styrene]=[Styrene]_0 \times (I/I_0)$$

The dimerization of Styrene was evaluated by $^1$H NMR over various time points (see FIGS. 29-32).

Initial Rates of Styrene/1-Heptene Co-Dimerization Using Dimerization Catalyst 1.

Dimerization catalyst 1 (10.1 mg, 0.0243 mmol), styrene (97.7 mg, 0.938 mmol), 1-heptene (76.0 mg, 0.774 mmol), and adamantane (internal standard, 12.0 mg, 0.088 mmol) were dissolved in 2.8 mL of n-decane in a 4 mL screw-top vial containing a Teflon-coated stir bar. The vial was sealed with a Teflon-lined screw cap and the contents stirred vigorously to ensure complete dissolution of dimerization catalyst 1. The solution was then split into fifteen aliquots of 0.2 mL each in fifteen separate 4 mL vials containing stir bars. These vials were sealed and stirred at 100° C. in an aluminum block heater. At specified time intervals, (1, 2, 3, or 4 minutes) vials were removed from the heat block, immersed in a dry-ice/acetone bath to rapidly cool the contents, and then diluted with dichloromethane to quench the reaction. These solutions were passed through a short plug of silica gel into a GC autosampler vial, and analyzed by GC.

Data for each time point was collected from 3 different vials, giving 12 data points for each initial rate determination. The concentrations of the 1-heptene dimers (both regioisomers combined), and the co-dimers (all isomers combined) were plotted versus time, and the $k_{obs}$ values calculated by linear regression analysis (see FIG. 35). In order to normalize for the different concentrations of 1-heptene and styrene used, the initial rate for styrene dimerization was multiplied by a factor of 0.825 (the ratio of $[1\text{-heptene}]_0/[styrene]_0$), giving an initial rate ratio of 4.05:1 for 1-heptene dimerization versus styrene/1-heptene co-dimerization. Styrene dimers were not observed under these conditions.

Procedure for Co-Dimerization of Styrene/1-Heptene Using Dimerization Catalyst 1.

Dimerization catalyst 1 (20.4 mg, 0.050 mmol), styrene (52.1 mg, 0.500 mmol), 1-heptene (49.0 mg, 0.499 mmol), and adamantane (internal standard, 10.2 mg, 0.075 mmol) were dissolved in 2 mL of n-heptane in a 4 mL screw-top vial containing a Teflon-coated stir bar. The vial was sealed with a Teflon-lined screw cap and the contents stirred at 100° C. in an aluminum block heater. After 18 hours, the vial was removed, and the contents diluted with dichloromethane to a total volume of ~4 mL. This solution was passed through a short plug of silica gel before analysis by GC and GC/MS (see FIGS. 36-42).

Synthesis of Authentic Co-Dimers:

(1-Methyl-2-methylene-octyl)-benzene was prepared by Ni-catalyzed coupling of 1-heptene and styrene according to Ho et al., *Angew. Chem. Int. Ed.* 49:9182 (2010). Briefly: Under an $N_2$ atmosphere, Ni[COD]$_2$ (27.5 mg, 0.10 mmol) and 1,3-bis(2,6-diisopropylphenyl)-1,3-dihydro-2H-imidazol-2-ylidene (IPr, 38.9 mg, 0.10 mmol) were dissolved in toluene (4 mL) in a reaction tube and stirred for ~1 hour. An aliquot of 1-heptene (~28 µL) was added, followed by the addition of triethylamine (60.7 mg, 0.60 mmol), p-anisaldehyde (13.6 mg, 0.10 mmol), and TESOTf (52.9 mg, 0.20 mmol). The solution was stirred for ~15 minutes. Finally, styrene (208.3 mg, 2.00 mmol) and 1-heptene (589.1 mg, 6.00 mmol) were added, and the solution was stirred for ~24 hours at room temperature under $N_2$. The contents were then exposed to air and diluted with hexanes (~10 mL). The mixture was filtered through a short silica plug, followed by elution of the solid with 20% EtOAc in hexanes (~25 mL). The solvent was evaporated, and the residue dissolved in dichloromethane. The product solution was analyzed by GC and GC/MS (see FIGS. 43-46). The regiochemistry of the major co-dimer was definitively established by Ho et al., as well as the regiochemistry of styrene homodimerization. This co-dimer solution was co-injected with the co-dimer mixture generated by dimerization catalyst 1 (see FIG. 47).

Procedure for Monitoring Styrene/n-Heptane Coupling Reactions Over Time:

Dimerization catalyst 1 (6.6 mg, 0.016 mmol) and 2 (17.7 mg, 0.030 mmol) were dissolved in 2 mL of a standard solution of styrene (250 mM) and adamantane (25.3 mM) in n-heptane in a 4 mL screw top vial containing a Teflon-coated stir bar. The vial was sealed with a Teflon-lined screw cap. The mixture was heated to 100° C. for ~30 seconds in an aluminum block heater inside an argon-filled glovebox to dissolve the precatalysts and ensure a homogeneous solution, and then immediately cooled to −35° C. in the freezer. An aliquot (~0.1 mL, representing to) was removed and placed into a GC autosampler vial; this aliquot was then diluted with dichloromethane to a total volume of ~1 mL before analysis by GC.

The reaction mixture was heated to 100° C. in the aluminum block heater, and at specified times (1, 2, 3, 4, 5, 6, 7, 8, 10, 12, and 18 hours) the vial was removed and cooled to −35° C. in the freezer before taking an aliquot for analysis by GC. The concentrations of all major species were then plotted versus time to give time course profiles of the tandem reaction (see FIG. 48). The effects of the cooperativity in Styrene/n-Heptane Coupling by dimerization catalyst 1 and hydrogen transfer catalyst 2 is presented in Table 4.

TABLE 4

Evaluation of Catalyst Cooperativity in Styrene/n-Heptane Coupling by 1 and 2.

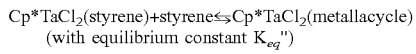

| Entry | [Styrene]$_0$ (mM) | [1]/[2] (mM) | Time (h) | Temp. (° C.) | % Conv. | EB (mM)$^a$ | Styrene Dimer (mM)$^a$ | Co-Dimers (mM)$^a$ | Heptane Dimers (mM)$^a$ | TON for 1$^b$ | TON for 2$^b$ | Coop. (%) |
|---|---|---|---|---|---|---|---|---|---|---|---|---|
| 1 | 250 | 8/5 | 18 | 100 | 62 | 70 | 23 | 23 | 11 | 7 (4) | 14 (9) | 63 |
| 2 | 250 | 8/5 | 48 | 100 | 75 | 71 | 35 | 28 | 12 | 9 (5) | 14 (10) | 72 |
| 3 | 250 | 5/8 | 18 | 100 | 78 | 132 | 11 | 27 | 26 | 13 (11) | 17 (10) | 60 |
| 4 | 250 | 5/10 | 18 | 100 | 89 | 162 | 8 | 26 | 35 | 14 (12) | 16 (10) | 60 |
| 5 | 250 | 10/10 | 18 | 100 | 99 | 163 | 17 | 31 | 42 | 9 (7) | 16 (11) | 70 |
| 6 | 250 | 10/15 | 18 | 100 | 99 | 192 | 6 | 24 | 46 | 8 (7) | 13 (8) | 60 |
| 7 | 250 | 8/15 | 18 | 100 | 99 | 202 | 4 | 20 | 44 | 8 (8) | 13 (7) | 53 |
| 8 | 1000 | 10/15 | 72 | 100 | 67 | 99 | 229 | 42 | 4 | 27 (5) | 7 (3) | 50 |
| 9 | 250 | 10/15 | 18 | 125 | 99 | 215 | 2 | 15 | 38 | 5 (5) | 14 (6) | 42 |
| 10 | 250 | 10/15 | 18 | 150 | >99 | 209 | 2 | 14 | 36 | 5 (5) | 14 (6) | 41 |

$^a$Determined by GC/FID using adamantane as an internal std., avg. of at least 2 runs.
$^b$TONs in parentheses are for production of co-dimers + heptane dimers.

Procedure for Monitoring Styrene/n-Heptane Transfer Hydrogenation Over Time:

Hydrogen transfer catalyst 2 (17.7 mg, 0.030 mmol) was dissolved in 2 mL of a standard solution of styrene (250 mM) and adamantane (25.3 mM) in n-heptane in a 4 mL screw top vial containing a Teflon-coated stir bar. The vial was sealed with a Teflon-lined screw cap. The mixture was heated to 100° C. for ~30 seconds in an aluminum block heater inside an argon-filled glovebox to dissolve the pre-catalysts and ensure a homogeneous solution, and then immediately cooled to −35° C. in the freezer. An aliquot (~0.1 mL, representing $t_0$) was removed and placed into a GC autosampler vial; this aliquot was then diluted with dichloromethane to a total volume of ~1 mL before analysis by GC.

The reaction mixture was heated to 100° C. in the aluminum block heater, and at specified times (1, 2, 3, 4, 5, 6, 7, 8, 10, 12, and 18 hours) the vial was removed and cooled to −35° C. in the freezer before taking an aliquot for analysis by GC. The concentrations of styrene and ethylbenzene were then plotted versus time to give time course profiles of the transfer hydrogenation reaction. These data were overlaid on the styrene/ethylbenzene concentrations from the tandem reaction (see FIG. 49).

Results of Styrene Dimerization and Styrene/1-Heptene Co-Dimerization Catalyzed by Dimerization Catalyst 1.

In the catalytic coupling of 1-hexene/n-heptane, competitive homodimerization of 1-hexene is prevalent; even with slow addition of 1-hexene by syringe pump, the $C_{12}$ fraction represents ~50% of the higher molecular weight products. In an effort to minimize this side reaction, TBE was initially examined as a possible sacrificial hydrogen acceptor that would not be incorporated into the dimerization catalytic cycle, enabling the catalytic dimerization of alkanes.

While modest yield was achieved with TBE, poor conversion and suspected catalyst decomposition led to the consideration other hydrogen acceptors. Styrene is an attractive alternative, since competitive alkene isomerization would be avoided. Furthermore, the ethylbenzene generated during transfer hydrogenation could, in principle, be regenerated by dehydrogenation (steam cracking), which is practiced industrially on a large scale to synthesize styrene monomer.

In previously reported studies, the stoichiometric and catalytic alkene dimerization by dimerization catalyst 1 and related complexes was not reported for the dimerization of styrenes. While the Cp*TaCl$_2$(styrene) complex was prepared and characterized, attempts to observe metallacycles derived from two styrene units, or styrene and an aliphatic alkene, were unsuccessful. These observations (or rather lack thereof) were encouraging in the context of tandem catalysis, as competitive dimerization of the hydrogen acceptor (i.e. styrene) should be minimized.

Figure 7:
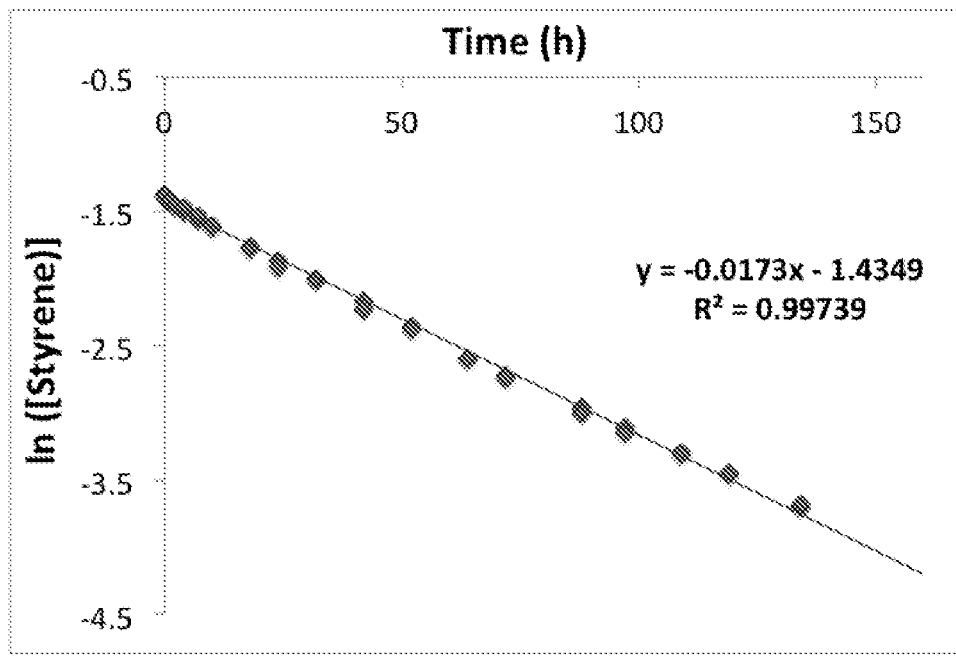
FIG. 7. Plot of ln([styrene]) versus time for the dimerization of styrene (250 mM) catalyzed by 1 (8 mM) at 100° C.

Monitoring the dimerization of styrene under conditions analogous to tandem catalysis (250 mM styrene, 8 mM dimerization catalyst 1, 100° C.) reveals strict exponential decay of styrene up to ~3.5 half-lives, with $t_{1/2}$=40 h (see FIG. 7); deviation from linearity at high conversion is likely due to product inhibition, as observed for 1-hexene dimerization. This first order dependence on [styrene] is consistent with a mechanism analogous to the top catalytic cycle in Scheme V, where the equilibrium of:

Cp*TaCl$_2$(styrene)+styrene⇌Cp*TaCl$_2$(metallacycle)
(with equilibrium constant $K_{eq}''$)

heavily favors reactants, which is in accord with the inability to observe metallacycles derived from styrenes. The observed first order rate constant $k_{obs}=K_{eq}''k_3$[Ta]$_0$, and therefore $K_{eq}''k_3$=6.00 (6)×10$^{-4}$ M$^{-1}$ s$^{-1}$ (where $k_3$ is the rate constant for the unimolecular decomposition of the styrene metallacycle, analogous to $k_2$ in Scheme V). Comparing $K_{eq}''k_3$ to the corresponding values for 1-hexene dimerization to the major and minor isomers gives a ratio of 53:17:1($K_{eq}k_1:K_{eq}'k_2:K_{eq}''k_3$); thus 1-hexene dimerization is ~70× faster than styrene dimerization.

The markedly slower dimerization of styrene relative to 1-hexene means that styrene should be useful as a sacrificial hydrogen acceptor in tandem catalysis; however, co-dimerization of styrene and the alkane is another likely product. In order to determine the relative rates of LAO dimerization relative to styrene/LAO coupling, a mixture of styrene (313 mM) and 1-heptene (258 mM) was dimerized with dimerization catalyst 1. Under initial rate conditions, 1-heptene dimerization is 4× faster than 1-heptene/styrene co-dimerization. Notably, under these conditions 1-heptene dimerization is 2.8× slower than 1-hexene dimerization in the absence of styrene. Clearly, the presence of styrene inhibits LAO dimerization, probably because Cp*TaCl$_2$(styrene) is a significant resting state, which could be a complicating factor in achieving a high degree of tandem catalysis.

Analysis of the GC traces of these initial rate experiments indicated that there are multiple styrene/1-heptene co-dimer products. Running a 1-heptene/styrene co-dimerization to completion gives 1-heptene dimers, co-dimers, and styrene dimer. By GC, there appear to be three or four co-dimers (one peak has a consistent shoulder), with one major species. If both "tail-to-tail" and "head-to-tail" regioisomers are considered, there are four possible products (Scheme IX).

Scheme IX

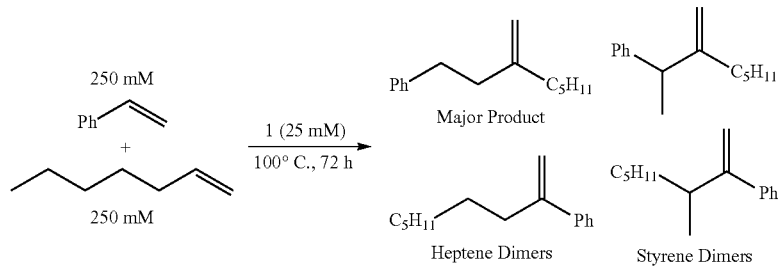

Other embodiments, combinations and modifications of the compositions and methods presented herein will occur readily to those of ordinary skill in the art in view of these teachings. Therefore, the compositions and methods are to be limited only by the following claims, which include all such embodiments and modifications when viewed in conjunction with the above specification and accompanying drawings.

The invention claimed is:

1. A method of coupling a n-alkane reactant with a n-alkene reactant so as to form one or more branched alkene products in a single tandem process, comprising:
   coupling a n-alkane reactant with a n-alkene reactant in the presence of a catalyst comprising: (i) a hydrogen transfer catalyst and (ii) an alkene dimerization catalyst so as to generate one or more branched alkene products, wherein the molecular weight of the one or more branched alkene products is greater than the molecular weight of the n-alkane reactant and greater than the molecular weight of the n-alkene reactant;
   wherein the hydrogen transfer catalyst is a pincer complex catalyst, and
   wherein the alkene dimerization catalyst is a tantalum catalyst that is selective for the formation of dimer products comprising a structure of Formula II:

wherein,
Z is either 1 or 2;
n is an integer from 1 to 5;
each Y is independently selected from the group consisting of D, H, optionally substituted $C_1$-$C_6$ alkyl, silane, and $C_1$-$C_4$ alkylsilane;
$Y^1$ is selected from the group consisting of H, D, halo, =S, =O, PMe$_3$, and =C(H)(CMe$_3$);
$Y^2$ is selected from the group consisting of H, D, halo, =S, =O, and PMe$_3$, or $Y^2$ is absent;
$R^2$ is selected from the group consisting of H, aryl, optionally substituted $C_{15}$ alkyl, and optionally substituted $C_1$-$C_{15}$ hetero-alkyl; and
$R^3$ is selected from the group consisting of H, aryl, optionally substituted $C_{15}$ alkyl, and optionally substituted $C_1$-$C_{15}$ hetero-alkyl,
wherein the one or more branched alkene products comprise one or more carbon atoms from both the n-alkane reactant and the n-alkene reactant.

2. The method of claim 1, wherein the alkene dimerization catalyst comprises a structure of Formula II(a):

wherein,
$R^2$ is selected from the group consisting of aryl, optionally substituted $C_1$-$C_{15}$ alkyl, and optionally substituted $C_1$-$C_{15}$ hetero-alkyl.

3. The method of claim 1, wherein the hydrogen transfer catalyst is immobilized on a solid support, wherein the coupling is carried out in a solvent, and wherein the method further comprises the step of separating free hydrogen transfer catalyst from the solvent.

4. The method of claim 1, wherein the n-alkane reactant is a $C_5$-$C_{10}$ n-alkane.

5. The method of claim 1, wherein the n-alkene reactant is a $C_5$-$C_{10}$ n-alkene.

6. The method of claim 1, wherein the method further comprises hydrogenating or reducing the one or more branched alkene products to produce one or more branched alkane products.

7. A method for coupling a first n-alkane reactant with a second n-alkane reactant to form one or more branched alkene products, comprising:

coupling the first n-alkane reactant with the second n-alkane reactant using styrene as a sacrificial hydrogen acceptor in the presence of a catalyst comprising: (i) a hydrogen transfer catalyst and (ii) an alkene dimerization catalyst so as to generate one or more branched alkene products, wherein the molecular weight of the one or more branched alkene products is greater than the molecular weight of the first n-alkane reactant and greater than the molecular weight of the second n-alkane reactant;

wherein the hydrogen transfer catalyst is a pincer complex catalyst, and wherein the alkene dimerization catalyst is a tantalum catalyst that is selective for the formation of dimer products comprising a structure of Formula II,

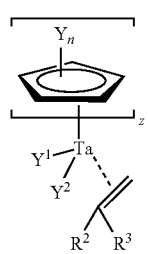

(II)

wherein:
Z is either 1 or 2;
n is an integer from 1 to 5;
each Y is independently selected from the group consisting of D, H, optionally substituted $C_1$-$C_6$ alkyl, silane, and $C_1$-$C_4$ alkylsilane;
$Y^1$ is selected from the group consisting of H, D, halo, $=S$, $=O$, $PMe_3$, and $=C(H)(CMe_3)$;
$Y^2$ is selected from the group consisting of H, D, halo, $=S$, $=O$, $PMe_3$, or $Y^2$ is absent;
$R^2$ is selected from the group consisting of H, aryl, optionally substituted $C_{15}$ alkyl, and optionally substituted $C_1$-$C_{15}$ hetero-alkyl; and
$R^3$ is selected from the group consisting of H, aryl, optionally substituted $C_{15}$ alkyl, and optionally substituted $C_1$-$C_{15}$ hetero-alkyl,
wherein the one or more branched alkene products comprise carbon atoms from both the first n-alkane reactant and the second n-alkane reactant.

8. The method of claim 7, wherein the alkene dimerization catalyst comprises a structure of Formula II(a):

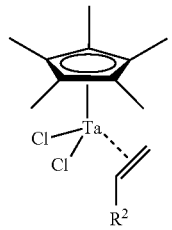

II(a)

wherein,
$R^2$ is a phenyl.

9. The method of claim 7, wherein the first n-alkane reactant and the second n-alkane reactant are $C_5$-$C_{10}$ n-alkanes.

10. The method of claim 7, wherein the method further comprises hydrogenating or reducing the one or more branched alkene products to produce one or more branched alkane products.

11. A method of coupling a n-alkane reactant with a n-alkene reactant so as to form one or more branched alkene products in a single tandem process, comprising:

coupling a n-alkane reactant with a n-alkene reactant in the presence of a catalyst comprising: (i) a hydrogen transfer catalyst and (ii) an alkene dimerization catalyst so as to generate one or more branched alkene products, wherein the molecular weight of the one or more branched alkene products is greater than the molecular weight of the n-alkane reactant and greater than the molecular weight of the n-alkene reactant;

wherein the alkene dimerization catalyst is a tantalum catalyst that is selective for the formation of dimer products, and wherein the hydrogen transfer catalyst is an iridium pincer complex catalyst comprising the structure of Formula I:

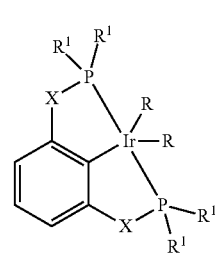

(I)

wherein,
each R is independently a H or a $C_1$-$C_{30}$ hydrocarbyl radical;
each $R^1$ is independently a $C_1$-$C_{30}$ hydrocarbyl radical; and
each X is independently an O or $CH_2$,
wherein the one or more branched alkene products comprise one or more carbon atoms from both the n-alkane reactant and the n-alkene reactant.

12. The method of claim 11, wherein the iridium pincer complex catalyst comprises a structure of Formula I(a):

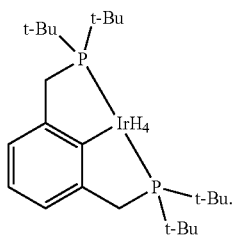

I(a)

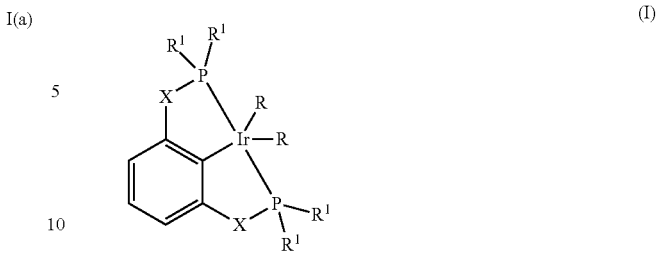

(I)

13. The method of claim 11, wherein the hydrogen transfer catalyst is immobilized on a solid support, wherein the coupling is carried out in a solvent, and wherein the method further comprises the step of separating free hydrogen transfer catalyst from the solvent.

14. The method of claim 11, wherein the n-alkane reactant is a $C_5$-$C_{10}$ n-alkane.

15. The method of claim 11, wherein the n-alkene reactant is a $C_5$-$C_{10}$ n-alkene.

16. A method for coupling a first n-alkane reactant with a second n-alkane reactant to form one or more branched alkene products, comprising:

coupling the first n-alkane reactant with the second n-alkane reactant using styrene as a sacrificial hydrogen acceptor in the presence of a catalyst comprising: (i) a hydrogen transfer catalyst and (ii) an alkene dimerization catalyst so as to generate one or more branched alkene products, wherein the molecular weight of the one or more branched alkene products is greater than the molecular weight of the first n-alkane reactant and greater than the molecular weight of the second n-alkane reactant;

wherein the alkene dimerization catalyst is a tantalum catalyst that is selective for the formation of dimer products, and wherein the hydrogen transfer catalyst is an iridium pincer complex catalyst comprising a structure of Formula I, wherein,
each R is independently a H or a $C_1$-$C_{30}$ hydrocarbyl radical;
each $R^1$ is independently a $C_1$-$C_{30}$ hydrocarbyl radical; and
each X is independently an O or $CH_2$,
wherein the one or more branched alkene products comprises carbon atoms from both the first n-alkane reactant and the second n-alkane reactant.

17. The method of claim 16, wherein the iridium pincer complex catalyst comprises a structure of Formula II(a):

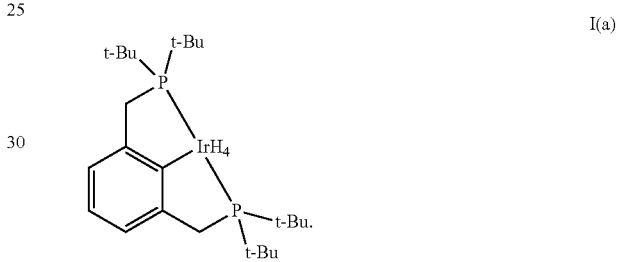

I(a)

18. The method of claim 16, wherein the first n-alkane reactant and the second n-alkane reactant are $C_5$-$C_{10}$ n-alkanes.

19. The method of claim 16, wherein the method further comprises hydrogenating or reducing the one or more branched alkene products to produce one or more branched alkane products.

* * * * *